United States Patent [19]
Zuckermann et al.

[11] Patent Number: 5,877,278
[45] Date of Patent: Mar. 2, 1999

[54] SYNTHESIS OF N-SUBSTITUTED OLIGOMERS

[75] Inventors: Ronald N. Zuckermann, Berkeley; Dane A. Goff, Redwood City; Simon Ng, Walnut Creek; Kerry Spear, Oakland, all of Calif.; Barbara O. Scott, San Antonio, Tex.; Aaron C. Sigmund, El Sobrante, Calif.; Richard A. Goldsmith, Daly City, Calif.; Charles K. Marlowe, San Carlos, Calif.; Yazhong Pei, Alisa Viejo, Calif.; Lutz Richter, Montera, Calif.; Reyna Simon, Felton, Calif.

[73] Assignee: Chiron Corporation, Emeryville, Calif.

[21] Appl. No.: 487,282

[22] Filed: Jun. 7, 1995

Related U.S. Application Data

[63] Continuation-in-part of Ser. No. 277,228, Jul. 18, 1994, abandoned, which is a continuation-in-part of Ser. No. 126,539, Sep. 24, 1993, abandoned, which is a continuation-in-part of Ser. No. 950,853, Sep. 24, 1992, abandoned.

[51] Int. Cl.$^6$ ....................................................... C07K 1/04
[52] U.S. Cl. ............................ 530/334; 530/317; 544/98; 544/358
[58] Field of Search ................................... 530/333, 334, 530/317; 544/98, 358

[56] References Cited

U.S. PATENT DOCUMENTS

| | | | |
|---|---|---|---|
| 3,634,364 | 1/1972 | Greenbelt et al. | 260/78 |
| 5,143,854 | 9/1992 | Pirrung et al. | 436/518 |
| 5,182,366 | 1/1993 | Huebner et al. | 530/334 |
| 5,194,392 | 3/1993 | Geysen | 436/518 |
| 5,225,533 | 7/1993 | Rutter et al. | 530/334 |
| 5,252,296 | 10/1993 | Zuckermann et al. | 422/116 |
| 5,266,684 | 11/1993 | Rutter et al. | 530/334 |
| 5,288,514 | 2/1994 | Ellman | 427/2 |
| 5,539,083 | 7/1996 | Cook et al. | 530/333 |

FOREIGN PATENT DOCUMENTS

| | | |
|---|---|---|
| 1037474 | 7/1966 | European Pat. Off. . |
| 24 47 305 | 4/1975 | Germany . |

OTHER PUBLICATIONS

Zuckerman, Ronald et al., "Efficient Method for the Preparation of Peptoids [Oligo(N–substituted glycines)] by Submonomer Solid–Phase Synthesis", *J. Am. Chem. Soc.* (1992) vol. 114:10646–10647.

Simon, Reyna et al., "Peptoids: A Modular Approach to Drug Discovery" *Proc. Nat.l Acad. Sci. USA* (1992) vol. 89:9367–9371.

Zuckerman, Ronald et al., "Efficient Method for the Preparation of Peptoids [Oligo(N–substituted glycines)] by Submonomer Solid–Phase Synthesis", *Chemtracts–Macromolecular Chemistry* (1993) vol. 4:80–83.

Marcincin, Anton et al., "Studium Adheznych Vlastnosti N–Substituovanych Polyamidov.ll. Adhezna Praca N–Alkoxymetyl–Poly–Kaprolaktamu Kniektorym Polymerom", *Plasty Kauc* (1975) vol. 12:101–104.

Kasica, H. et al., "Electrical Conductivity of N–Substituted Polyamides", *Journal of Polymer Science Part A–1* vol. 6:1615–1623.

Cosani A. et al., "N–Substituted Poly ( –amino acids). 1. Synthesis and Characterization of Poly (N–methyl–y–mehtyl L–Glutamate) and Poly ( N–methyl–Y–ethyl L–glutamate)$^1$", *Macromolecules* (1978) vol. 11 No. 5;1041–1045.

(List continued on next page.)

*Primary Examiner*—Cecilia J. Tsang
*Assistant Examiner*—David Lukton
*Attorney, Agent, or Firm*—Bret Field; Kenneth M. Goldman; Robert P. Blackburn

[57] ABSTRACT

A solid-phase method for the synthesis of N-substituted oligomers, such as poly (N-substituted glycines) (referred to herein as poly NSGs) is used to obtain oligomers, such as poly NSGs of potential therapeutic interest which poly NSGs can have a wide variety of side-chain substituents. Each N-substituted glycine monomer is assembled from two "sub-monomers" directly on the solid support. Each cycle of monomer addition consists of two steps: (1) acylation of a secondary amine bound to the support with an acylating agent comprising a leaving group capable of nucleophilic displacement by —$NH_2$, such as a haloacetic acid, and (2) introduction of the side-chain by nucleophilic displacement of the leaving group, such as halogen (as a solid support-bound α-haloacetamide) with a sufficient amount of a second sub-monomer comprising an —$NH_2$ group, such as a primary amine, alkoxyamine, semicarbazide, acyl hydrazide, carbazate or the like. Repetition of the two step cycle of acylation and displacement gives the desired oligomers. The efficient synthesis of a wide variety of oligomeric NSGs using automated synthesis technology of the present method makes these oligomers attractive candidates for the generation and rapid screening of diverse peptidomimetic libraries. The oligomers of the invention, such as N-substituted glycines (i.e. poly NSGs) disclosed here provide a new class of peptide-like compounds not found in nature, but which are synthetically accessible and have been shown to possess significant biological activity and proteolytic stability.

Combinatorial libraries of cyclic compounds are disclosed wherein the cyclic compounds are comprised of at least one ring structure derived from cyclization of a peptoid backbone. The diversity of product compounds is generated by the sequential addition of substituted submonomers. The combinatorial library includes 10 or more, preferably 100 or more, and more preferably 1,000 or more distinct and different compounds. The library includes each of the product compounds in retrievable and analyzable amounts and preferably includes at least one biologically active compound. Methods of synthesizing the combinatorial libraries and assay devices produced using the libraries are disclosed as is methodology for screening for and obtaining biologically active cyclic organic compounds.

8 Claims, 2 Drawing Sheets

OTHER PUBLICATIONS

Barrow, C.J. et al., "WIN 64821, A New Competitive Antagonist to Substance P, Isolated from an *Aspergillus* Species: Structure Determination and Solution Conformation", *J.Org.Chem.* (Apr. 1993) vol. 58:6016–6021.

Beebe, Xenia et al., "Polymer–Supported Synthesis of 2,5 Disubstituted Tetrahydrofurans" *J.Am.Chem.Soc.* (Jul. 1992) vol. 114:10061–10062.

Bunin, Barry A. and Ellman Jonathan A., "A General and Expedient Method for the Solid–Phase Synthesis of 1,4–Benzodiazephine Derivatives", *J.Am.Chem.Soc.* (Oct. 1992) vol. 114:10997–10998.

Bunin, Barry A. et al., "The Combinatorial Synthesis and Chemical and Biological Evaluation of a 1,4–Benzodiazephine Library", *Proc.Natl.Acad.Sci. USA* (May. 1994) vol. 91:4708–4712.

Chen, Chixu, et al., "'Analogous' Organic Synthesis of Small–Compound Libraries: Validation of Combinatorial Chemistry in Small–Molecule Synthesis," *J. Am. Chem. Soc.,* (1994) vol. 116, pp. 2661–2662.

Cho, Charles Y., "An Unnatural Biopolymer," *Science,* (Sep. 3, 1993) vol. 261, pp. 1303–1305.

Chu, Min et al., "Two Novel Diketopiperazine Isolated From the Fungus *Tolypocladium* sp.", *Tetrahedron Lett.* (Sep. 1993) vol. 34, No. 47:7537–7540.

Deshpande, Milind S., "Formation of Carbon–Carbon Bond on Solid Support: Application of the Stille Reaction", *Tetrahedron Lett.* (1994) vol. 35, No. 31:5613–5614.

Furka, A., et al., "Cornucopia of Peptides by Synthesis", Dept. Org. Chem, Univ. Budapest, Hungary. [Note: This is the best copy available].

Gelin, Jacques et al., "Synthetic Studies on Thaxtomins A and B, Phytotoxins Associated with *Streptomyces scabies,* the Causal Organism of Potato Common Scab", *J.Org.Chem.* (Jun. 1993) vol. 58, No. 13:3473–3475.

Gordon, D.W. and Steele, J., "Reductive Alkylation on a Solid Phase: Synthesis of a Piperazinedione Combinatorial Library", *Bioorg. and Med. Chem. Lett.* (1995) vol. 5:47–50.

Hobbs–DeWitt, Sheila, et al., "'Diversomers': An Approach to Nonpeptide, Nonoligomeric Chemical Diversity", *Proc.Natl.Acad.Sci. USA* (Aug. 1993) vol. 90:6909–6913.

Kanemasa, S. and Tsage, O., "N–Metalated Azomethine Ylides" *Adv. Cycloaddition* (1993) vol. 3:99–159.

Kates S.A. et al., "Automated Allyl Cleavage for Continuous–Flow Synthesis of Cyclic and Branched Peptides" *Anal.Biochem.* (1993) vol. 212:303–310.

Robey, F.A. et al. "Synthesis, Analyses and Uses of Site–Specific Bromoacetyl–Derivatized Synthetic Peptides: Starting Materials for Countless New Cyclic Peptides, Peptomers and Peptide Conjugates", *Chimica Oggi* (1992) 27–31.

Shimazaki, N. et al., "$N^6$–2,2 Diphenylethyl)adenosine, a Novel Adenosine Receptor Agonist with Antipsychotic–like Activity" (1987) vol. 30:1709–1711.

Stewart, J.M. and Young, J.D., "Solid Phase Peptide Synthesis", (2nd ed.), Pierce, Rockford, Il (1984) 30–31.

Yu, K.–L et al. "Heck Reactions in Solid Phase Synthesis", *Tet.Lett.* (Aug. 1994) vol. 35:8919–8922.

Zuckermann et al., "Discovery of Nanomolar Ligands for 7–Transmembrane G–Protein–Coupled Receptors from a Diverse N–(Substituted)glycine Peptoid Library" *J.Med.Chem.* (1994) vol. 37:2678–2685.

SYNTHESIS OF N-SUBSTITUTED OLIGOMERS

CROSS-REFERENCE TO RELATED APPLICATIONS

This application is a continuation-in-part of our earlier filed U.S. application Ser. No. 08/277,228 filed Jul. 18, 1994 now abandoned, which application is a continuation-in-part of our earlier filed U.S. patent application Ser. No. 08/126,539 filed Sep. 24, 1993 (now abandoned) which application is a continuation-in-part of our earlier filed U.S. patent application Ser. No. 07/950,853 filed Sep. 24, 1992 now abandoned, which applications are incorporated herein by reference in their entirety and to which applications we claim priority under 35 USC § 120.

FIELD OF THE INVENTION

This present invention relates generally to chemical synthesis technologies. More particularly, the present invention relates to the synthesis of N-substituted oligomers and particularly to peptide-like compounds in the form of poly (N-substituted glycines) (referred to herein as poly NSGs) using solid-phase synthesis methods. The present invention also relates to the solid phase synthesis of heterocyclic organic compounds in which an N-substituted glycine monomer unit forms the backbone. The invention also relates to combinatorial libraries or mixtures of such heterocyclic organic compounds to be assayed for biological activity.

BACKGROUND OF THE INVENTION

Standard methods analogous to classical solid-phase methods for peptide synthesis could be applied for the synthesis of NSGs. In accordance with such methods, the carboxylate of N,α-Fmoc-protected (and side-chain protected) NSGs would be activated and then coupled to a solid support-bound amino group. The Fmoc group is then removed followed by addition of the next monomer. Thus, oligomeric NSGs could be prepared as condensation homopolymers of N-substituted glycine. Such an approach is not desirable due to the time and cost of preparing suitable quantities of a diverse set of protected N-substituted glycine monomers. Adding and removing the Fmoc or other protective groups is time consuming and inefficient.

One approach to the discovery of new pharmaceutically active organic drugs (i.e., compounds with the 3-D structure needed for binding) relies primarily on X-ray crystallography of purified receptors: once the binding site is identified, organic molecules are designed to fit the available steric space and charge distribution. However, it is often difficult to obtain purified receptors, and still more difficult to crystallize the receptor so that X-ray crystallography may be applied. It is also nontrivial to devise an appropriate ligand, even after the binding site has been properly identified. Overall, it is extremely difficult to design useful pharmaceutically active compounds due to a number of factors such as the difficulty in identifying receptors, purifying and identifying the structures of compounds which bind to those receptors and thereafter synthesizing those compounds.

Another approach to the discovery of new drugs is to synthesize compounds which mimic known biologically active compounds. However, since the active moiety or active structural component of the active compound is usually unknown, the process of synthesizing new compounds relies primarily on trial and error and the synthesis and screening of each compound individually. This method is time consuming and expensive since the likelihood of success for any single compound is relatively low.

Rather than trying to determine the particular three-dimensional structure of a protein using crystallography or attempting to synthesize specific peptides which mimic a known biologically active peptide an art has developed with respect to the production of combinatorial libraries. More specifically, those attempting to isolate biologically active peptides produce extremely large numbers of different peptides at the same time within the same reaction vessel. The synthesized combinatorial library is then assayed and active molecules are isolated and analyzed. Combinatorial libraries per se are disclosed within U.S. Pat. No. 5,266,684. U.S. Pat. No. '684 relates almost completely to the synthesis of libraries wherein each of the reaction products in the library is a peptide comprised of the twenty naturally occurring amino acids.

Since pharmaceutically active compounds are often highly substituted heterocycles, there is currently a need for a method to rapidly synthesize a large number of related substituted heterocyclic compounds quickly and relatively inexpensively. This approach would overcome the problem of a separate synthesis for each member of a group of candidate compounds where the structural components conferring biological activity are unknown.

SUMMARY OF THE INVENTION

A synthesis method is disclosed whereby each N-substituted monomer is assembled from two "sub-monomers" directly on a solid substrate. By varying the basic structure and the substituents on the sub-monomers a wide range of different oligomers can be produced, some of which mimic the structure and activity of natural proteins and nucleic acids or portions thereof.

N-substituted oligomers, such as N-substituted glycines (poly NSGs) are comprised of monomers prepared from two sub-monomers, the first sub-monomer being an acylating agent comprising a leaving group capable of nucleophilic displacement, such as a haloacetic acid and a second sub-monomer comprising a —$NH_2$ group, such as a primary amine. The direction of polymer synthesis with the sub-monomers occurs in the carboxy to amino direction.

The solid-phase assembly of each monomer—and concurrent polymer formation—eliminates the need for N,α-protected monomers. Only reactive side-chain functionalities need be protected.

Moreover, each sub-monomer is simpler in structure than the monomers previously used in synthesis of oligomers of amides, including amino acids. Many of the sub-monomers are commercially available, which dramatically reduces the time and cost required for poly NSG synthesis.

A primary object of the present invention is to provide a method of synthesizing poly (N-substituted amides) directly on a solid substrate support.

Another object of the invention is to provide solid-phase methods for synthesizing N-substituted oligomers, such as polymers of N-substituted glycines, which oligomers can have a wide variety of side-chain substituents.

An advantage of the present invention is that the methods can be carried out more efficiently than previous conventional synthesis using solid-phase methods.

An important embodiment of the invention is an automated and highly efficient solid-phase method for synthesizing a specific type of oligomer which is referred to herein as poly N-substituted amides, particularly poly (N-substituted glycines).

Another advantage of the present invention is that the methods eliminates the need for N,α-protected monomers.

A feature of the present invention is that only the reactive side-chain groups need be protected or blocked during the synthesis.

Yet another advantage of the present invention is that each sub-monomer of the monomer (and the oligomer) has a simple structure allowing for quick and efficient synthesis.

Another feature of the present invention is that many of the sub-monomer components used in connection with the invention are commercially available.

The invention also relates to mixtures of cyclic organic compounds. According to the invention, each cyclic organic compound is constructed from a peptoid backbone with the substituents varied such that a mixture of products is obtained. The invention further relates to methods of producing combinatorial libraries of cyclic organic compounds from cyclic and/or noncyclic precursor compounds.

A primary object of the present invention is to provide mixtures (libraries) containing large numbers of cyclic organic compounds derived from peptoids and covalently attached to a solid substrate or cleaved from the solid support which libraries contain at least one biologically active cyclic organic compound.

Another object of the invention is to provide a method of obtaining a library of cyclic organic compounds derived from peptoids which library contains at least one biologically active cyclic organic compound.

The invention features mixtures of N-substituted glycines (NSG) which may be linear with respect to the peptoid backbone. Alternatively, the peptoid backbone of the NSG may form a heterocyclic structure optionally having a peptoid covalently attached to the heterocycle. Preferably, the cyclic structure is a highly substituted isoquinolinone, isoquinoline, tetrahydroisoquinoline, tetrahydroisoquinolinone, phenanthridone, monoketopiperazine, pyrrolidine, benzodiazepine, and like compounds formed by 1) intramolecular cyclization of a peptoid backbone or 2) intermolecular reaction of a peptoid backbone and an acceptor molecule.

Another object of the invention is to provide methodology for screening such cyclic organic compound libraries in order to obtain compounds which mimic to some degree the activity of natural proteins or other biologically active compounds.

Another object of the present invention is to produce novel compounds which are cyclic organic compounds of the invention further bound to a bioactive compound such as a pharmaceutically active drug so as to provide biochemical targeting for the drug via the enhanced binding affinity of the synthesized cyclic organic compound of the invention.

An advantage of the present invention is that the methodology can be used to synthesize and isolate solid support-bound cyclic organic compounds with the strongest receptor binding affinity or other optimized target biological activity.

Another advantage of the present invention is that the cyclic organic compounds and libraries of the invention can be used to explore receptor interactions, i.e., the interaction between such compounds and the natural receptor sites.

Another object of the invention is to provide drug design methodology whereby cyclic organic compounds derived from peptoids are designed, which compounds have the same or stronger affinity for a natural receptor site as a bioactive protein or other bioactive molecule which binds to the same receptor site.

Another feature of the invention is that the chemical synthesis methodology is used in connection with solid phase reaction techniques, making it possible to produce defined libraries, and the solid phase reaction techniques can be automated to produce cyclic organic compounds and/or libraries in commercial quantities.

Yet another feature of the invention is that the substrate-bound cyclic organic compounds of the invention have not only different structures with respect to the bonds they contain as compared to natural peptides or other bioactive molecules, but have different three-dimensional structures which structures may not be possible with the natural peptides or other bioactive molecules.

These and other objects, advantages and features of the present invention will be come apparent to those persons of ordinary skill in the art upon reading the details of the structure, synthesis and usage and more fully set forth below, reference being made to the accompanying general structural formulas and synthesis schemes forming a part hereof wherein like symbols refer to like molecular moieties throughout.

DETAILED DESCRIPTION

Figure 1:
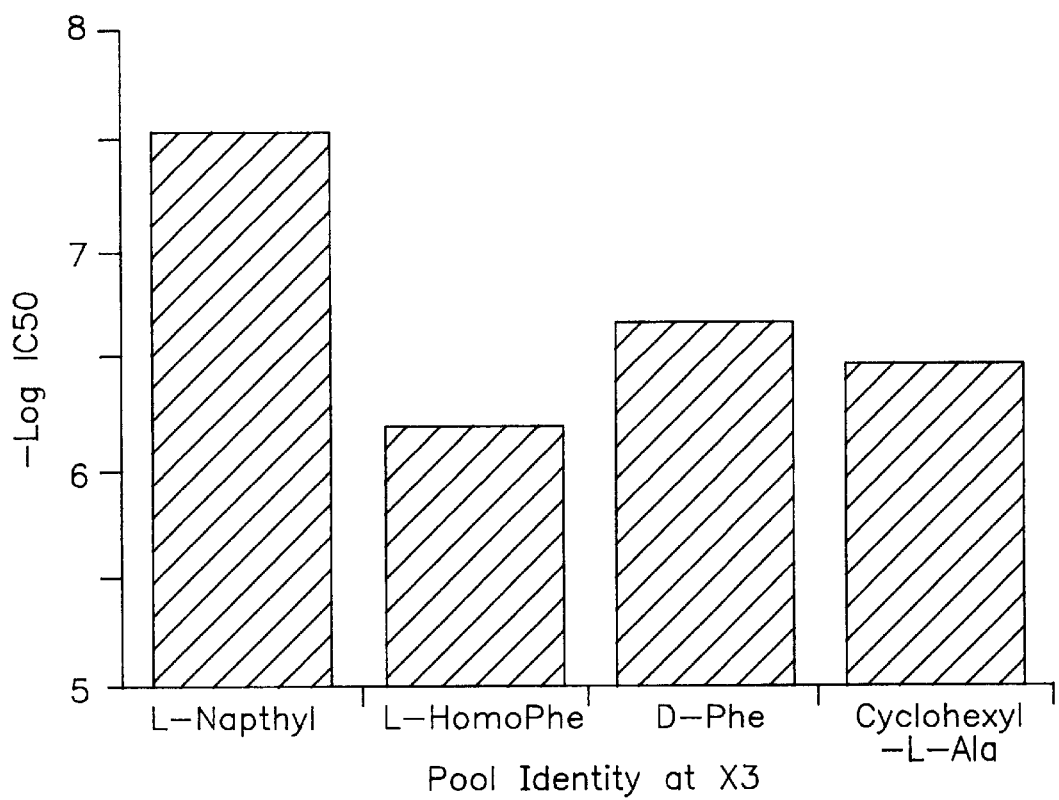
FIG. 1 is a graph showing the results of a competitive binding assay used to determine the $IC_{50}$ values (and relative binding affinities) of four separate libraries.

Before the present peptoid compounds and peptoid-derived cyclic organic compounds, libraries and conjugates, as well as processes for making such are described, it is to be understood that this invention is not limited to the particular peptoids, cyclic and heterocyclic compounds and their substituents described herein as such compounds and methods may, of course, vary. It is also to be understood that the terminology used herein is for the purpose of describing particular embodiments only, and is not intended to be limiting since the scope of the present invention will be limited only by the appended claims.

The present invention includes a variety of different aspects, including novel cyclic or heterocyclic organic compounds and conjugates, libraries of cyclic compounds, processes for synthesizing such cyclic or heterocyclic compounds, libraries and conjugates, and processes for isolating from such libraries cyclic compounds of desired biological activity. Further, within each of these aspects of the invention, the present invention includes a large number of specific embodiments. The essence of the invention involves providing processing technology whereby those of ordinary skill in the art can use the information disclosed and described herein in order to produce and isolate molecules which mimic the biological activity of naturally-occurring molecules or synthetic biologically active molecules but which compounds of the invention have different chemical structures as compared to the natural molecule or synthetic molecule. The word "mimic" is used loosely, in that the molecules produced may have the same activity, greater activity, lesser activity, and/or block the effect of naturally-occurring biologically active molecules or biologically active synthetic molecules.

Throughout this description and the appended claims, it must be noted that the singular forms "a", "an" and "the" include plural referents unless the context clearly dictates otherwise. Thus, for example, reference to "a cyclic organic compound" includes mixtures of such cyclic organic compounds, reference to "reactive starting compound" includes reference to mixtures of such reactive starting compounds, and reference to "the method of synthesis" includes a plurality of such methods which will occur to those of ordinary skill in the art upon reading this disclosure.

All publications mentioned herein are incorporated herein by reference for the purpose of disclosing and describing features of the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

A number of terms are defined and used throughout the specification with the following definitions provided for convenience.

Oligomer

The term "oligomer" includes polymers such as poly NSGs, produced by the process of the invention, including homopolymers, copolymers and interpolymers of any length. More specifically, oligomers may be comprised of a single repeating monomer, two alternating monomer units, two or more monomer units randomly and/or deliberately spaced relative to each other. Regardless of the type of poly amide produced, the poly amide of the invention is produced by the same general procedure which includes repeating a two-step cycle (described below in detail) wherein a new monomer unit is added in each cycle until an oligomer of desired length is obtained. The oligomer is preferably 2–100 monomers, more preferably 2–50, or 2–20, and most preferably 2–6 monomers.

Acyl Submonomer

The term "acyl submonomer" refers to an acylating reagent used in the method of the invention. Acyl submonomers comprise a reactive carbonyl or carbonyl equivalent, and a leaving group which may be displaced in a nucleophilic displacement by an amine. "Carbonyl or carbonyl equivalent" includes, without limitation, carboxylic acids, esters, amides, anhydrides, acyl halides, and isocyanates (in the synthesis of polycarbamates of the invention). Esters and amides used will generally be "reactive" forms., e.g., DIC adducts and the like. The acyl submonomer may further comprise a side chain. Suitable acyl submonomers include, without limitation, bromoacetic acid, 3-bromopropionic acid, 2-bromopropionic acid, 2-bromoethylisocyanate, 2-bromoethylchloroformate, 6-phenyl-3-bromohexanoic acid, 4-bromomethyl-benzoic acid, 4-bromomethyl-2-methoxybenzoic acid, 5-bromomethyl-pyridine-2-carboxylic acid, and the like.

Amino Submonomer

The term "amino submonomer" refers to a compound containing an amino group capable of effecting a nucleophilic displacement of the leaving group in an acyl submonomer. The amino group may be primary, secondary, or tertiary. Addition of tertiary amines results in quaternary ammonium salts, and are preferably used as chain terminators (i.e., no further acylation of the oligomer is possible).

Presently preferred amino submonomers are primary amines and hydrazides, although amides, carbamates, ureas, carbazides, carbazates, semicarbazides, and the like are also suitable.

Sidechain

The term "sidechain" refers to a group attached to the polyamide backbone of a compound of the invention, at either a nitrogen or carbon atom. Sidechains may be H, hydroxy, $R_a$, —$OR_a$, —$NR_aR_b$, —$SO_{1,2,3,4}R_a$, —$C(O)R_a$, —$C(O)OR_a$, —$OC(O)R_a$, —$OC(O)OR_a$, —$NR_bC(O)R_a$, —$C(O)NR_aR_b$, —$OC(O)NR_aR_b$, —$NR_cC(O)NR_aR_b$, —$NR_bC(O)OR_a$, —$R_a$—O—$R_b$, —$R_a$—$NR_bR_c$, —$R_a$—S—$R_b$, —$R_a$—S(O)—$R_b$, —$R_a$—$S(O)_2$—$R_b$, —$OR_a$—O—$R_b$, —$NR_aR_b$—O—$R_c$, —$SO_{1,2,3,4}R_a$—O—$R_b$, —$C(O)R_a$—O—$R_b$, —$C(O)OR_a$—O—$R_b$, —$OC(O)R_a$—O—$R_b$, —$OC(O)OR_a$—O—$R_b$, —$NR_bC(O)R_a$—O—$R_c$, —$C(O)NR_aR_b$—O—$R_c$, —$OC(O)NR_aR_b$—O—$R_c$, —$NR_cC(O)NR_aR_b$—O—$R_c$, —$NR_bC(O)OR_a$—O—$R_c$, —$OR_a$—S—$R_b$, —$NR_aR_b$—S—$R_c$, —$SO_{1,2,3,4}R_a$—S—$R_b$, —$C(O)R_a$—S—$R_b$, —$C(O)OR_a$—S—$R_b$, —$OC(O)R_a$—S—$R_b$, —$OC(O)OR_a$—S—$R_b$, —$NR_bC(O)R_a$—S—$R_c$, —$C(O)NR_aR_b$—S—$R_c$, —$OC(O)NR_aR_b$—S—$R_c$, —$NR_cC(O)NR_aR_b$—S—$R_d$, —$NR_bC(O)OR_a$—S—$R_c$, —$OR_a$—$NR_bR_d$, —$NR_aR_b$—$NR_cR_d$, —$SO_{1,2,3,4}R_a$—$NR_bR_d$, —$C(O)R_a$—$NR_bR_d$, —$C(O)OR_a$—$NR_bR_d$, —$OC(O)R_a$—N—$R_bR_d$, —$OC(O)OR_a$—$NR_bR_d$, —$NR_bC(O)R_a$—$NR_cR_d$, —$C(O)NR_aR_b$—$NR_cR_d$, —$OC(O)NR_aR_b$—$NR_cR_d$, —$NR_cC(O)NR_aR_b$—$NHR_d$, —$NR_bC(O)OR_a$—$NR_cR_d$; where $R_a$, $R_b$, $R_c$ and $R_d$ are each independently alkyl, alkenyl, alkynyl, aryl, aralkyl, aralkenyl or aralkynyl;

where $R_a$, $R_b$, $R_c$ and $R_d$ are each substituted with 0–6 halo, $NO_2$, —OH, lower alkyl, —SH, —$SO_3$, —$NH_2$, lower acyl, lower acyloxy, lower alkylamino, lower dialkylamino, trihalomethyl, —CN, lower alkylthio, lower alkylsufinyl, or lower alkylsulfonyl, and where a, b, c, d are independently integers from 1 to 100.

Poly Amides

The term "poly amide" is used herein to describe oligomers of the invention as described above, which oligomers are not restricted to poly (N-substituted glycines) as described below. The poly amide compounds of the invention are produced by repeating the two-step cycle which is shown within Reaction Scheme 1. When the substituents on the carbon atom alpha to a carbonyl of the poly amide chain are always hydrogen, the resulting polymer is a poly (N-substituted glycine), whereas when the substituent on the α-carbon is a moiety other than hydrogen, the resulting compound is an N-substituted poly amide. N-substituted poly amide includes poly carbamates as further described herein. The term "peptoid" is used herein to describe an N-substituted poly amide of the invention. The term "peptoid backbone" is used herein to describe the chain of covalently linked atoms forming the amide bonds and linking one submonomer to the next submonomer.

Poly (N-substituted glycines)

The terms poly (N-substituted glycines), oligo (N-substituted) glycines, and poly NSGs are used interchangeably herein and are produced using the methodology of the present invention. Poly NSGs are not peptides, i.e., they are not composed of naturally-occurring amino acids linked in peptide bonds. However, they may be designed so as to have structural features (e.g., reactive sites) which are closely related to naturally occurring peptides and proteins, and as such are useful as potential therapeutic agents and/or as binding sites on assays. The poly NSGs disclosed herein can be designed so as to have a wide variety of side-chain substituents—including substituents normally found on natural amino acids and others not naturally occurring. For example, the invention makes it possible to synthesize compounds having side chains which resemble pharmacophores of known drugs, e.g., phenoxyphenyl, 2-adamantyl, and the like.

Sub-monomer

The term "sub-monomer" refers to an organic reactant used in the method of the invention which is added to the substrate-bound material in a step of the invention. An "acyl sub-monomer" of the invention (the first sub-monomer of Scheme 1.A) is an acylating agent comprising a leaving group capable of nucleophilic displacement by any amino group, e.g., —$NH_2$, —NRH or —$NR_2$. An "amino sub-monomer" (second sub-monomer of Scheme 1.A, for example) is a displacing agent reactant comprising an —$NH_2$ group. In one aspect of the invention, two submonomers react to form a monomer unit in a cycle of the invention, and repeating the cycle allows for the production of poly NSGs.

In another aspect of the invention, submonomers are added sequentially to a solid support resin or peptoid-derivatized solid support resin to form a backbone which is subsequently cyclized. In the preparation of a peptoid backbone for cyclization, the stepwise addition of submonomers introduces side chains and ring substituents to the final product.

Details of sub-monomer synthesis are described herein, in our parent U.S. application Ser. No. 07/950,853 now abandoned, and in our publication R. Zuckermann et al., *J. Am. Chem. Soc.* (1992) 114:10646–7, all of which are incorporated herein by reference.

Molecular moiety

The term "molecular moiety" encompasses any atom or group of atoms attachable to a nitrogen atom or a carbon atom of the main-oligomer chain, thereby forming a side-chain off of the main chain of the oligomer, e.g., in $CH_3(R^1)NC(O)CH(R^2)CH^3$, in which $R^1$ is a molecular moiety attachable to the nitrogen atom of the oligomer main-chain, thereby forming a side-chain attached to the nitrogen atom, and $R_2$ is a molecular moiety attachable to the carbon atom of the oligomer main-chain, thereby forming a side-chain attached to the carbon atom. Thus, it is readily apparent to those of skill in the art of polypeptide or polyamide synthesis that a wide variety of molecular moieties can be used, including but not limited to hydrogen, and hydrocarbyl moieties such as alkyl, aryl and arylalkyl moieties. In the novel poly (N-substituted glycine) of Formula I below, at least one of the molecular moieties attachable to nitrogen is other than H (i.e. forms a side-chain substituted on the nitrogen).

Organic compound

"Organic compound" means a molecule comprised of carbon, hydrogen, nitrogen, oxygen, sulphur, and phosphorous atoms. As used herein, an organic compound can be a cyclic or acyclic compound formed entirely of carbon and hydrogen, or it can contain one or more heteroatoms including oxygen, nitrogen, sulphur, and phosphorous atoms.

Cyclic organic compound

"Cyclic organic compound" means an organic compound which contains at least one cyclic structure derived from cyclization of the peptoid backbone. The cyclic structure can be a hydrocarbon comprised of carbon and hydrogen and can be aliphatic or aromatic. The cyclic structure may be a heterocycle containing at least one heteroatom in the cyclic backbone. The heterocyclic structure may be saturated or unsaturated. Cyclic structures may be fused or separated within a cyclic compound.

Hydrocarbon, hydrocarbyl, hydrocarbylene

"Hydrocarbon" describes a compound, whereas "hydrocarbyl" and "hydrocarbylene" describe radicals with one or two hydrogens removed respectively. Each are composed entirely of hydrogen and carbon atoms, and may be saturated or unsaturated, aliphatic, alicyclic or aromatic. When rings are included the structure usually includes one, two, three, or more rings, which rings may be fused or bridged or spiro-fused.

Substituent, substituted, substitutable position, and derivative

Substituent describes an atom or radical which is part of a first molecule in that it replaces another atom or radical of the first molecule. When a molecule is substituted, it is a derivative of a molecule bearing one or more substituents. Useful substituents in any of the sub-monomers of the invention include halo, alkyl, alkoxy, alkylthio, haloalkyl, haloalkoxy, halothio, disubstituted amino, and the like, which replace an atom such as hydrogen attached to a nitrogen or carbon. A substitutable position is the attachment site of the replaced atom or radical of the first molecule.

Purine or pyrimidine base

A "purine or pyrimidine base" includes the natural nucleoside bases, such as A, T, G, C or U, and also derivatives thereof including those purines and pyrimidines substituted by one or more of alkyl, caboxyalkyl, amino, hydroxyl, halogen (i.e. fluoro, chloro, bromo, or iodo), thiol, or alkylthiol wherein the alkyl group contains from 1 to about 6 carbon atoms. Non-limiting examples of purines and pyrimidines include 2,6-diaminopurine, 5-fluorouracil, xanthine, hypoxanthine, 8-bromoguanine, 8-chloroguanine, 8-aminoguanine, 8-hydroxyguanine, 8-methylguanine, 8-thioguanine, 2-aminopurine, 5-ethylcytosine, 5-methylcyosine, 5-bromouracil, 5-ethyluracil, 5-iodouracil, 5-propyluracil, 2-methyladenine, methylthioadenine, N,N-diemethyladenine, 8-bromoadenine, 8-hydroxyadenine, 6-hydroxyaminopurine, 6-thiopurine, 4-(6-aminohexyl/cytosine) and the like.

Leaving group

"Leaving group" means a moiety capable of nucleophilic displacement by an amine, e.g., —$NH_2$. Any leaving group can be used here provided it is readily removed by nucleophilic displacement. Non-limiting examples of leaving groups useful in the invention include halo, such as bromo, chloro, iodo, O-tosyl, O-triflyl, O-mesyl and the like.

Substrate

A "substrate" or "solid support" is a conventional solid support material used in peptide synthesis. Non-limiting examples of such substrates or supports include a variety of solid supports and connectors to the solid supports such as those which are photocleavable, DKP-forming linkers (DKP is diketopiperazine; see, e.g., WO90 09395 incorporated herein by reference), TFA cleavable, HF cleavable, fluoride ion cleavable, reductively cleavable and base-labile linkers. A solid support comprises a plurality of solid support particles, such as beads, which can be split into portions or "subamounts" for separate reactions and recombined as desired. The symbol, "P--", in reaction schemes represents a solid support (such as polystyrene beads) to which peptoid oligomers are covalently attached. In general, a resin in the form of an electron donating group such as —$NH_2$ or —OH is derivatized onto the solid support surface to provide suitable reactive sites.

Protecting group

"Protecting group" means any group capable of preventing the atom to which it is attached, usually oxygen or nitrogen, from participating in an undesired reaction or bonding, usually in a synthesis reaction. Protecting groups are also known to prevent reaction or bonding of carboxylic acids, thiols, and the like. Such groups and their preparation and introduction are conventional in the art and include salts, esters and the like.

Electron withdrawing group

"Electron withdrawing group (EWG)" means a moiety covalently attached to a reactant which EWG is capable of activating nucleophilic addition of a portion of a polyamide backbone to the reactant. Non-limiting examples of electron withdrawing groups useful in the invention include nitro, carbonyl, cyano, sulfone, and the like.

Electron donating group

"Electron donating group (EDG)" means a moiety covalently attached to a reactant with EDG is capable of increasing electron density in other parts of the reactant. Non-limiting examples of electron donating groups useful in the invention include alkyl, amine, hydroxyl, alkoxy, and the like.

Driving a reaction to substantial completion

"Driving the reaction to substantial completion" means performing a reaction under conditions in which the concentrations of reactants, catalysts, temperature, and other conditions are appropriate to cause greater than 80%, preferably greater than 90%, more preferably greater than 95% of the solid-support bound intermediate compound is reacted.

Retrievable amount

"Retrievable amount" means an amount of a compound in a mixture which compound is present in a concentration such that a recoverable amount is separable from the other components of the mixture by techniques available in the art at the time of separation. Preferably, at least 50 pmol, more preferably 100 pmol of compound is present in the mixture when the components of the mixture are present in approximately equal molar amounts.

Analyzable amount

"Analyzable amount" means an amount of a compound that is present in a mixture such that the compound can be detected and identified in the mixture. Preferably at least approximately 10 pmol, more preferably 50 pmol of compound is present in the mixture when the components of the mixture are present in approximately equal molar amounts.

Combinatorial library

"Library" or "combinatorial library" or "peptoid-derived library" and the like are used interchangeably herein to mean a mixture of organic compounds synthesized on a solid support from submonomer starting materials. Where the compounds of the library are peptoids, the peptoids can be cyclic or acyclic. The library will contain 10 or more, preferably 100 or more, more preferably 1,000 or more, and even more preferably 10,000 or more organic molecules which are different from each other (i.e. 10 different molecules and not 10 copies of the same molecule). Each of the different molecules will be present in an amount such that its presence can be determined by some means, e.g. can be isolated, analyzed, or detected with a receptor or suitable probe. The actual amount of each different molecule needed so that its presence can be determined will vary due to the actual procedure used and may change as the technologies for isolation, detection and analysis advance. When the molecules are present in substantially equal molar amounts an amount of 100 picomoles (pmol) or more can be detected.

The term "pool" means a combining of derivatized or underivatized solid support particles to form a mixture. Pooled materials contain intermediates in the preparation of a peptoid library or final products. A portion of a pool is a "subamount".

Method for Synthesis of Monomers from Sub-monomers

In the basic method of the invention, each N-substituted monomer is synthesized directly on a solid substrate (support) from two reactants which are referred to herein as sub-monomers.

Each monomer is produced by a synthesis cycle comprising two steps. The first step comprises acylation of a substrate-bound amine carried out using a first sub-monomer acylating agent comprising a leaving group capable of nucleophilic displacement by an amine e.g., —NH$_2$, such as a haloacetic acid. The second step of the monomer synthesis cycle comprises the introduction of a side-chain by nucleophilic displacement of the leaving group, such as halogen or tosyl, by providing a sufficient amount, usually an excess, of a second sub-monomer displacing agent comprising an amine, e.g., —NH$_2$ group, such as a primary amine. This two-step process is shown within Reaction Scheme 1.A.

However, it should be noted that Reaction Scheme 1.A can also be carried out in reverse, as is shown within Reaction Scheme 1.B. More specifically, it is possible to begin the reaction not with the "substrate-bound amine" as per Reaction Scheme 1.A, but to begin the reaction with the acylating agent sub-monomer bound to the substrate. Accordingly, the carboxylic acid group extends from the surface of the substrate and is reacted, in the first step, with an amine. At this point, an amine group now extends outward from the substrate, and is subjected to acylation using a sub-monomer acylating agent as per the first step of Reaction Scheme 1.A described above.

The basic two-step process of Reaction Scheme 1 (A or B) produces a monomer unit and can be repeated to produce polymers (as per formula V below) of any desired length as per monomers of structure I below. The variables shown in the structures can be changed to obtain a desired result. Further, the basic sub-monomer structures can also be changed as below to obtain different monomer/polymer structures as in structures II, III and IV.

SCHEME 1.A
Solid-phase assembly of an N-substituted oligomers from two sub-monomers

STEP 1A

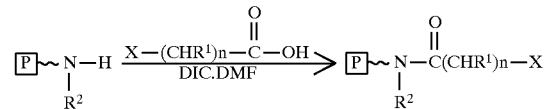

STEP 2A

SCHEME 1.B
Solid-phase assembly of an N-substituted oligomers from two sub-monomers

STEP 1B

-continued
SCHEME 1.B
Solid-phase assembly of an N-substituted
oligomers from two sub-monomers

STEP 2B

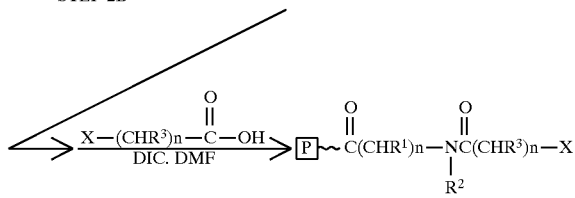

In each of the above, "P" is the solid phase surface, each $R^1$ and $R^3$ are, independently, any molecular moiety attached to a carbon atom, $R^2$ and $R^4$ are, independently, any molecular moiety attached to a nitrogen atom, and n is an integer of from 1–10 (preferably 1 or 2). Any of $R^1$, $R^2$, $R^3$ and $R^4$ may include the twenty different side-chain moieties attached to the twenty natural amino acids, i.e., —H of glycine; —$CH_3$ of alanine; —$CH(CH_3)_2$ of valine; —$CH_2CH(CH_3)_2$ of leucine; —$CH(CH_3)CH_2CH_3$ of isoleucine; —$CH_2OH$ of serine; —$CHOHCH_3$ of threonine; —$CH_2SH$ of cysteine; —$CH_2CH_2SCH_3$ of methionine; —$CH_2$—(phenyl) of phenylalanine; —$CH_2$—(phenyl)—OH of tyrosine; —$CH_2$—(indole group) of tryptophan; —$CH_2COO^-$ of aspartic acid; —$CH_2C(O)$ ($NH_2$) of asparagine; —$CH_2CH_2COO^-$ of glutamic acid; —$CH_2CH_2C(O)NH_2$ of glutamine; —$CH_2CH_2CH_2$—N—(H)—$C(NH_2)^+$—$NH_2$ of arginine; —$CH_2$—(imidazole)$^+$ group of histidine; and —$CH_2(CH_2)_3NH_3^+$ of lysine.

Reaction Scheme 1 (A and B) includes some abbreviations which refer to reagents used in connection with the invention. For example, DMSO refers to dimethylsulfoxide, DIC refers to N,N-diisopropyl carbodiimide, and DMF refers to N,N-dimethylformamide.

Each step of the two-step method of the invention is usually conducted at about ambient temperature of 20° C. and pressure of 1 atmosphere. However, the reaction can also be carried out over a wide range of temperatures between about 5° C. to about 80° C., and varies depending on the solvent used. Depending on the temperature, the time of the two-step Reaction Scheme 1 can vary within the range of about 5 minutes to about 24 hours. The above temperature, times and reagents are applicable to carrying out the reaction at atmospheric pressure. Other pressures may be employed.

When the sub-monomers are liquids, each step can be conducted in the absence of a solvent. However, an inert solvent is used when the sub-monomer is a solid or to facilitate the reaction. Suitable inert solvents include ethers, such as dioxane, blocked amides, such as dimethylformamide, sulfoxides, such as dimethylsulfoxide, and the like.

The ratio of the reactants can vary. However, for highest yields it is desirable to provide an excess of sub-monomer of from about 1.01 to 10 times the amount of substrate-bound material, preferably, from about 1.5 to 5 times the amount of substrate-bound material.

In the two-step cycle of the invention shown in Scheme 1, the secondary amine bound to the substrate is preferably an amine prepared from a primary amine, and is bound (using conventional methodology) to a substrate support base surface or solid phase (represented by the letter "P").

The first step of the cycle is the acylation which is carried out by reacting a first sub-monomer comprising an acylating agent comprising a leaving group capable of nucleophilic displacement by an amine, e.g., —$NH_2$, such as a haloacetic acid, and especially a bromoacetic acid representatively illustrated in Scheme 1 with the substrate-bound secondary amine to obtain an acylated amine.

The second step of the two-step monomer synthesis method of the invention is where the backbone nitrogen and side-chain or $R^2$ group of the monomer unit is added. In the second step, the acylated amine is reacted with a sufficient amount of a second sub-monomer comprising an —$NH_2$ group, such as a primary amine or secondary amine, alkoxyamine, semicarbazide, carbazate, acyl hydrazide or the like, which includes the $R^2$ group (i.e., the side-chain group), which is to be added at this monomer position in the oligomer. The reaction of the second sub-monomer is preferably accomplished by adding a sufficient amount, usually an excess, of the second sub-monomer which causes a nucleophilic displacement of the leaving group, which is representatively illustrated as the bromine shown in Scheme 1.

Preparation of cyclic peptoids via the Sub-monomer Method

Cyclic peptoids have been prepared by the sub-monomer method. A general Reaction Scheme (Scheme 2) for such is shown below.

Scheme 2
SUB-MONOMER CYCLIZATION

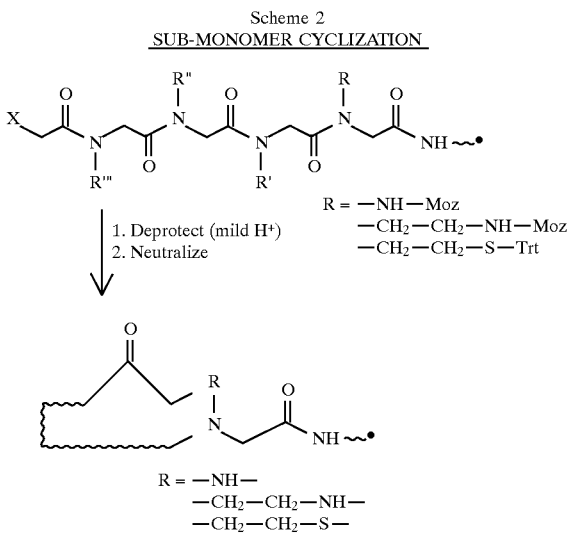

The key reaction to effect cyclization is the displacement of an N-terminal bromoacetamide with a side-chain nucleophile, generating a "head-to-side-chain" cyclic structure on the solid support. The side-chain nucleophile is incorporated at the desired portion of the oligomer via standard sub-monomer conditions. Typical nucleophiles are thiols and amines which can be protected. Preferred sub-monomers for this purpose are Moz—NH—$CH_2$—$CH_2$—$NH_2$, Alloc—NH—$CH_2$—$CH_2$—$NH_2$ and Trt—S—$CH_2$—$CH_2$—$NH_2$. The oligomer is then elaborated until the desired length and is terminated with a bromoacetamide group. The side-chain nucleophile is then selectively deprotected and allowed by cyclize.

Specific examples of cyclic peptoids produced and the percentage yield obtained are put forth below. Examples of cyclic compounds having specific ring structures and which are derived from peptoids are provided herein in Examples 19–31.

TRIMERS

| R''' | R'' | R' | MH+ | Yield (%) |
|---|---|---|---|---|
| CH3O~ | [benzyl] | CH3O~ | 536 | 15 |
| [cyclopentyl] | [cyclopentyl] | [cyclopentyl] | 575 | 29 |
| [benzyl] | [benzyl] | [benzyl] | 600 | 25 |
| HO-[phenethyl] | [biphenyl] | [phenethyl] | 705 | 20 |
| [diphenylmethyl] | [diphenylmethyl] | [diphenylmethyl] | 870 | 45 |

Carbamate Synthesis via Submonomer Method

As an extension of the NSG-peptoid approach to combinatorial library synthesis, additional types of oligomeric frameworks that can be prepared using the submonomer method include oligo N-substituted carbamates (NSCs), compound 1 of Scheme 3. Like NSG-peptoids, NSCs can be prepared on the solid support in two steps using inexpensive, commercially available starting materials. The backbone carbons are derived from 2-bromoethylchloroformate (BECF); the backbone nitrogen and the side chain atoms are derived from commercially available primary amines.

The NSC backbone allows for increased structural diversity of NSC libraries. In an extended structure, the side chains of NSCs are spaced farther apart than in peptides or NSG-peptoids. This can be particularly useful in receptor systems where the active pharmacophores need to bind to distal receptor sites. Like NSG-peptoids, carbamate bonds can be cis or trans about the carbamate bond adding to the structural diversity of NSCs. The conformation of the NSC backbone is less restrained than NSG-peptoids due to the absence of hydrogen bonds between amide and carbonyl moieties in the backbone. Also, because the synthesis of NSCs and NSG-peptoids is modular using the submonomer method, carbamate modules can be incorporated into peptides, peptoids, or other solid-phase libraries. A general structure of oligo N-substituted carbamates that can be prepared by the method of the invention is shown below.

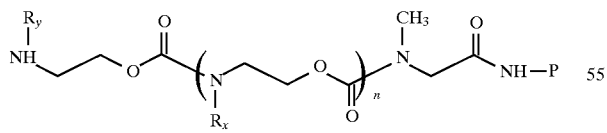

Photolithographic Method

The method of the invention may also be applied to the optically-addressed spatial array technique described by Pirrung et al., U.S. Pat. No. 5,143,854, incorporated herein by reference. This technique uses analogs of semiconductor mask technology to form oligomeric compounds on the surface of any substrate in an array. Photolabile protecting groups are used to protect surface-bound compounds from reaction. To add another monomer to a particular compound (i.e. a particular region in the array), one deprotects the compounds in that region by illuminating or irradiating only that region. This is accomplished using, e.g., a carefully aimed light source or laser, or a mask which permits illumination only of the desired area(s). Using semiconductor-type photolithographic techniques, this method may be scaled down to extremely small sizes. Suitable photolabile protecting groups include, without limitation, 6-nitroveratryloxycarbonyl (NVOC: 3,4-dimethoxy-6-nitrobenzyloxycarbonyl), 2-nitrobenzyloxycarbonyl, α,α-dimethyl-dimethoxybenzyloxycarbonyl (DDC), 5-bromo-7-nitroindolinyl, o-hydroxy-α-methylcinnamoyl, and 2-oxymethyleneanthraquinone.

The Pirrung et al. method is adapted to the method of the invention by using photolabile protecting groups to protect oligomers ending in amino sub-monomers, synthesized in a spatially defined array. For example, acyl sub-monomers are coupled to a flat substrate in an array of reaction zones (e.g., 8×12, 20×20, 100×100, etc.). A first amino sub-monomer is then coupled to all acyl sub-monomers, and is then protected, e.g. with NVOC. Zones are selected for coupling the next monomer (acyl sub-monomer and amino sub-monomer), and the remaining zones masked to prevent reaction. The selected zones are deprotected by illumination or irradiation, and are then reacted with the next acyl sub-monomer followed by the next amino sub-monomer. The terminal amino sub-monomer is then protected again with NVOC (unless it is to be further modified in the next round of synthesis), and the zones selected for the next monomer to be coupled. This cycle is repeated until all oligomers have been synthesized. The compounds may then be cleaved from the support, or may be assayed in situ (typically by assaying ability to bind fluorescently-labeled antibodies or ligands).

Halomethylbenzoic acids

In one embodiment of the invention, the first sub-monomer is a halogenated organic acid, such as bromoacetic acid, chloromethylbenzoic acid and the like. The sub-monomer synthesis can accommodate the incorporation of several different halo-acids (e.g., bromoacetic acid and chloromethylbenzoic acid) in the same polymer chain to generate hybrid backbones. Furthermore, other derivatized aromatic acids could be used as well.

Acyl hydrazides

Acyl hydrazides, carbazates, semicarbazides and related compounds of the formula

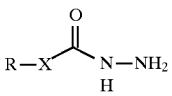

wherein X is a bond, —O—, —N—, or a hydrocarbylene group, can be used instead of amines as the second sub-monomer displacing agent in the method of the invention.

Oligomers generated by the sub-monomer synthesis using acyl hydrazides will have a hydrogen bond donor and an acceptor group displayed in each side-chain. This may allow stabilization of secondary and tertiary structural motifs.

Acyl hydrazides are readily prepared from carboxylic acids/esters and hydrazine:

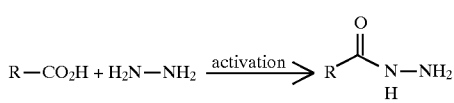

Similarly, carbazates and semicarbazides can be prepared from alcohols or amines, p-nitrophenyl chloroformate and hydrazine:

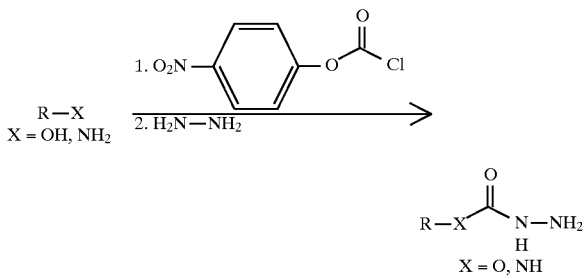

In this way, hydrazine can be viewed as an "adapter molecule" that can link oligo (N-substituted) polymer backbones with carboxylic acids, alcohols and amines. Thus, the sub-monomer synthesis can be expanded to include not only amine-based diversity, but alcohol and carboxylic acid diversity as well. A very large number of alcohols and carboxylic acids are commercially available and others can be readily produced by known techniques.

The displacing agent can have a wide range of nucleophilicity, steric hinderance, volatility, side-chain protecting groups (when present), solubility and the like.

Any conventional amine (e.g., primary amine) can be used that does not contain groups that would otherwise interfere with the reaction steps. This includes amines that have groups that are in a protected form, which protection may be subsequently removed. Non-limiting examples of preferred amines include 4-(2-aminoethyl)morpholine, aniline, benzylamine, cyclopentylamine, N-Boc-1,6-diaminohexane, glycine-OtBu, hexylamine, 2-methoxyethylamine, methylamine, tyramine and the like.

In another embodiment of the invention, the second sub-monomer is an acyl hydrazide. A benefit of such sub-monomers can be to stabilize the secondary and tertiary motifs by providing a hydrogen bond donor and an acceptor group in each side-chain. Acyl hydrazides are readily prepared from carboxylic acids and esters and hydrazine using conventional techniques.

Similarly, carbazates and semicarbazides can be prepared conventionally, for example from alcohols or amines, p-nitrophenyl chloroformate and hydrazine.

Method of Synthesizing Oligomers

The basic two-step method of Scheme 1 yields a monomer unit. Another and important embodiment of the present invention is directed to the oligomer synthesis method comprising repeating the two-step cycle of acylation and displacement. A particularly preferred embodiment of the invention is a method of producing oligomers, such as poly NSGs.

Steps 1 and 2 can be repeated any desired number of cycles to obtain the desired number of monomer units. Within each of the steps of each cycle, the variables $R^1$ and $R^4$ shown within Scheme 1.A can be varied in order to produce different side-chain moieties. The terminal N is shown connected to $R^4$ and H here. However, this is done to allow other cycles to add monomer units. The actual terminal —N containing group can be capped by providing alkyl and/or acyl groups for $R^3$ and/or $R^4$, as defined for the poly NSGs of Formula V below. The variables $R^2$ and $R^3$ can be changed in each step of each cycle in order to obtain any desirable side-chain moieties and resulting oligomer. Accordingly, it can be seen that both Reaction Scheme 1.A and 1.B can be carried out to produce any desired oligomer with any desired side-chain groups and with any desired ending moiety.

Different R groups are correctly positioned in the molecule by using the correct second sub-monomer in step 2 of each cycle. The resulting poly NSG consists of the desired sequence of monomer units.

Producing Oligomer Mixtures

It is also possible to use the invention to produce mixtures of poly amides which mixtures have known amounts of each poly amide by reacting (in step 2) mixtures of second sub-monomers with the acylated amine of step 1. By knowing or calculating the reaction rate constant for the reaction of each second sub-monomer with the acylated amine, it is possible to calculate the proportional amounts of each product poly NSG which results and precisely determine the composition of the resulting mixture of poly NSGs. Such methodology is described as regards producing mixtures of conventional peptides by reacting conventional amino acids based on reaction rate constants in U.S. Pat. No. 5,225,533 issued Jul. 6, 1993.

Further, the methods of the present invention could be applied in other methods such as that of Houghten, R. A., *Proc Natl Acad Sci USA* (1985) 82:5131–5135, which teaches a modification of the Merrifield method using individual polyethylene bags. In the general Merrifield method, the C-terminal amino acid of the desired peptide is attached to a solid support, and the peptide chain is formed by sequentially adding amino acid residues, thus extending the chain to the N-terminus. The additions are carried out in sequential steps involving deprotection, attachment of the next amino acid residue in protected form, deprotection of the peptide, attachment of the next protected residue, and so forth.

In the Houghten method, individual polyethylene bags containing C-terminal amino acids bound to solid support can be mixed and matched through the sequential attachment procedures so that; for example, twenty bags containing different C-terminal residues attached to the support can be simultaneously deprotected and treated with the same protected amino acid residue to be next attached, and then recovered and treated uniformly or differently, as desired. The resulting product of this procedure is a series of polyethylene bags each containing a different peptide sequence. Although each bag contains many peptides, all of the peptides in any one bag are the same. The peptides in each bag can then be recovered and individually tested, e.g. via biological assays.

The present invention can be used with other methods in order to produce mixtures of poly NSGs which include predetermined amounts of the different poly NSGs in the mixtures, including equal molar amounts of each poly NSG in the mixture. The method can be used such that each poly NSG is present in the mixture in an amount such that it can be retrieved and analyzed. Such mixture of poly NSGs can be generated by synthetic algorithms that involve splitting pools of solid support beads into equal portions, coupling a unique NSG to each portion and then mixing the portions (c.f. Furka, A., et al. (1991) *Int. J. Pep. Pro. Res.*, 37:487–493; Lam, K. et al. (1991) *Nature*, 354:82–84; Houghten, R. et al. (1991) *Nature*, 354:84–86; Zuckermann, R. et al. (1991) Patent Appl. PCT WO 91/17823; Zuckermann, R. et al. (1992) *Proc. Natl. Acad. Sci.* 89:4505–4509, incorporated herein by reference).

The methods of the present invention can also be used in an alternative method devised by Geysen, H. M., et al., *Proc Natl Acad Sci USA* (1984) 81:3998–4002. See Pat. Nos. 4,833,092, 5,194,392, WO86/06487 and WO86/00991. This method is a modification of the Merrifield system wherein the C-terminal amino acid residues are bound to solid supports in the form of polyethylene pins and the pins treated individually or collectively in sequence to attach the remaining amino acid residues. Without removing the peptides from support, these peptides can then efficiently be assessed effectively and individually for the desired activity, e.g. interaction with a given antibody or receptor. The Geysen procedure results in considerable gains in efficiency of both the synthesis and testing procedures, while nevertheless producing individual different peptides. The peptides can also be cleaved from the pins and assayed in solution.

Automated Synthesis

The preparation of NSG oligomers by reacting sub-monomers can be adapted to an automated synthesizer (see Zuckermann, R. N., Kerr, J. M., Siani, M. & Banville, S., *Int. J. Peptide Protein Res.* (1992), Vol. 40 pp. 497–506 and U.S. Pat. No. 5,252,296). Each cycle of monomer addition (as is shown in Scheme 1) comprising the two steps: (1) an acylation step, and (2) a displacement step; with the proviso that there is no N,α-deprotection step.

Acylation of a secondary amine can be difficult, especially when coupling an acyl sub-monomer. Accordingly, the acylation can be facilitated by the use of the acylating agent in the presence of a carboxylate activator, such as a carbodiimide, as a potent acylating agent mixture. Accordingly, it can be desirable for the first step of acylation of a substrate-bound secondary amine with a first sub-monomer, such as a haloacetic acid (Lindner, W., Robey, F. A., *Int. J. Peptide Protein Res.*, 30, 794–800 (1987); Robey, F. A., Fields, R. L., *Anal. Biochem.*, 177, 373–377 (1989); Wetzel, R., Halualani, R., Stults, J. T., Quan, C., *Bioconjugate Chem.*, 1, 114–122 (1990)); Fisther, E. *Ber. Dtsch. Chem. Ges.* (1904), 37:3062–3071 uses a suitable carboxylate activation method. A carbodiimide, haloacetyl halide or other suitable activator can also be used.

The second step in the two-step method of the invention introduces the side-chain by nucleophilic displacement of the leaving group, which is generally a halogen (as a substrate-bound α-haloacetamide) with an excess of a second sub-monomer comprising an amino group, e.g., an —$NH_2$, —NRH, —$NR_2$ group. The efficiency of the displacement is modulated by the choice of the leaving group, for example, in the case where the leaving group is a halo atom (e.g., I>Cl).

Protection of carboxyl, thiol, amino and other reactive groups on the side-chain is desirable to minimize undesired side reactions. However, the mild reactivity of some side-chain moieties toward displacement or acylation can allow their optimal use without protection (e.g., indole, imidazole, phenol).

Oligomers

By use of the novel method of the invention, as shown in Reaction Scheme 1 and described above, it is possible to produce a wide range of oligomers of the Formula I:

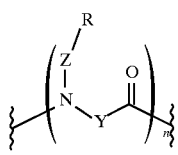

wherein
R is a sidechain as defined above;
Z is a bond, —O—, —NC(O)W—in which W—is a bond, —O—, or —N—;
Y is a hydrocarbylene group or Ar wherein Ar is selected from the group consisting of arylene, heteroarylene having 1–4 heteroatoms, cycloalkylene, cycloalkenylene, heterocycloalkylene having 1–4 heteroatoms, where Ar has from 1 to 3 rings, and said rings are joined by a bond or alkylene radical, or are fused, bridged, or spiro-fused. Ar may be substituted with 1–6 substituents selected from the group consisting of halo, nitro, lower alkyl, lower cycloalkyl, —OH, —$NR_aR_b$ where $R_a$ and $R_b$ are each independently —H or lower alkyl, —$OR_a$, —$C(O)R_a$, —$OC(O)R_a$, —$C(O)OR_a$, —$OC(O)OR_a$, —$(CH_2)_a$—$CX_1X_2X_3$ where n is 0–6 and $X_{1-3}$ are each independently H or halo, —$NC(O)R_a$, —$C(O)NR_aR_b$, —$OC(O)NR_aR_b$, or —$NC(O)NR_aR_b$; and
n is an integer of from 2 to 2000.

When chloromethylbenzoic acids are used in place of bromoacetic acid, the oligomer has the Formula II:

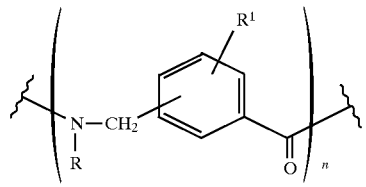

R and $R^1$ may be any moiety connectable to a nitrogen atom, but each is preferably, independently, a hydrocarbyl containing 1 to 30 carbon atoms.

The preferred method of synthesizing this oligomer is to modify the acylation step 1 to also include an activating agent, such as a meta- or para-chloromethylbenzoic acid anhydride. Thus, about 0.6M solution of p-chloromethylbenzoic acid is combined with a carboxylate activator, such as about 0.5 equivalents of diisopropylcarbodiimide, for about 30 minutes at room temperature. The precipitate (diisopropylurea) is then removed by filtration to yield the acylation solution. Acylation reactions are then conducted as previously described. The preactivation step is used due to the slower rate of activation of the benzoic acid moiety as compared to the acetic acid moiety.

The N-substituted oligomers of the invention can be varied by changing one or both of the reactants on Reaction Scheme 1. Specifically, the reaction can be carried out using acyl hydrazide, carbazate, semicarbazide or a related compound of the structure:

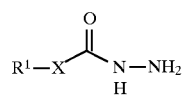

wherein X is —O—, —N—, or a bond and $R^1$ is as defined above in Reaction Scheme 1. When such reactants are used in Reaction Scheme 1, it results in N-substituted oligomers wherein the oligomers are represented by Formula III:

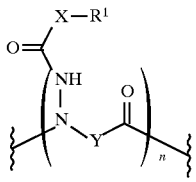

wherein

X is a bond, O, N, or a hydrocarbylene group; Y is a hydrocarbylene group or an arylene; and $R^1$ is as defined above in Reaction Scheme 1.

Alkoxyamines

When the second sub-monomer used to synthesize oligomer is an alkoxyamine, the oligomer can have the Formula IV

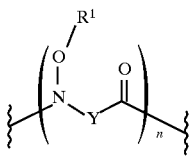

wherein Y is a hydrocarbylene group, such as methylene, or —$CH_2C_6H_4$— and $R^1$ is as defined above.

When carrying out Reaction Scheme 1 with an alkoxyamine, the alkoxyamine is used in the displacement reaction (step 2) as a 1.0–2.0M solution in DMSO.

The novel polyamide structures differ from polypeptides in that the side-chains are substituted on the nitrogen rather than (or in addition to) the α-carbon. One embodiment of the invention is directed to compounds having the Formula V

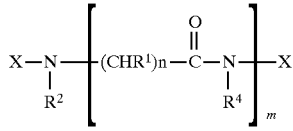

FORMULA V wherein $R^1$ and $R^4$ are each independently any moiety attachable to the nitrogen atom;

$R^2$ and $R^3$ are each independently any moiety attachable to the carbon atom, including —H or an alkyl moiety containing 1 to 6 carbon atoms, and are preferably —$CH_3$ and more preferably —H;

X are each, independently —$HNR^5$ wherein $R^5$ is as $R^1$ and X is preferably —$NH_2$, —OH, H and a straight or branched chain alkyl (1–6 carbons) or two lower alkyls, or X is —$OR^6$ wherein $R^6$ is —H or a lower alkyl (1–6 carbons);

m is an integer of from 1 to 2,000, preferably 2–100, more preferably 2–12, and most preferably 3–8; and n is an integer of from 1 to 10 and is preferably 1 or 2.

Non-limiting examples of useful moieties for $R^1$, $R^2$, $R^3$ and $R^4$ (in particular for $R^4$) include the side-chain moieties present on a naturally occurring amino acid, i.e., —H of glycine; —$CH_3$ of alanine; —$CH(CH_3)_2$ of valine; —$CH_2CH(CH_3)_2$ of leucine; —$CH(CH_3)CH_2CH_3$ of isoleucine; —$CH_2OH$ of serine; —$CHOHCH_3$ of threonine; —$CH_2SH$ of cysteine; —$CH_2CH_2SCH_3$ of methionine; —$CH_2$—(phenyl) of phenylalanine; —$CH_2$—(phenyl)—OH of tyrosine; —$CH_2$—(indole group) of tryptophan; —$CH_2COO^-$ of aspartic acid; —$CH_2C(O)(NH_2)$ of asparagine; —$CH_2CH_2COO^-$ of glutamic acid; —$CH_2CH_2C(O)NH_2$ of glutamine; —$CH_2CH_2CH_2$—N—(H)—$C(NH_2)^+$—$NH_2$ of arginine; —$CH_2$—(imidazole)$^+$ group of histidine; and —$CH_2(CH_2)_3NH_3^+$ of lysine. Other useful moieties for $R^1$–$R^4$ (and in particular $R^1$ and $R^3$) include alkyls containing 1–6 carbons (straight or branched chains); aryls, aralkyls, nucleoside bases and derivatives thereof, carbohydrates and lipids.

There are a number of well known modified forms of the common amino acids such as O-phosphoserine; O-phosphothreonine; O-phosphotyrosine; N-formylmethionine and glycinamide and the side-chains of these modified amino acids are also readily used as the R group on the compounds of Formulas V and VI.

Typical R-groups used include pharmacophores and natural amino acids and derivatives thereof. The resulting poly NSGs will be biologically active, e.g., mimic or block the activity of a naturally occurring peptide or non-peptide molecule which adheres to a natural receptor site.

Some compounds and groups of compounds are also important aspects of the invention. One preferred subclass is directed to compounds of Formula VI

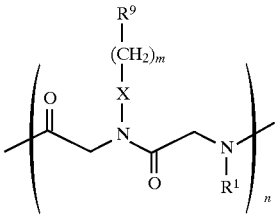

wherein $R^9$ is a heterocyclic capable of forming hydrogen bonds and base pairing with purine or pyrimidine bases, including a nucleoside base such as A, T, G, C or U or derivative thereof;

$R^1$ is defined above and preferably is —H or an alkyl moiety containing 1 to 6 carbons, more preferably —$CH_3$, most preferably —H;

m is an integer of from 1 to 5 and is preferably 2;

n is an integer of from 1 to 2,000; and

X is a bond, —O—, —NR— or O=C—O—.

Utility

The individual oligomers and mixtures of oligomers of the invention are useful in a variety of ways similar to that of conventional nitrogen-based oligomers, proteins, polyamides and polypeptide-like oligomers, for example, they can have one or more properties in binding to various moieties, including proteins, such as enzymes, receptors, antibodies and the like, nucleic acids, carbohydrates, lipids, they can react with enzymes to form products, or have other properties such as antigenic compounds for vaccines or diagnostic reagents, including as probes. The liquid oligomers of the invention can also find utility as functional fluids, including solvents, antifreeze, and the like. Solid oligomers of the invention can also find utility as additives for foodstuffs, as supports for diagnostic and other technical materials in commercial and research applications. Compounds as per the above formulas can also be used as enzyme inhibitors and in connection with affinity chromatography.

Compounds of Formula VI are useful in binding to DNA and RNA and as such can be used as probes and/or in antisense technology. Useful probes can be produced by synthesizing compounds of Formula VI, wherein $R^9$ is a nucleoside base, m is 2 and further wherein the monomer units of the compound have the purine or pyrimidine nucleoside bases positioned in a predetermined sequence designed so as to provide for hybridization of the polymer with an appropriate DNA or RNA target.

Compounds and mixtures of compounds produced by Reaction Scheme 1 include those encompassed by Formula I, II, III, IV, V, VI and VII. These compounds or mixtures thereof will, as indicated above, bind to a variety of receptors. Accordingly, such compounds or mixtures thereof can be bound to a support to provide useful assay devices.

Because the compounds of Formula VI are used as probes, it is preferable to attach a suitable label to the polymer. Suitable labels and the means of their attachment are known to those skilled in the art and include radioactive, fluorescent and enzyme labels and the like.

Polymers of Formula VI can also be used in antisense technology when the $R^9$ is a purine or pyrimidine base and the sequence of bases in the polymer is designed so as to hybridize to and interrupt the transcription or translation of appropriate DNA and RNA molecules which are known to be pathogenic. When used in connection with antisense technology, the $R^1$ moiety may be a lipid moiety to provide for delivery of the compound into the cell and into the nucleus of the cell.

Although compounds related to compound of Formula VI are disclosed in Nielsen, P. E., Exholm, M., Berg, R. H. et al. Science, 254 (1991) 1497, by using the synthesis methods of the present invention the $R^1$ group can vary to obtain novel compounds of Formula VI which have a variety of desirable characteristics, such as improved cell penetration with $R^1$ as a lipid moiety. "Lipid moiety" means a moiety containing long-chain aliphatic hydrocarbons and their derivatives. Functional groups on the chain (general terminal group) include carboxylic acids, alcohols, amines, amino alcohols, and aldehydes. The term also includes waxes, fats and derived compounds.

Further, the $R^1$ moiety can be used as a site-specific attachment point for a metal chelator, a nuclease, and the like.

Mixtures of the oligomers of the invention synthesized as described above are useful in that they can be screened to determine which, if any, of the NSGs have a given biological activity, e.g., bind to a known receptor. Methods of using such mixtures are taught in U.S. Pat. No. 5,010,175 issued Apr. 23, 1991 incorporated herein by reference.

Diagnosis and Therapy

The invention includes a method of antisense treatment comprising administering to a mammalian (human) cell in vitro or in vivo a pharmaceutical formulation comprising a pharmaceutically acceptable excipient carrier having dispersed therein a therapeutically effective amount of a compound of the Formula VI:

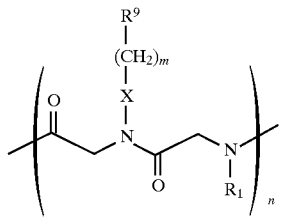

All of the variables are defined above.

The invention also includes a composition for diagnosis or therapy comprising an effective amount of an oligomer of the invention and a physiologically acceptable excipient or carrier.

Physiologically acceptable and pharmaceutically acceptable excipients and carriers for use with peptide and polyamide type reagents are well known to those of skill in the art.

By "physiologically or pharmaceutically acceptable carrier" as used herein is meant any substantially non-toxic carrier for administration in which the oligomers will remain stable and bioavailable when used. For example, the oligomer can be dissolved in a liquid, dispersed or emulsified in a medium in a conventional manner to form a liquid preparation or is mixed with a semi-solid (gel) or solid carrier to form a paste, ointment, cream, lotion or the like.

Suitable carriers include water, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, or gum arabic, synthetic polymers, such as discussed below, alcohols, polyols, water and the like. Preferably, because of its non-toxic properties, the carrier is a water miscible carrier composition that is substantially miscible in water. Such water miscible carrier composition can include those made with one or more ingredients set forth above but can also include sustained or delayed release carrier, including water containing, water dispersable or water soluble compositions, such as liposomes, microsponges, microspheres or microcapsules, aqueous base ointments, water-in-oil or oil-in-water emulsions or gels.

In one embodiment of the invention, the carrier comprises a sustained release or delayed release carrier. The carrier is any material capable of sustained or delayed release of the oligomer to provide a more efficient administration resulting in one or more of less frequent and/or decreased dosage of the protein growth factor, ease of handling, and extended or delayed effects. The carrier is capable of releasing the oligomer when exposed to the environment of the area for diagnosis or treatment or by diffusing or by release dependent on the degree of loading of the oligomer to the carrier in order to obtain releases of the oligomer. Non-limiting examples of such carriers include liposomes, microsponges, microspheres, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like.

Preferably, the sustained or delayed release carrier is a liposome, microsponge, microphere or gel.

The compositions of the invention are administered by any suitable means, including injection, transdermal, intraocular, transmucosal, bucal, intrapulmonary, and oral. While not required, it is desirable that parenteral compositions maintain the oligomer at the desired location for about 24 to 48 hours; thus, sustained release formulations can be used, including injectable and implantable formulations.

If desired, one or more additional ingredients can be combined in the carrier: such as a moisturizer, vitamins, emulsifier, dispersing agent, wetting agent, odor-modifying agent, gelling agents, stabilizer, propellant, antimicrobial agents, sunscreen, and the like. Those of skill in the art of diagnostic pharmaceutical formulations can readily select the appropriate specific additional ingredients and amounts thereof. Suitable non-limiting examples of additional ingredients include stearyl alcohol, isopropyl myristate, sorbitan monooleate, polyoxyethylene stearate, propylene glycol, water, alkali or alkaline earth lauryl sulfate, methylparaben, octyl dimethyl-p-amino benzoic acid (Padimate O), uric acid, reticulan, polymucosaccharides, hyaluronic acids, aloe vera, lecithin, polyoxyethylene sorbitan monooleate, tocopherol (Vitamin E) or the like.

Preferably the carrier is a pH balanced buffered aqueous solution for injection. However, the preferred carrier will vary with the mode of administration.

The compositions for administration usually contain from about 0.0001% to about 90% by weight of the oligomer compared to the total weight of the composition, preferably from about 0.5% to about 20% by weight of the oligomer compared to the total composition, and especially from about 2% to about 20% by weight of the oligomer compared to the total composition.

The effective amount of the oligomer used for therapy or diagnosis of course can vary depending on one or more of factors such as the specific oligomer used, the age and weight of the patient, the type of formulation and carrier ingredients, frequency of use, the type of therapy or diagnosis preformed and the like. It is a simple matter for those of skill in the art to determine the precise amounts to use taking into consideration these factors and the present specification.

EXAMPLES

The following examples are put forth so as to provide those of ordinary skill in the art with a complete disclosure and description of how to carry out the synthesis of the present invention and are not intended to limit the scope of what the inventors regard as their invention. Efforts have been made to ensure accuracy with respect to numbers used (e.g., amounts, temperature, etc.) but some experimental errors and deviation should be accounted for. Unless indicated otherwise, parts are parts by weight, molecular weight is weight average molecular weight, temperature is in degrees Centigrade and pressure is at or near atmospheric.

Oligomer syntheses were performed by an automated synthesizer (Zuckermann, R. N., Kerr, J. M., Siani, M. & Banville, S., Int. J. Peptide Protein Res. (1992), Vol. 40 pp. 497–506). The syntheses were conducted with Rink amide polystyrene resin (Rink, H., Tetrahedron Lett., 28, 3787–3790 (1987)) (50 μmol, substitution level 0.45 mmol/g) to avoid diketopiperazine formation. However, a variety of conventional peptide synthesis resins known to those skilled in the art can be used in place of the polystyrene.

Acylation reactions were performed by addition of bromoacetic acid (600 μmol, 83 mg) in DMF (0.83 mL), followed by addition of N,N'-diisopropylcarbodiimide activator (660 μmol, 103 μL) in DMF (170 μL). Reaction mixtures were agitated at room temperature for 30 min. Each acylation was repeated once before continuing to the displacement step.

Displacement reactions were performed by addition of primary amine (2.0 mmol) as 2.5M solutions in dimethylsulfoxide (1.0 mL), followed by agitation for 2 hr at room temperature. Optimization of displacement reactions was performed by varying amine concentrations from 0.25M to 2.5M.

The resulting oligomers were deprotected/cleaved by treatment of the oligomer-solid support with 95% trifluoroacetic acid in water (10 mL) for 20 min at room temperature, followed by filtration and lyophilization.

Examples 1–8

Eight representative penta-NSGs were prepared by the sub-monomer method from a variety of amines, including poorly nucleophilic, sterically-hindered and side-chain protected amines. All compounds were successfully synthesized as established by mass spectrometry, with isolated crude yields between 52 and 90%, and purities generally greater than 85% by HPLC. The purity, yields and mass spectrometry data on the pentamers were obtained and are shown below in Table III.

TABLE III

| Oligomer | purity (%)[a] | yield (%)[b] | MH[c] |
|---|---|---|---|
| 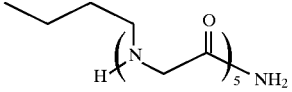 | >85 | 90 | 583.5 |
| 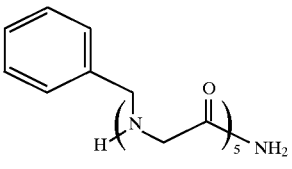 | >85 | 74 | 753.2 |
| 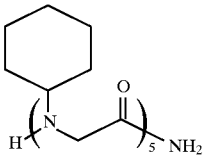 | >85 | 79 | 713.4 |

TABLE III-continued

| Oligomer | purity (%)[a] | yield (%)[b] | MH[c] |
|---|---|---|---|
| (diphenylmethyl-aminomethyl) pentamer with terminal NH₂ | >85 | 70 | 1204.1 |
| (N-phenyl) pentamer with terminal NH₂ | <85 | 83 | 683.3 |
| (N-cyclopropyl) pentamer with terminal NH₂ | >85 | 83 | 503.3 |
| (N-indolylethyl) pentamer with terminal NH₂ | >60 | 52 | 1018.4 |
| (N-(3-aminopropyl)) pentamer with terminal NH₂ | >85 | 63[d] | 588.4 |
| [(N-n-butylglycine)₄(N-(3-aminopropyl)glycine)]₅ | >65 | 86[d] | 2850.9 |

[a]Determined by HPLC.
[b]Determined from dry weight.
[c]Liquid matrix secondary-ion mass spectrometry.
[d]Made from Boc-NH—(CH₂)₃—NH₂.

Optimization of penta-NSG synthesis was performed using combinations of chloro, bromo and iodoacetic acid with both aniline and cyclohexylamine. Bromoacetic acid and iodoacetic acid proved superior to chloroacetic acid in forming penta-(N-phenylglycine) (79%, 83% and <5% yields, respectively). All three haloacetyl compounds successfully gave the penta-(N-cyclohexylglycine) oligomer in >75% yield. However, inclusion of 0.6M N-hydroxybenzotriazole in the acylation reactions (Robey, F. A., Harris, T. A., Hegaard, N. H. H., Nguyen, A. K., Batinic, D. *Chimica Oggi* 27–31 (1992)) yielded <5% of the penta-(N-cyclohexylglycine) polymer.

In further optimization studies, the molar concentration of primary amine was varied from 0.25M (4.0 equiv.) to 2.5M (40 equiv.) for n-butylamine, cyclopropylamine and diphenylethylamine using bromoacetic acid. Pentamers were obtained in >80% yield with n-butylamine and cyclopropylamine concentrations ≧1.0M, and diphenylethylamine concentrations ≧2.5M.

Example 9

A 25 mer, [(N-n-butylglycine)₄(N-(3-amino-propyl) glycine) ]₅, was synthesized by the sub-monomer method, thereby demonstrating the utility of this method for the preparation of longer oligomers. Analytical HPLC was performed on a Rainin HPX system controller with a C4 reversed-phase HPLC column (Vydac, 25 cm×4.6 mm) and a gradient elution (solvent A: H₂O/0.1% TFA and solvent B: CH₃CN/0.1% TFA; 10%–75% B in 35 min). Mass spectroscopy confirmed the identity of this compound (MH+= 2850.9) which was obtained in 86% yield and 65% purity by HPLC.

The efficient synthesis of a wide variety of oligomeric NSGs using automated synthesis technology, as presented here, makes these polymers attractive candidates for the generation and rapid screening of diverse peptidomimetic libraries.

Example 10

Solid support-bound amine in dimethylformamide (DMF) and 200 μl of diisopropylcarbodiimide was acylated twice with 800 μl of 0.6M bromoacetic acid in DMF for 30 minutes at room temperature. The acylated solid support-bound amine was washed three times with 2 mL of DMF.

The acylated solid support-bound amine was treated with 1 mL of a primary amine of Table IV as a 1–2M solution in dimethyl sulfoxide (DMSO) for two hours at room temperature. The above steps were repeated to form a pentamer. The desired pentamer product was washed three times with 2 mL of DMF, and subjected to reversed-phase HPLC using a standard acetonitrile gradient (0–60% in 30 minutes) to give the desired pentamer in greater than 85% purity.

TABLE IV

| Material | | Notes |
|---|---|---|
| 4-(2-aminoethyl)morpholine | 50 g | tertiary amine |
| aniline | 100 g | weak nucleophile |
| benzylamine | 100 g | |
| cyclopentylamine | 50 g | α-branched amine |
| N-Boc-1,6-diaminohexane (HCl) | 20 g | soluble at 1.5 M/DNSO |
| Glycine-OtBu (HCl) | 50 g | protecting group |
| hexylamine | 100 mL | |
| 2-methoxyethylamine | 50 mL | |
| methylamine (40% w/v in water) | 100 mL | use without dilution |
| tyramine | 50 g | soluble at 1 M/DMSO |
| bromoacetic acid | 200 g | |

All of the amine compounds listed were soluble in DMSO at 2M, except where otherwise noted. Tyramine was slow to dissolve, but gentle warming in a hot water bath speeded up the process. There was no need to protect the phenol functionality. Methylamine was quite volatile, but its high solubility in water allowed its use as an aqueous solution (undiluted from the bottle). Aniline was the least nucleophilic amine, but it still worked at a 2M concentration.

The hydrochloride salts were prepared by dissolving the compounds in DMSO and then adding a molar equivalent aqueous HCl. The salt precipitate was then removed by centrifugation, and the supernatant dried over molecular sieves.

Peptoid oligomers with a Rink amide linker were cleaved as follows:

25–50 μmol of support-bound oligomer was reacted with 2–4 mL of 95% trifluoroacetic acid/5% water for 20–30 min at room temperature; dilute with an equal volume of water, lyophilized, redissolve in 3–6 mL glacial acetic acid and relyophilized. The oligomers were usually powders rather than oils.

Example 11

The compounds described in Tables V and VI were synthesized as pentamers represented by Formula VIII:

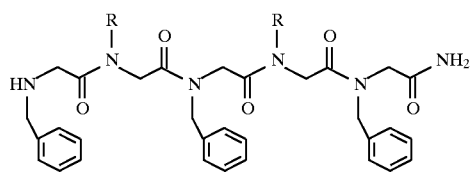

where R=the side-chain listed in Tables V and VI. All oligomers were analyzed by reverse phase HPLC and characterized by LSIMS mass spectrometry.

All compounds were synthesized by the solid-phase sub-monomer method as previously described, but with the above modifications.

TABLE V

Homopentamers with a toluic acid backbone generated by the sub-monomer method

| R—NH$_2$ | Yield (%) | Purity (%) | MH$^+$ |
|---|---|---|---|
| O-N-CH$_2$CH$_2$-NH$_2$ (morpholinoethyl) | 60 | 90 | 1247.7 |
| CH$_3$-O-CH$_2$CH$_2$-NH$_2$ | 72 | 80 | 973.6 |
| CH$_3$(CH$_2$)$_3$-NH$_2$ | 76 | 85 | 963.6 |

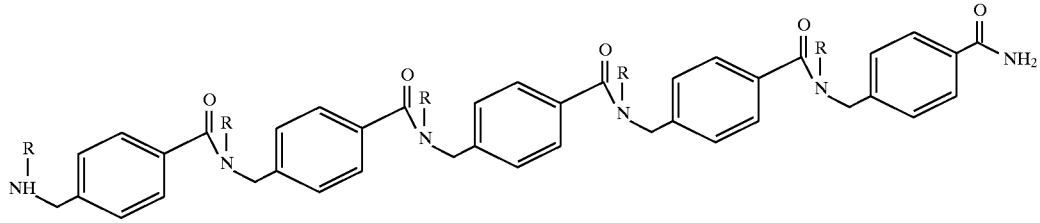

TABLE VI

Synthesis of Hydrazide-containing polymers by the Sub-monomer Method[a]

| R–C(O)–NHNH$_2$ | Yield (%) | Purity (%) | MH$^+$ |
|---|---|---|---|
| (phenyl)C(O)NHNH$_2$ | 88 | 90 | 687.3[b] |
| CH$_3$C(O)NHNH$_2$ | | | |

TABLE VI-continued

Synthesis of Hydrazide-containing polymers
by the Sub-monomer Method[a]

| R⎯C(O)⎯NHNH₂ | Yield (%) | Purity (%) | MH⁺ |
|---|---|---|---|
| CH₃⎯O⎯C(O)⎯NHNH₂ | 86 | 90 | 719.3 |
| (CH₃)₃C⎯O⎯C(O)⎯NHNH₂ | 75 | 80 | 603.2[c] |
| Ph⎯C(O)⎯NHNH₂ | 60 | 85 | 811.8 |
| PhCH₂⎯C(O)⎯NHNH₂ | 78 | 90 | 839.3 |
| PhCH₂⎯O⎯C(O)⎯NHNH₂ | 50 | 90 | |
| Ph⎯N(H)⎯C(O)⎯NHNH₂ | 88 | 90 | 841.4 |
| 4-CH₃O-C₆H₄-CH₂⎯O⎯C(O)⎯NHNH₂ | 70 | 80 | 603.2[c] |

[a]Synthsized as pentamers in the format Bn-X-Bn-X-Bn, where Bn=N-benzyl glycine.
[b]Synthesized as a homopentamer.
[c]Deprotects upon TFA cleavage to give the underivatized hydrazide.

Example 12

The method of the invention was used to synthesize pentamers in the format Bn—X—Bn—X—Bn, where Bn is N-benzylglycine using an alkoxyamine as the second sub-monomer substituted by —NH₂. When the alkoxyamine was methoxyamine the yield was 76% and the purity by HPLC was 90%. When phenylmethoxyamine was used as the alkoxyamine, the yield was 56% and the purity by HPLC was 50%.

TABLE VII

Synthesis of Alkoxyamine-containing
Polymers by the Sub-monomer Method[a]

| | Yield (%) | Purity (%) |
|---|---|---|
| CH₃—O—NH₂ | 76 | 90 |
| PhCH₂—O—NH₂ | 56 | 50 |

[a]synthesized as pentamers in the format Bn—X—Bn—X—Bn, where Bn=N-benzyl glycine.

Example 13
Synthesis of Ligands for α₁Adrenergic Receptors General Synthesis of Compounds Oligomer synthesis was performed on a Rink amide polystyrene resin (0.61 mmol/g, 1% crosslinked, 100–200 mesh). N,N-Dimethylformamide (DMF), dimethylsulfoxide (DMSO), methylene chloride, glacial acetic acid and trifluoroacetic acid (TFA) were obtained from commercial suppliers and used without further purification. Piperidine, bromoacetic acid, N,N-diisopropylcarbodiimide (DIC), phenethylamine, 4-aminobiphenyl, tyramine, and other reagents were obtained from Aldrich and used without further purification.

All reactions were performed at room temperature in a 2.0 L vessel equipped with a 10 cm coarse glass frit. Agitation of the solid support-reagent slurry was performed at every step by rotary shaking at 200 rpm. Filtration of the solid support-reagent slurry was achieved by the application of vacuum.

A 2.0 L vessel was charged with Rink amide resin (100 g, 0.061 mol). The resin was briefly swelled in DMF (1.5 L) with gentle agitation and drained. The 9-fluorenylmethoxycarbonyl (Fmoc) group was then removed by treatment with 20% piperidine/DMF (1.7 L, 1×5 min, followed by 1×20 min). The resin was then washed with DMF (6×1.7 L). The remainder of the compound was synthesized by performing three cycles of acylation with bromoacetic acid and displacement with an amine.

General acylation conditions (0.061 mol resin solid support):

Solid support-bound amines were bromoacetylated by Ln situ activation with DIC. To the oligomer-solid support was added a DMF solution of bromoacetic acid (0.67M, 900 mL) followed by DIC (neat, 93 mL, 0.60 mol). The reaction mixture was agitated for 30 min at room temperature. The mixture was drained and the reaction was repeated once. The solid support was washed with DMF (3×1.7 L).

General displacement conditions (0.61 mol):

Solid support-bound bromoacetamides were displaced by the addition of the amine as a solution in DMSO (1–2M, 1.0 L). The reaction mixture was agitated at room temperature for 2 hours. The reaction mixture was drained and the solid support was washed with DMF (3×1.7 L). Phenethylamine and 4-aminobiphenyl were used at 2.0M concentration, while tyramine and phenethylhydrazine were used at 1.0M.

General Cleavage and Purification:

After completion of the synthesis the solid support was washed with CH₂Cl₂ (3×1.7 L) and air dried for 5 minutes. The full length trimer was cleaved from the solid support (0.061 mol) by treatment with 95% TFA/5% water (1.5 L) at room temperature for 15 minutes. The solid support was then washed with 95% TFA/5% water (1×1.0 L) and CH₂Cl₂ (1×1 L). The filtrates were pooled and the solvent removed by rotary evaporation. The residue was dissolved in glacial acetic acid (150 mL) and lyophilized.

Example 14

Synthesis of Nhtyr-Nbiph-Nhphe

The compound Nhtyr-Nbiph-Nhphe was synthesized as described in Example 13 above, using phenethylamine as the first amine added, 4-aminobiphenyl as the second amine added, and 4-hydroxyphenethylamine as the third amine added.

After completion of the synthesis the solid support was washed with CH₂Cl₂ (3×1.7 L) and air dried for 5 minutes. The full length trimer was cleaved from the solid support (0.061 mol) by treatment with 95% TFA/5% water (1.5 L) at room temperature for 15 minutes. The solid support was then washed with 95% TFA/5% water (1×1.0 L) and CH₂Cl₂ (1×1 L). The filtrates were pooled and the solvent removed by rotary evaporation. The residue was dissolved in glacial acetic acid (150 mL) and lyophilized to afford a light yellow powder (1.7 g, 82% yield). The purity of the crude product was determined to be 90% by reverse-phase HPLC. The product was characterized by FAB-mass spectrometry (MH+ =565).

Example 15

Synthesis of Nhtyr-Npop-Nhphe

The compound Nhtyr-Npop-Nhphe was synthesized as described in Example 14 above, using phenethylamine as the first amine added, 4-amino-1-phenoxybenzene as the second amine added, and 4-hydroxyphenethylamine as the third amine added.

Example 16

Synthesis of Backbone Variants

Proceeding as described in Example 14 above, but substituting 3-bromopropanoic acid and 2-bromopropanoic acid for bromoacetic acid at some positions, the following compounds were prepared:

Nhtyr-Nbiph-Nmhphe;
Nhtyr-Nbiph-Nphphe;
Nphtyr-Nbiph-Nhphe; and
Nhtyr-Npbiph-Nhphe.

Example 17

Synthesis of Additional Compounds

Proceeding as described in Example 14 above, but substituting phenethylamine, phenethylhydrazine and 3,4-methylenedioxyphenethylamine for tyramine, the compounds Nhphe-Nbiph-Nhphe, Nzhphe-Nbiph-Nhphe and Noco-Nbiph-Nhphe were prepared. The compound Nhphe-Nbiph-Nhphe was additionally N-benzylated to produce Bz-Nhphe-Nbiph-Nhphe.

Example 18

Proceeding as described in Examples 14 and 17 above, but substituting 3-trifluoromethylphenethylamine, 2-chlorophenethylamine, 3-chlorophenethylamine, 4-chlorophenethylamine, 2,4-dichlorophenethylamine, 3-bromophenethylamine, 4-iodophenethylamine, 3-hydroxyphenethylamine, 4-hydroxyphenethylamine, 2,4-dihydroxyphenethylamine, 2-methylphenethylamine, 3-methylphenethylamine, 4-methylphenethylamine, 2,4-dimethylphenethylamine, 2,4,6-trimethylphenethylamine, 3-ethylphenethylamine, 4-ethylphenethylamine, 4-hexylphenethylamine, 3-nitrophenethylamine, 2-aminophenethylamine, 4-aminophenethylamine, 2,4-diaminophenethylamine, 2-methoxyphenethylamine, 3-methoxyphenethylamine, 4-methoxyphenethylamine, 2,4-dimethoxyphenethylamine, 2,4,6-trimethoxyphenethylamine, 3,4-dimethoxyphenethylamine, 2-ethoxyphenethylamine, 3-ethoxyphenethylamine, 4-ethoxyphenethylamine, 3-propoxyphenethylamine, 4-butoxyphenethylamine, 4-t-butoxyphenethylamine, 3-methoxymethylphenethylamine, 4-methoxymethylphenethylamine, 3-(2-methoxyethyl)phenethylamine, 4-(2-methoxyethyl)phenethylamine, 4-(2-hydroxyethyl)phenethylamine, 4-( 3-hydroxypropyl)phenethylamine, 4-(2-hydroxyethoxy)phenethylamine, 4-phenylphenethylamine, 4-(2-chlorophenyl)phenethylamine, 4-(2-aminophenyl)phenethylamine, 3-(2,4,6-trimethylphenyl)phenethylamine, 4-phenoxyphenethylamine, 4-(3-chlorophenoxy) phenethylamine, 4-(4-aminophenoxy)phenethylamine, 3-benzylphenethylamine, 4-phenethylphenethylamine, 3-acetylphenethylamine, 4-acetylphenethylamine, 4-(2-phenoxyethyl)phenethylamine, and 3-benzyloxyphenethylamine for phenethylamine, and/or 3'-trifluoromethyl-4-aminobiphenyl, 2'-chloro-4-aminobiphenyl, 3-chloro-4-aminobiphenyl, 4'-chloro-4-aminobiphenyl, 2',4'-dichloro-4-aminobiphenyl, 3-bromo-4-aminobiphenyl, 4'-iodo-4-aminobiphenyl, 3'-hydroxy-4-aminobiphenyl, 4'-hydroxy-4-aminobiphenyl, 2',4'-dihydroxy-4-aminobiphenyl, 2'-methyl-4-aminobiphenyl, 3'-methyl-4-aminobiphenyl, 4'-methyl-4-aminobiphenyl, 2',4'-dimethyl-4-aminobiphenyl, 2',4',6'-trimethyl-4-aminobiphenyl, 2',3,4',5,6'-pentamethyl-4-aminobiphenyl, 3'-ethyl-4-aminobiphenyl, 4'-ethyl-4-aminobiphenyl, 4'-hexyl-4-aminobiphenyl, 3'-nitro-4-aminobiphenyl, 2'-amino-4-aminobiphenyl, 4'-amino-4-aminobiphenyl, 2',4'-diamino-4-aminobiphenyl, 2'-methoxy-4-aminobiphenyl, 3'-methoxy-4-aminobiphenyl, 4'-methoxy-4-aminobiphenyl, 2',4'-dimethoxy-4-aminobiphenyl, 2',4',6'-trimethoxy-4-aminobiphenyl, 3',4'-dimethoxy-4-aminobiphenyl, 2'-ethoxy-4-aminobiphenyl, 3'-ethoxy-4-aminobiphenyl, 4'-ethoxy-4-aminobiphenyl, 3'-propoxy-4-aminobiphenyl, 4'-butoxy-4-aminobiphenyl, 4'-t-butoxy-4-aminobiphenyl, 3'-methoxymethyl-4-aminobiphenyl, 4'-methoxymethyl-4-aminobiphenyl, 3'-methoxyethyl-4-aminobiphenyl, 4'-methoxyethyl-4-aminobiphenyl, 4'-hydroxyethyl-4-aminobiphenyl, 4'-hydroxypropyl-4-aminobiphenyl, 4'-hydroxyethoxy-4-aminobiphenyl, 4'-phenyl-4-aminobiphenyl, 4'-(2-chlorophenyl)-4-aminobiphenyl, 4'-(2-aminophenyl)-4-aminobiphenyl, 3'-(2,4,6-trimethylphenyl)-4-aminobiphenyl, 4'-phenoxy-4-aminobiphenyl, 4'-(3-chlorophenoxy)-4-aminobiphenyl, 4'-(4-aminophenoxy)-4-aminobiphenyl, 3'-benzyl-4-aminobiphenyl, 4'-phenethyl-4-aminobiphenyl, 3'-acetyl-4-aminobiphenyl, 4'-acetyl-4-aminobiphenyl, 4'-(2-phenoxyethyl)-4-aminobiphenyl, and 3'-benzyloxy-4-aminobiphenyl for 4-aminobiphenyl, and/or phenethylamine, 3-trifluoromethylphenethylamine, 2-chlorophenethylamine, 3-chlorophenethylamine, 4-chlorophenethylamine, 2,6-dichlorophenethylamine, 3-bromophenethylamine, 4-fluorophenethylamine, 3-hydroxyphenethylamine, 2,5-dihydroxyphenethylamine, 2-methylphenethylamine, 3-methylphenethylamine, 4-methylphenethylamine, 2,4-dimethylphenethylamine, 2,4,6-trimethylphenethylamine, 3-ethylphenethylamine, 4-ethylphenethylamine, 4-hexylphenethylamine, 3-nitrophenethylamine, 2-aminophenethylamine, 4-aminophenethylamine, 2,4-diaminophenethylamine, 2-methoxyphenethylamine, 2,5-dimethoxyphenethylamine, 2,3-dimethoxyphenethylamine, 3,5-dimethoxyphenethylamine, 3,4,5-trimethoxyphenethylamine, 3-methoxyphenethylamine, 4-methoxyphenethylamine, 2,4-dimethoxyphenethylamine, 2,4,6-trimethoxyphenethylamine, 3,4-dimethoxyphenethylamine, 2-ethoxyphenethylamine, 3-ethoxyphenethylamine, 4-ethoxyphenethylamine, 3-propoxyphenethylamine, 4-butoxyphenethylamine, 4-t-butoxyphenethylamine, 3-methoxymethylphenethylamine, 4-methoxymethylphenethylamine, 3-methoxyethylphenethylamine, 4-methoxyethylphenethylamine, 4-hydroxyethylphenethylamine, 4-hydroxypropylphenethylamine, 4-hydroxyethoxyphenethylamine, 4-phenylphenethylamine, 4-(2-chlorophenyl)phenethylamine, 4-(2-aminophenyl) phenethylamine, 3-( 2,4,6-trimethylphenyl)phenethylamine, 4-phenoxyphenethylamine, 4-(3-chlorophenoxy) phenethylamine, 3,4-methylenedioxyphenethylamine, 6-methoxy-3,4-methylenedioxyphenethylamine, 2-methoxy-3,4-methylenedioxyphenethylamine, 4,5-methylenedioxyphenethylamine, 3-methoxy-4,5-methylenedioxyphenethylamine, 4-(4-aminophenoxy) phenethylamine, 3-benzylphenethylamine, 4-phenethylphenethylamine, 3-acetylphenethylamine, 4-acetylphenethylamine, 4-(2-phenoxyethyl) phenethylamine, and 3-benzyloxyphenethylamine for 4-hydroxyphenethylamine, the corresponding compounds are prepared.

Synthesis of Oligo N-Substituted Carbamates

A general synthetic scheme for oligo N-substituted carbamates is shown in Scheme 3. A two-step process was devised which used an alternating scheme of acylation and alkylation. In scheme 3, n is from 2–2000, preferably 2–100, more preferably 2–10. $R_x$ and $R_y$ are independently any side chain selected from the group consisting of halo, nitro, lower alkyl, lower cycloalkyl, —OH, —$NR_aR_b$ where $R_a$ and $R_b$ are each independently —H or lower alkyl, —$OR_a$, —$C(O)R_a$, —$OC(O)R_a$, —$C(O)OR_a$, —$OC(O)OR_a$, —$(CH_2)_a$—$CX_1X_2X_3$ where n is 0–6 and $X_{1-3}$ are each independently H or halo, —$NC(O)R_a$, —$C(O)NR_aR_b$, —$OC(O)NR_aR_b$, or —$NC(O)NR_aR_b$, where a, b are independently integers from 1 to 100. The conditions for the following example carbamate syntheses were modeled after the submonomer scheme for synthesizing NSG-peptoids described herein.

Scheme 3
Synthetic Scheme for N-substituted Carbamates

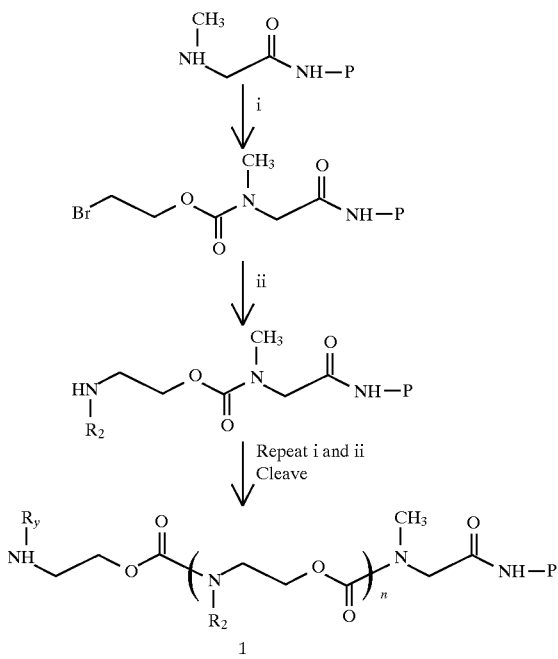

i. BrCH2CH2OCOCl (0.1 M), DIEA (0.3 M), DCM, 30 minutes, RT
ii. RNH2 (2 M), DMSO, time, temp
iii. 95% TFA, aq., 90 min, RT For the acylation step, I, 2-bromoethylchloroformate (BECF) was used. BECF quantitatively acylated solid support-bound sarcosine in the presence of DIEA in 30 minutes at ambient temperature (0.3M BECF, 0.3M DIEA, in dichloromethane). For the alkylation step, II, the preferred conditions were 2M amine, DMSO, 45° C., 4 hours. The preparation of compounds 2–4 was performed using these conditions in most cases. Temperature and reaction time were varied for the synthesis of some compounds as the preferred general conditions were developed. Each reaction step is followed by thorough washing with the reaction solvents, and some combination of DCM, DMF, and/or MeOH.

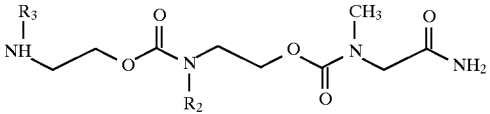

2a: $R_2$ = butyl, $R_3$ = benzyl
2b: $R_2$ = phenyl, $R_3$ = benzyl
3: $R_2$ = X, $R_3$ = benzyl
4: $R_2$ = phenyl, $R_3$ = X As an example, the synthesis of oligo N-substituted carbamate 2a ($R^2$=butyl, $R^3$=benzyl) by the submonomer method is described. A solid support, FMOC-protected Rink amide resin (250 mg, 0.43 mmol/g), was treated with 20% piperidine/DMF for 20 minutes to remove N-terminal FMOC group. After thorough washing, the solid support was acylated with FMOC-Sar-OH using standard methods. The N-terminal FMOC group was removed with 20% piperidine/DMF.

The above solid support was swollen with DCM and drained. A solution of bromoethylchloroformate (180 μL, 1.67 mmol) and DIEA (260 μL, 1.5 mmol) in 5 mL of DCM was added to the solid support and the solid support was shaken for 30 minutes. The solid support was then washed well. To this solid support was added a solution of butylamine (790 μL, 8.0 mmol) in DMF (3.2 mL) and it was allowed to react for 2 hours with gentle shaking.

The acylation was repeated using bromoethylchloroformate (160 μL, 1.5 mmol), and DIEA (260 μL, 1.5 mmol) in DCM (5 mL) for 45 minutes. Following washing, the solid support was treated with a solution of benzylamine (875 μL, 8 mmol) in 3.2 mL DMF for 2 hours.

The solid support was then washed and cleaved with 95% TFA/H2O for 90 minutes. The resulting solution was analyzed by C-4 RP-HPLC and MS. Three major peaks were obtained in approximately a 1:2:1 ratio. MS revealed the middle peak to be the correct material, structure given below. The early eluting peak was the deletion product (incomplete reaction on BuNH2 step). The last peak appears to be the product from the second acylation reaction, i.e., incomplete reaction on the final benzylamine step.

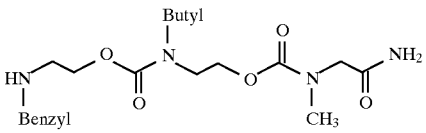

In general, the Butyl or Benzyl may be any side chain as defined above or be selected from the group consisting of halo, nitro, lower alkyl, lower cycloalkyl, —OH, —$NR_aR_b$ where $R_a$ and $R_b$ are each independently —H or lower alkyl, —$OR_a$, —$C(O)R_a$, —$OC(O)R_a$, —$C(O)OR_a$, —$OC(O)OR_a$, —$(CH_2)_a$—$CX_1X_2X_3$ where n is 0–6 and $X_{1-3}$ are each independently H or halo, —$NC(O)R_a$, —$C(O)NR_aR_b$, —$OC(O)NR_aR_b$, or —$NC(O)NR_aR_b$.

Tables I and II list N-substituted carbamates prepared as described herein. Table I lists 53 substituents "X" of NSCs having the general structure 3. Table II lists 13 substituents "X" of NSCs having the general structure 4. These results show that a wide variety of amines can be used to prepare many different N-substituted carbamates where the substitution is either at an internal position or at the N-terminus.

TABLE I

N-substituted Carbamates of General Structure 3

| Entry | Amines (a) Compounds 3: | HPLC Yield % (b) | Crude Yield % |
|---|---|---|---|
| | X = | | |
| 1 | N,N-(Diisopropyl)ethylenediamine | 83% | 107% |
| 2 | Benzylamine | 82% | 91% |
| 3 | 1-(3-Aminopropyl)-2-pyrrolidinone | 81% | 87% |
| 4 | 2-(2,6-Dichlorobenzyl)thioethylamine | 79% | 88% |
| 5 | 3,3,5-Trimethylcyclohexyalamine | 78% | 90% |
| 6 | 3-Butoxypropylamine | 78% | 82% |
| 7 | 4-(Trifluoromethyl)benzylamine | 77% | 92% |
| 8 | 4-tert-Butylcyclohexylamine | 77% | 98% |
| 9 | (Aminoethyl)cyclopropane | 76% | 94% |
| 10 | 2-(Phenylethyl)amine | 76% | 93% |
| 11 | 2,2-Diphenylethylamine | 75% | 93% |
| 12 | 4-Phenylbutylamine | 75% | 80% |
| 13 | 1,4-Dimethylheptamine | 74% | 88% |
| 14 | 2-Aminomethyl-3-chlorodiphenyl ether | 74% | 88% |
| 15 | 2-(1-cyclohexenyl)ethylamine | 74% | 86% |
| 16 | 2-Norbornylamine | 72% | 94% |
| 17 | 2-[2-(Aminomethyl)phenyl-thio]benzyl alcohol | 71% | 96% |
| 18 | 4-Methoxybenzylamine | 71% | 113% |
| 19 | S-tert-Butylmercaptoethylamine | 71% | 99% |
| 20 | Tyramine | 71% | 90% |
| | X = | | |
| 21 | Butylamine | 70% | 98% |
| 22 | Tetrahydrofurfurylamine | 70% | 79% |
| 23 | Heptylamine | 68% | 87% |
| 24 | Piperonylamine | 68% | 90% |
| 25 | 6-Aminohexanoic acid, tert-butyl ester (d) | 67% | c |
| 26 | Cyclopentylamine | 67% | 88% |
| 27 | 2-(Aminomethyl)pyrdine | 66% | 109% |
| 28 | Aminofluorene | 63% | 64% |
| 29 | N(in)-BOC-tryptamine (d) | 63% | c |
| 30 | N-BOC-1,2-ethylenediamine | 62% | 113% |
| 31 | 4-Amino-1-benzylpiperdine | 61% | 114% |
| 32 | N-BOC-1,6-hexanediamine | 61% | 93% |
| 33 | Furfurylamine | 56% | 57% |
| 34 | N-Acetylethylenediamine | 56% | 91% |
| 35 | trans-2-Phenyl-1-cyclopropylamine | 55% | 56% |
| 36 | 2-(2-Aminoethylamino)-5-nitropyridine | 53% | 105% |
| 37 | Cyclopropylamine | 51% | 87% |
| 38 | 3,5-Bis(trifluoromethyl)benzylamine | 47% | c |
| 39 | Aniline | 47% | c |
| 40 | Ethanolamine | 42% | 107% |
| | X = | | |
| 41 | Ethanolamine, tert-butyl ether | 37% | c |
| 42 | N(im)-BOC-histamine (d) | 37% | 93% |
| 43 | 3-Aminopropionitrile | 33% | c |
| 44 | 1,2,3,4-Tetrahydrol-1-napthylamine | 23% | 92% |
| 45 | 2,2,2-Trifluoroethylamine | 20% | 63% |
| 46 | B-Alanine amide | c | c |
| 47 | B-Alanine ethyl ester | c | c |
| 48 | Cyanamide | c | c |
| 49 | Aminoacetal | c | 67% |
| 50 | (4S,5S)-5-Amino-2,2-dimethyl-4-phenyl-1,3-dioxane | c | 80% |
| 51 | 1-(2-Aminoethyl)pyrrolidine | c | 141% |
| 52 | 4-(2-Aminoethyl)benzenesulfonamide | c | 77% |
| 53 | 3-Aminocrotononitrile | c | 59% |

(a): Commercially available unless otherwise indicated,
(b): From integration of HPLC trace,
c: Not determined,
(d): Prepared from amine via standard methods.

TABLE II

N-substituted Carbamates of General Structure 4

| Entry | Amines (a) Compounds 4 | HPLC Yield % (b) | Crude Yield % |
|---|---|---|---|
| | X = | | |
| 1 | Piperdine | 96% | |
| 2 | 4-(2-Aminoethyl)morpholine | 90% | |
| 3 | Ethyl 4-amino-1-piperdinecarboxylate | 87% | |
| 4 | Histamine | 85% | |
| 5 | 1,3-Diamino-2-propanol | 79% | |
| 6 | 2,2-Dimethyl-1,3-propanediamine | 79% | |
| 7 | Ethanolamine | 78% | |
| 8 | 1,2-Diamino-2-methylpropane | 76% | |
| 9 | 2-Aminobenzylamine | 75% | |
| 10 | 4-Amino-1-benzylpiperdine | 74% | |
| 11 | 2-(2-Aminoethoxy)ethanol | 69% | |
| 12 | L-2-Amino-3-methytbutanol | 55% | |
| 13 | 3-Aminoquinuclidine | 36% | |

(a): Commercially available unless otherwise indicated,
(b): From HPLC trace,

Synthesis of Highly Substituted Cyclic Compounds and Libraries Thereof via the Submonomer Method Highly substituted cyclic structures can be synthesized on a solid support by combining the submonomer method of the invention with powerful solution phase chemistry. Cyclic compounds containing one, two, three or more fused rings formed by the submonomer method by first synthesizing a linear peptoid backbone followed by subsequent intramolecular or intermolecular cyclization.

Substituted 2-isoquinolinones are synthesized by first reacting a solid support-bound amine with a halo-2-alkenoic acid to produce an unsaturated monopeptoid. Acylation with an o-halo-carboxylic acid halide provides an intermediate unsaturated peptoid. Palladium(0) catalyzed intramolecular Heck reaction results in the formation of 5, 6, and 7 membered rings fused to aromatic rings. A general structure of a substituted isoquinolinone prepared by the method of the invention is shown below.

Synthesis of 3-dihydroisoquinolinone structures are possible using the method of the invention, illustrating the versatility of the method. A solid support-bound linear peptoid is reacted with a primary amine, followed by reaction with an alkenoic acid halide. The resulting linear peptoid is intramolecularly cyclized by Pd(0)-catalyzed Heck reaction. The solid support-bound fused ring compound may be subsequently cleaved from the solid support. A general structure of an isoquinolinone compound is shown below.

3-Dihydroisoquinolinone

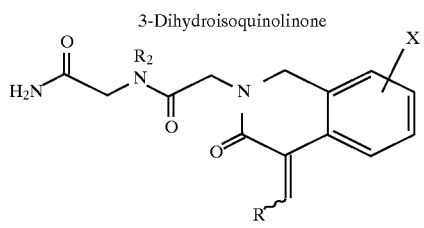

Phenanthridone

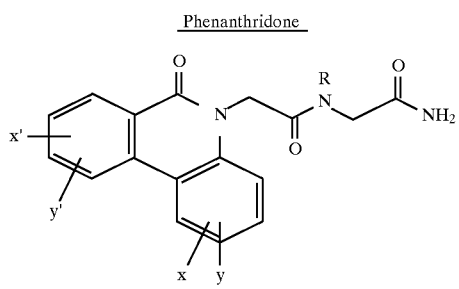

Substituted tetrahydroisoquinolines can also be prepared by the method of the invention in which a linear peptoid backbone is synthesized and subsequently cyclized. In general, a solid support-bound peptoid is reacted with a halo-2-alkenoic acid followed by nucleophilic displacement of the halide by an o-halo-aromatic primary or secondary amine. A palladium(0) catalyzed intramolecular Heck reaction is performed to cyclize the linear peptoid. The resultant molecule is a substituted tetrahydroisoquinoline with substituents provided by the alkenoic carboxylic acid and the primary or secondary amine used in the second step. The size of the fused ring is controlled by the structure of the side chain of the final amine reactant. A general structure of a substituted isoquinoline prepared according to the invention is shown below.

Tetrahydroisoquinoline

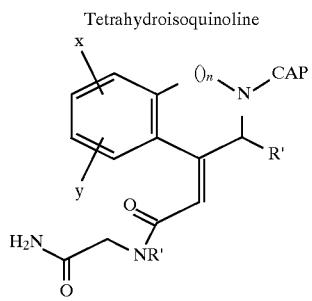

Compounds containing three fused rings can also be synthesized by the method of the invention by first reacting an amine-derivatized solid support resin or linear peptoid with an alkenoic acid, followed by reaction with a substituted amine, and then reacted with an acid halide containing an electrophilic reactive group in addition to the acid halide. This series of reactions produces a linear peptoid which, when subjected to appropriate conditions for intramolecular reaction, forms a ring structure. The backbone of the ring is formed by a portion of the linear peptoid backbone and covalent bonds of the peptoid side chains or substituents. If a side chain and substituent participating in ring formation are themselves cyclic, then the final product will be a fused ring structure. An example of a general structure of a compound containing three fused rings (e.g., a phenanthridone) prepared according to the submonomer method of the invention is shown below.

In the above structure, X, X', Y, and Y' should not be a halide which will compete for reaction with the reactive electrophilic group at the ortho position susceptible to nucleophilic attack during cyclization.

Synthesis of complex ring structures demonstrates the versatility of the submonomer method for making mixtures of complex cyclic compounds. The synthesis of mixtures of monoketopiperazines provides an example.

Monoketopiperazine mixtures are prepared by generating a linear peptoid by the submonomer method. By varying the submonomers used, a variety of peptoid backbones are prepared for intramolecular cyclization, thereby producing a mixture of monoketopiperazines. The submonomers used to prepare the peptoid backbone determine the ring substituents and peptoid side chains. A general structure of a monoketopiperazine is shown below.

Monoketopiperazine

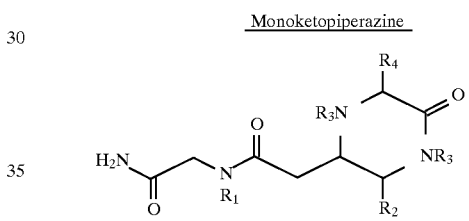

Monoketopiperazines of a mixture can be further reacted intermolecularly with aldehydes, and with alkenes or alkynes containing an electron withdrawing group to prepare mixtures of monoketopiperazines having more complex ring structures as shown below, which contains a five-membered ring fused to the monoketopiperazine.

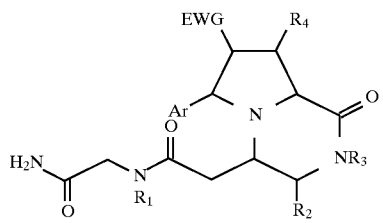

Synthesis of 1,4-benzodiazepine-2,5-dione mixtures is also demonstrated herein by the submonomer method. In this case the method utilizes halocarboxylic acid, primary amines, α-amino acid ester free bases, and o-azido-benzoyl chlorides as the submonomers which make up the peptoid backbone and contribute the ring and side chain substituents. The diversity of the benzodiazepinedione mixture is controlled by the number of varied substituents added via the submonomers. A general structure of 1,4-benzodiazepine-2,5-dione is shown below.

1,4-Benzodiazepine-2,5-dione

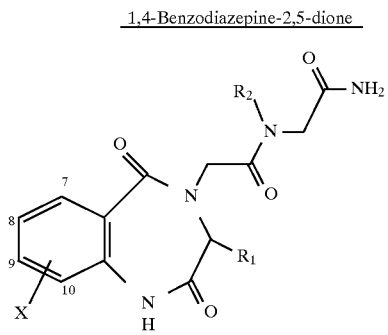

Preparing Cyclic Compounds from Peptoids by the Submonomer Method

In general, a solid support derivatized with an amine or peptoid is acylated by a first submonomer (such as by reaction with a halo-alkenoic acid or halo-acetic acid) followed by reaction with one of the following second submonomer compounds: a substituted primary or secondary amine; and a primary or secondary amine in which a substituent has a reactive moiety. This is followed by further sequential reactions with one or more of the following: an acid halide; an acid halide containing a reactive moiety other than the halide attached to the acyl carbon; an isocyanate; an isothiocyanate; and a primary or secondary amine. The reactive moiety of a submonomer such as an amine, an acid halide, an isocyanate, or an isothiocyanate is positioned such that, following attachment of the submonomer to the peptoid backbone, the reactive moiety is capable of or susceptible to cyclization. The order in which the compounds are reacted, their structure, as well as the reaction conditions determines the structure of the product. However, it can be readily seen that the synthetic schema presented herein have several features in common for synthesizing relatively complex molecules from small, substituted molecules in a sequential, stepwise procedure. In each case, a linear substituted peptoid backbone is formed and then cyclized to generate a highly substituted cyclic product. The submonomer method is readily combined with the split-resin method for the preparation of a diverse library of cyclic compounds.

The general synthesis of cyclic organic compounds by the submonomer method is as follows. A first submonomer compound is reacted with a prepared solid support such that substantially all of the reactive sites on the solid support are occupied by a covalently attached first submonomer molecule. A second submonomer is then reacted with a reactive site on the first submonomer. The first and second submonomer molecule can be a substituted alkenoic carboxylic acid, a substituted amine, a substituted acid halide, an isocyanate, an isothiocyanate, a substituted sulfonyl halide, or a substituted chloroformate. It can be seen that the sequential submonomer addition method of the invention is the basis for preparing the linear peptoid molecule which is subsequently cyclized to generate a final product.

The method of portioning and recombining reacted solid support is a feature of the submonomer method of cyclic peptoid synthesis which allows the production of mixtures of highly substituted cyclic structures. Mixtures of products result from two features of the invention: 1) the combination and relative positions of variable substituents on the submonomer compounds and, 2) from portioning and recombining reacted solid support particles at selected submonomer additions to produce a mixture of precursor linear peptoids prior to cyclization. The number of different product compounds in a mixture increases with 1) the number of different first submonomers attached to a solid support; 2) the number of different second submonomer compounds reacted with the first submonomer; and 3) the number of variable substituents on each first and second submonomer compound. In accordance with the present invention, this methodology allows for the production of libraries of cyclic organic compounds. More specifically, applicant's method involves preparing mixtures of distinct, unique and different cyclic organic compounds in the same reaction vessel and on a solid phase support. That is, the cyclic organic product compounds within the reaction vessel are different from one another and each of the cyclic organic product compounds in the reaction vessel is present in retrievable and analyzable amounts.

By combining the solid support-bound peptoid compounds and submonomer reactants in relative quantities such that each reaction is driven to substantial completion, the resulting mixture of cyclic organic compounds will contain each reaction product in a predictable and defined amount and in an amount sufficient such that the cyclic organic compounds can be retrieved and analyzed. The resulting amounts of each of the cyclic organic compounds is predictable in that the amount of derivatized solid support is used in each reaction is controlled and each subsequent reaction is driven to completion.

In accordance with a general aspect of the invention, individual cyclic organic compounds are produced using methodology such as solid-phase synthetic techniques after immobilizing the precursor compound on a solid support such that the a reactive moiety is available to react with a submonomer compound which, in turn, is reacted with one or more subsequent submonomers, and then cyclized. Cyclized peptoid derivatives can remain attached to the solid support for convenient retrieval. Cleavage of a cyclized peptoid derivative can also be performed before retrieval or before use, as necessary.

Since the variety of cyclized compounds prepared by the submonomer method is partially controlled by the order of submonomer reaction, it is readily seen that particulate solid support can be apportioned and recombined with each subsequent submonomer reaction such that a mixture of linear peptoid derivatives is formed when the portions are combined prior to cyclization. Where a reaction and reaction conditions are common to more than one linear peptoid derivative, the common reaction can be performed on the mixture.

Libraries of cyclic organic compounds synthesized on a solid-support

To most efficiently probe the binding region of a receptor protein or other molecule, it is generally preferred to create a library of cyclic organic compounds having a variety of substitutions and/or ring structures. The variety of structures in a library increases the chance of isolating a compound having desired binding properties. By applying the methods described herein to synthesis of a collection of cyclic organic compounds on a solid support, one may prepare a large group of compounds for screening. For example, one can prepare a library of monoketopiperazine derivatives having a variety of substituents for analysis of the relative receptor binding affinities. The library may be small (approximately 10 different structures) or large (more than 1000 different structures).

Such libraries are useful for identifying cyclic organic analogs to a bioactive peptide or other molecule which binds with a requisite affinity to the appropriate receptor. For example, if the hypothetical peptide binds to a known cell-surface receptor, one can prepare a culture of cells expressing the cell-surface receptor, apply the library under conditions conducive to binding, and determine the degree to which members of the library bind the cell-surface receptor or elicit a receptor response.

After interacting the cyclic organic compounds of the library with the receptor, the nonbinding compounds are (1942) Justus Liebigs Ann. Chim. 551:80) to deprotected Rink amide resin (Scheme 4).

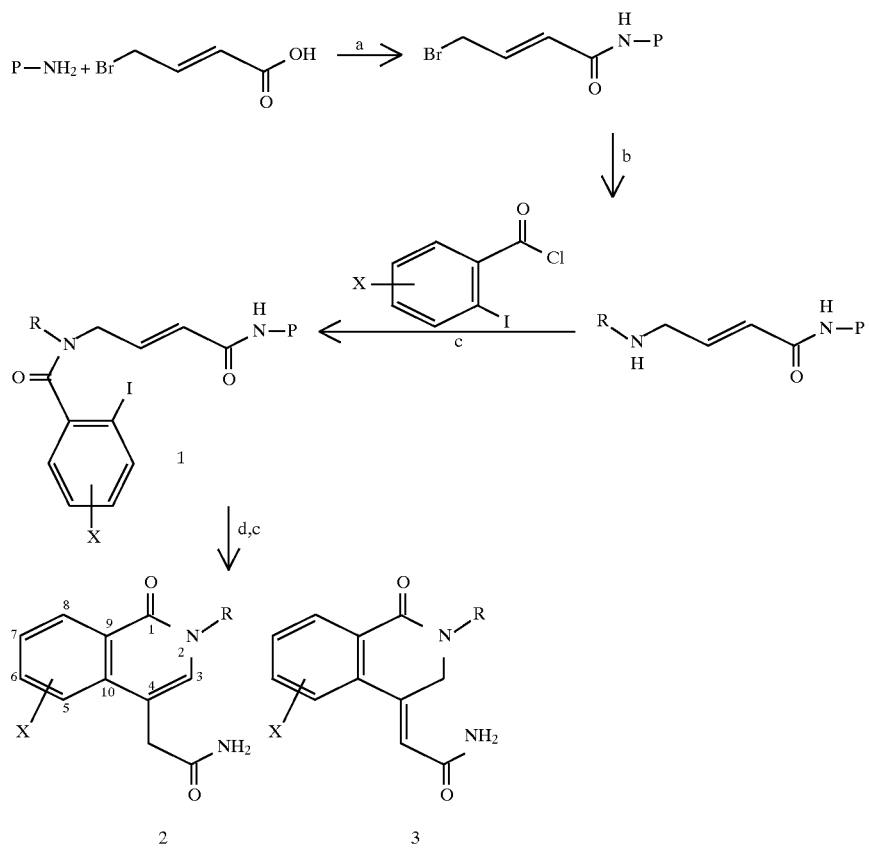

Scheme 4 a) 0.6M 4-bromo-2-butenoic acid and 0.6 M DIC in DMF, 2 × 30 min, RT
b) 2.0M RNH$_2$ in DMSO, 2h, RT
c) 0.5M iodoacid chloride, 0.5M triethylamine, RT, 2 × 30 min
d) Pd(Ph$_3$P)$_4$, NaOAc, Ph$_3$P, DMA, 85° C., 5h
e) 95/5 TFA/H$_2$O, 20 min, RT, then lyophilize.

removed by washing. If a large number of cyclic organic compounds exhibit high binding affinity, the binding conditions may be altered so that only the highest affinity cyclic organic compounds remain bound. The resulting selected cyclic organic compounds may then be removed and identified by standard analytical techniques.

If the relevant structure of the active portion of a bioactive molecule to be mimicked is unknown, for example, the method of the invention is employed to simply construct a larger library. Absent clues as to the structural configuration of the peptide or epitope, a "universal" library having a large range of substituent and/or ring structure variations is most useful.

Example 19

Solid-phase Synthesis of Highly Substituted 1-(2H)-isoquinolinones by the Submonomer Method Synthesis of highly substituted 1-(2H)-isoquinolinones utilizes the method of the invention to construct a substituted linear peptoid backbone, followed by cyclization of the backbone to yield a mixture of desired cyclic compounds. The first step in the synthesis is to couple trans-4-bromo-2-butenoic acid (bromocrotonic acid; see Ziegler, K. et al.

Subsequent S$_N$2 amine displacement under the conditions developed for the submonomer method of peptoid synthesis gives the unsaturated monopeptoid, with no evidence of competing S$_N$2' attack at the α-position. Acylation of the monopeptoid with an o-iodo-carboxylic acid, o-bromo-carboxylic acid, or o-trifluoro-methane sulfonyl-carboxylic acid gives an intermediate able to undergo a palladium(0) catalyzed intramolecular Heck reaction to the peptoid backbone, which is facilitated by an electron withdrawing carboxamide group. The o-iodo- or o-bromo-carboxylic acids can readily be prepared from commercially available anthranilic acids as well as from heterocycles such as pyridine or pyrazine carboxylic acids.

The intramolecular Heck reaction is a powerful method for forming five-, six-, or seven-membered rings fused to aromatic rings. An intermolecular Heck reaction of compounds on a solid support has been reported (Yu, K.-L. et al. (1994) Tet. Lett. 35:8919–8922). However, the preparation of cyclic structures by the submonomer method of the invention is uniquely capable of providing a mixture of cyclic compounds by varying the substituents on the submonomers.

In a representative preparation, solid support-bound monopeptoid 1a (R=iBu; Scheme 4) capped with o-iodobenzoyl chloride was treated with Pd(Ph₃P)₄ in DMA in the presence of sodium acetate and Ph₃P for 5 hr at 85° C. A facile cyclization occurred which was immediately apparent by HPLC analysis of the crude product obtained by treatment of the solid support with 95/5 TFA/H₂O. The uncyclized C-terminal amide resulting from cleavage of compound 1a (R=iBu; Scheme 4) elutes as a broad peak at 23.9 min, while the cyclized product is a sharp peak with a retention time of 18.7 min using a Vydac C-18 analytical HPLC column, an elution solvent gradient of 0–80% acetonitrile in aqueous 0.5% TFA over 40 min. The cyclized product was analyzed by a combination of HMBC/HMQC and ROESY nmr experiments and shown to have structure 2a. The HMBC spectrum shows a diagnostic 3-bond C,H coupling between the one proton vinylic singlet (H-3) at 7.2 ppm and the isobutyl side chain methylene carbon at 56.7 ppm which is only possible if the double bond is endocyclic. The ROESY spectrum shows cross-peaks between the singlet at 7.2 ppm and both the isobutyl methylene doublet at 3.8 ppm and the 2 proton singlet of the CH₂C(O)NH₂ group at 3.6 ppm. Also, there are no cross-peaks with any of the aromatic protons. These analytical results were consistent with structure 2a.

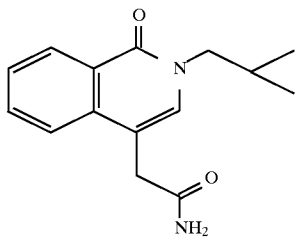

2a

When a substituent was present ortho to the iodo group in 1 (Scheme 4), a mixture of products 2 and 3 was obtained. For example, cyclization of 1d (R=iBu, X=5-methyl) gave a mixture of 2d (retention time=20.16 by HPLC) and 3d (r.t.=21.33 min by HPLC) in a ratio of 1:3.2. The 1H nmr of 2d was very similar to that of 2a (H-3 at 7.18 ppm) whereas 3d showed a corresponding one proton singlet at 6.2 ppm. The assignment of structure 3d to the major isomer was confirmed by HMBC/HMQC and ROESY. The ROESY experiment was particularly informative as it showed a strong NOE cross-peak between the singlet at 6.2 ppm and the aromatic methyl at 2.5 ppm. This indicates that the vinylic proton is located on an exocyclic double bond which is in the Z double bond geometry.

Compound 4, (Scheme 4, methyl group at C-3, R=phenylethyl) was prepared using 4-iodo-2-pentenoic acid as the unsaturated submonomer according to Scheme 4. 4-iodo-2-pentenoic acid was synthesized by Finkelstein reaction of 4-bromo-2-pentenoic acid according to Blenderman, W. G. et al. ((1983) J. Org. Chem. 48:3206–3213). Using the same conditions for cyclization as in the synthesis of compound 2a, compound 4 was obtained exclusively as the exocyclic isomer.

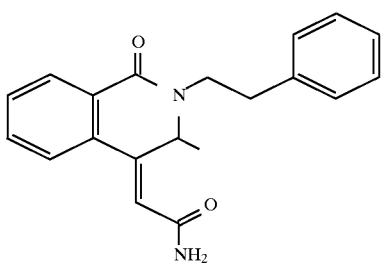

4

The Heck reaction was also successfully extended to the synthesis of compound 5 using 4-bromo-pentenoic acid as the first submonomer and 2-bromopyridine-3-carboxylic acid as the second submonomer, each reacted under the same conditions as described for the synthesis of compound 2a.

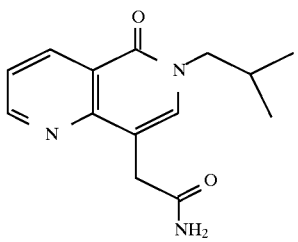

5

Extensions to other o-haloheteroaryl carboxylic acids can readily be imagined. The method of the invention was equally successful when a solid support was derivatized with a dipeptoid prior to reaction with the submonomers which formed the cyclic backbone. Such a reaction produces an isoquinolinone with an extended side chain. Extended hybrid peptoid/isoquinolinones have a larger number of variable substituents: R1 (representing peptoid sidechains derived from amine submonomers), R2 (representing ring substituents derived from amine or alkenoic acid submonomers), and X (representing aromatic substituents derived from an acid halide submonomer).

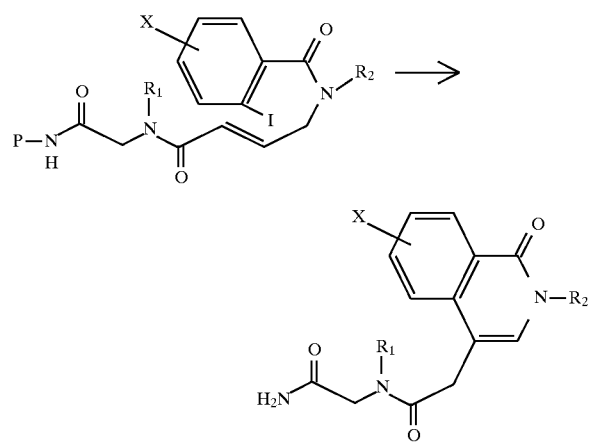

The feasibility of synthesizing a mixture of substituted isoquinolinones was demonstrated when these conditions were extended to monopeptoids containing several different amine-derived side chains as well as different aromatic substitution patterns. The results are shown in Table VIII for reactions performed on a scale of between 100 to 500 mg of polystyrene solid support resin (0.05–0.25 mmol).

TABLE VIII

Characterization of various individual 2-substituted 1-(2H)-isoquinolinones.

| Entry | Ring A | R | Purity (2/3)[a] | Yield[b] |
|---|---|---|---|---|
| 2a | H | iBu | 83 | 69 |
| 2b | H | CH$_2$CH$_2$Ph | 80 | 65 |
| 2c | H | Ph | >70 | 85 |
| 2d | 5-Me | iBu | 94 (1/3.2) | 92 |
| 2e | 8-F | iBu | 90 | 80 |
| 2f | 6,7-diOMe | iBu | 95 | 77 |
| 2g | 7-Cl | iBu | 90 | 79 |
| 2h | 5-OMe | iBu | 93 (1.7/1) | 69 |

[a]Determined by C-18 HPLC monitored at 214 nm. Values in parentheses are ratios of 2 to 3, otherwise only 2 was observed.
[b]Yield of crude product after lyophilization from acetic acid.

Figure 2:
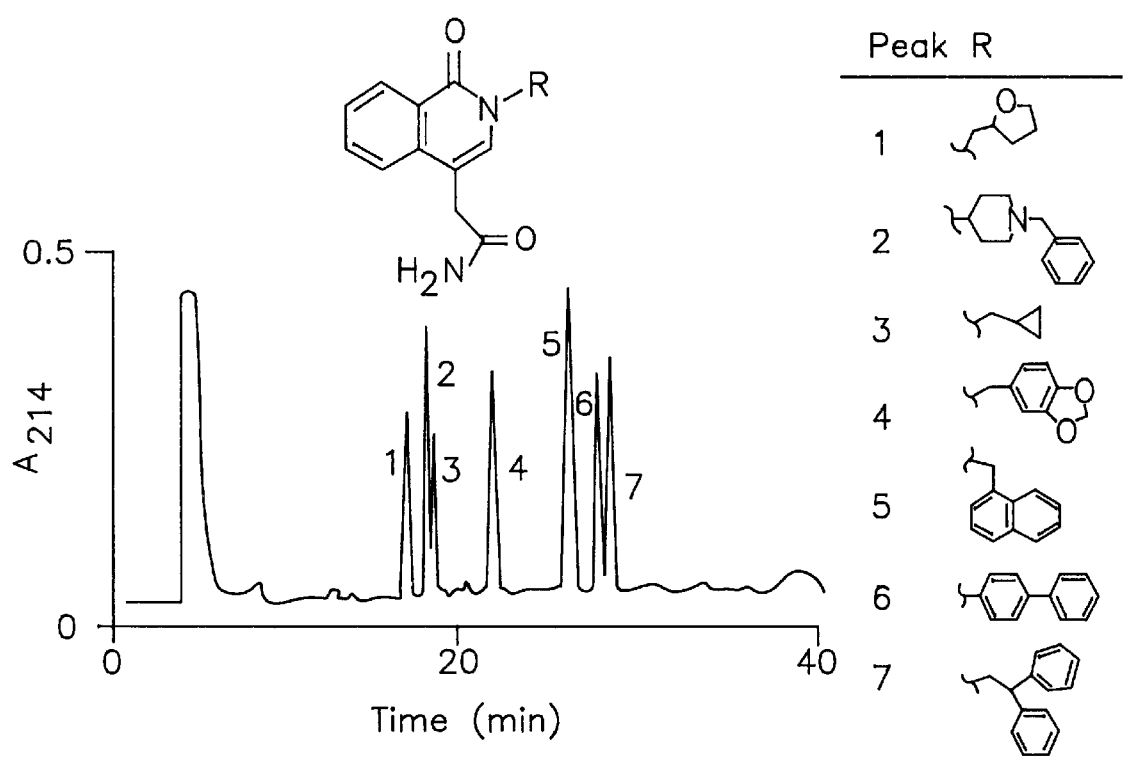
FIG. 2 is a diagram of a representative high pressure liquid chromatogram of a mixture of isoquinolinones according to the invention. The diagram represents a reverse-phase HPLC chromatogram of a seven-component mixture of 2-substituted 1-(2H)-isoquinolinones synthesized via an intramolecular Heck reaction on a solid-support.

A library of 2-substituted 1-(2H)-isoquinolinones having different cyclic R groups was prepared (see general structure, FIG. 2). Seven monopeptoids bearing different amine side chains (R2) were separately synthesized by the submonomer method. The solid support particles were mixed together to make a mixture equimolar in each monopeptoid. The combined, solid support-bound monopeptoids were then acylated in a single reaction mixture with o-iodo-benzoyl chloride.

The resulting compounds were then cyclized by Heck reaction in a single reaction mixture. The cyclized products were cleaved from the solid support particles. The mass spectrometry data of the crude mixture showed all of the parent ions expected from the seven predicted products. HPLC analysis of the crude cleavage mixture is shown in FIG. 2. The identities of the seven major peaks in the HPLC chromatogram were established individually by electrospray mass spectrometry to be the predicted products. It can readily be seen that the substituents on the submonomers used in the reactions determines the variety of different cyclic peptoid-derived compounds in the mixture.

The peptoid portion of the molecule can be rapidly assembled from readily available and highly diverse building blocks by robotic synthesis (Zuckermann, R. N. et al. (1992) Int. J. Pept. Protein Res. 40:497–506). This makes possible the synthesis of designed libraries containing $10^3$–$10^4$ different and distinct members.

Table IX lists several additional peptoid-derived highly substituted 1-(2H)-isoquinolinones obtained by the method of the invention. The compounds in Table IX were obtained from a variety of amines to provide the substituents indicated.

TABLE IX 1-(2H)-Isoquinolinones Prepared by the Submonomer Method

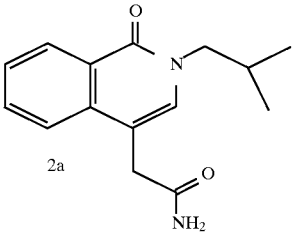
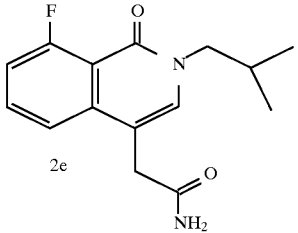
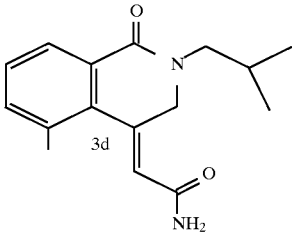
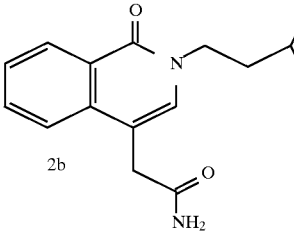
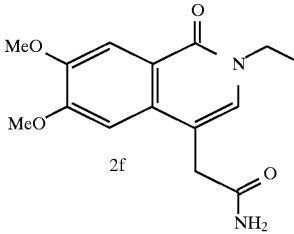
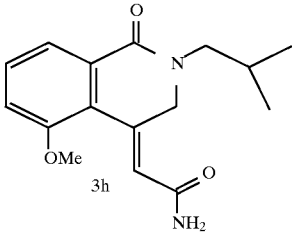
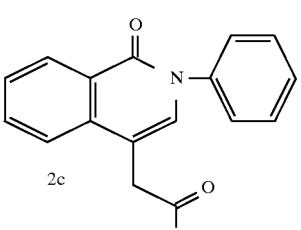
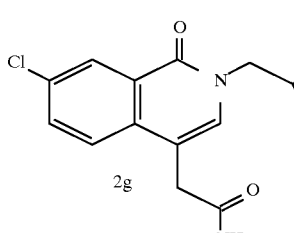
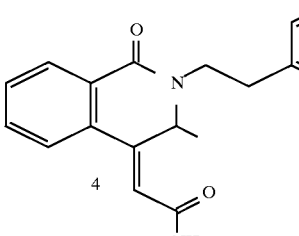

TABLE IX-continued 1-(2H)-Isoquinolinones Prepared by the Submonomer Method

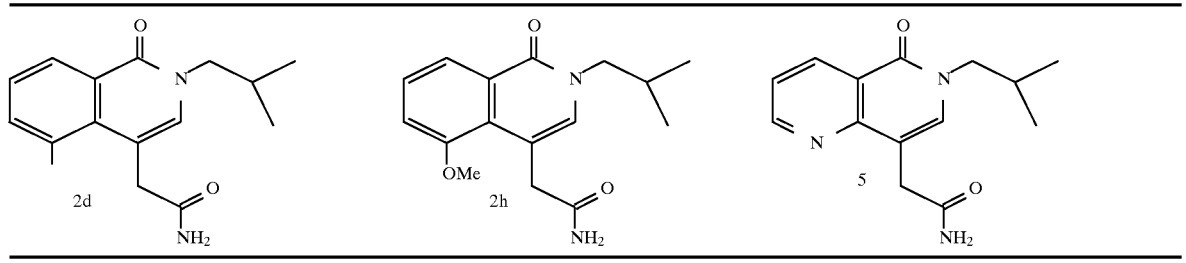

All of the compounds in Table IX were successfully synthesized as established by mass spectrometry and nmr, with isolated crude yields between 50% and 90%, and purities greater than 80% by HPLC analysis. The molecular formula and mass spectrometry data of the product compounds obtained were consistent with the expected structures shown in Table IX. As a general example, a representative experimental procedure for the synthesis (following Scheme 4) of compound 2. is described below.

Rink amide resin (approximately 3 gm, Advanced Chemtech, approximately 0.5 mmol/gm substitution) was placed in a 250 mL capacity silanized glass reaction vessel and swollen in approximately 50 mL of dimethylformamide (DMF) for approximately 5 min. The solvent was drained and the solid support resin was mixed 2×20 min with 30 mL of 20% v/v piperidine in DMF on an orbital shaker at 200 rpm. The solvent was drained and the solid support was washed 6×50 mL with DMF. The deprotected solid support was then treated 2×30 min with a solution of 4-bromo-2-butenoic acid (15 mmol) and diisopropylcarbodiimide (15 mmol) in DMF (25 mL). The acylated solid support was then washed 1×100 mL and 2×50 mL with DMF. Isobutyl amine (4.4 gm, 60 mmol) in DMSO (30 mL) was added. After two hours mixing under argon, the vessel was drained and the solid support washed well with DMF, then $CH_2Cl_2$, followed by drying in vacuo overnight at room temperature. A 140 mg portion of this solid support was loaded into a reaction vessel and placed on a Symphony Multiple Peptide Synthesizer (Protein Technologies, Inc.) and treated first with a solution of freshly prepared 2-iodo-6-fluorobenzoyl chloride (2.4 mmol) in 1,2-dichloroethane (1,2-DCE) (2 mL) followed by treatment with a solution of $Et_3N$ (2.4 mmol) in 1,2-DCE (2 mL). After 30 min of mixing, the vessel was drained and the acylation repeated. The solid support was washed well with DMF and 1,2-DCE and an aliquot was treated with 95/5 v/v $TFA/H_2O$ for 20 min at room temperature for HPLC analysis. The remainder of the solid support was loaded into a 10 mL Schlenk tube and treated with $Pd(Ph_3P)_4$ (35 mg), anhydrous NaOAc (75 mg), $Ph_3P$ (35 mg) and anhydrous N,N-dimethylacetamide (8 mL). A gently vacuum was pulled on the tube for 2 min, then argon gas was introduced. The sealed tube was then placed in a preheated 90° C. block heater and mixed at 200 rpm on an orbital shaker for 6 hr. The solid support was then filtered off and washed with DMF, $H_2O$, DMF and then stirred in a solution of sodium diethyldithiocarbamate (100 mg) in DMF (5 mL) for approximately 10 min to remove residual Pd (Kates, S. A. et al. (1993) Anal. Biochem. 212:303–310). The solid support was again filtered and washed with DMF, THF, $CH_2Cl_2$ and then cleaved with 95/5 $TFA/H_2O$ for 20 min. The cleavage mixture was diluted with HOAc and $H_2O$ and analyzed by HPLC. The mixture was lyophilized, then relyophilized from HOAc to give 16.5 mg of compound 2e.

Example 20

Solid-phase Synthesis of Highly Substituted Tetrahydroisoquinolines by the Submonomer Method The versatility of the submonomer method for generating a diversity of cyclic compounds is illustrated by the ability to simply alter the submonomers used in the method for the production of tetrahydroisoquinolines. In this example, highly substituted tetrahydroisoquinolines are prepared by the submonomer method of the invention using the same reaction conditions as for the synthesis of isoquinolinones described in Example 19. It is noted that each starting monopeptoid and each submonomer of the synthesis represents one or a mixture of each such compound.

In a specific example, solid support particles are derivatized with a monopeptoid according to the submonomer method described herein. A 4-bromo-pentenoic acid submonomer is first reacted with the monopeptoid followed by reaction with a primary amine such as o-iodo-benzylamine. Application of Pd(0)-catalyzed intramolecular cyclization via the Heck reaction results in production of tetrahydroisoquinolines (Scheme 5). If a secondary benzylamine is used, the second substituent will be on the nitrogen of the peptoid-derived ring. Examples of second substituents or caps include, but are not limited to, a peptoid chain, a carbamate, an amide, an ester, a urea, a sulfonamide, thiourea, alkyl, aryl, a peptide, and the like. Alternatively, the "CAP" can be a protecting group which can be removed after the Heck cyclization and then further functionalized. Such peptoid-derived ring nitrogen substituents add another level of diversity to the types of compounds that can be synthesized by the submonomer method.

The size of the peptoid derived ring can be increased by using an amine submonomer having a longer alkyl chain between the nitrogen and the aromatic ring. The size of the peptoid-derived ring is limited only by the structural constraints of intramolecular ring closure.

Examples of tetrahydroisoquinolines that can be synthesized by the submonomer method include, but are not limited to, the general structure produced in Scheme 5 below.

Scheme 5
Synthesis of Tetrahydroisoquinoline by the Submonomer Method

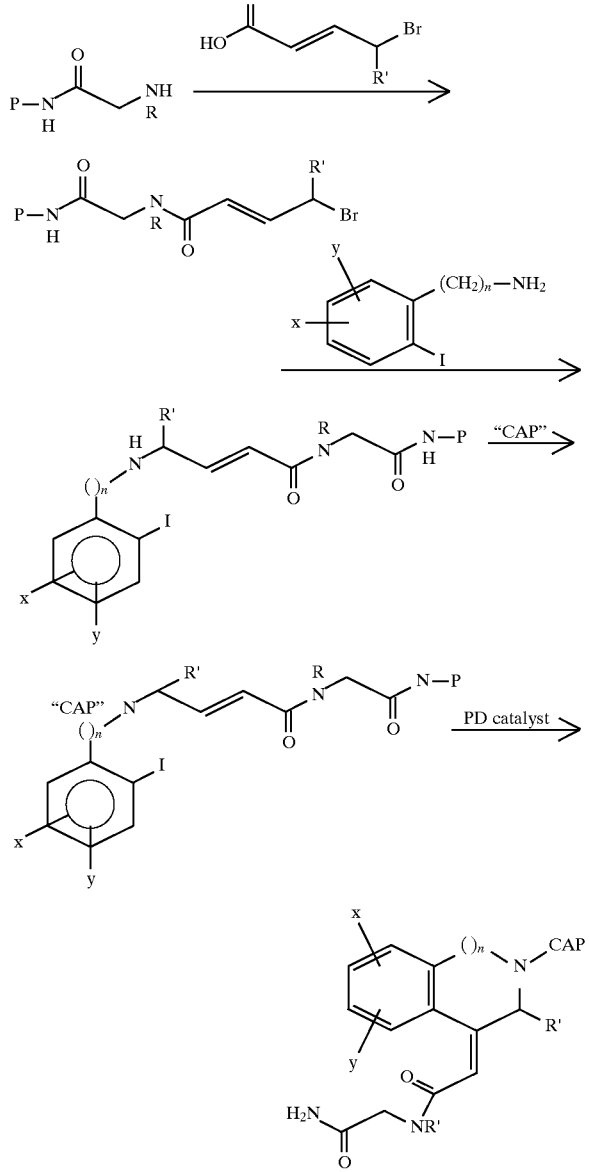

where R is derived from a primary amine and R' can be alkyl, aryl, peptide, peptoid, ketone, amide, ester, or the like; n=1, 2, or 3; and X, Y=alkyl, aryl, halo, or the like.

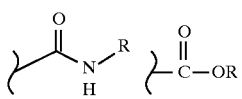

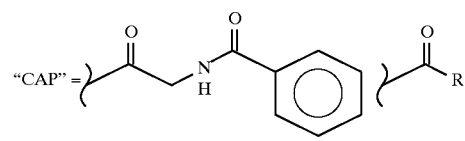

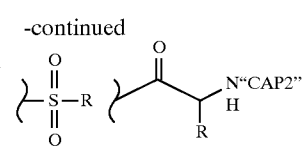

Example 21

Solid-phase Synthesis of Highly Substituted Dihydroisoquinolinone Compounds by the Submonomer Method Dihydroisoquinolinone compounds are readily synthesized by the submonomer method by a variation of the steps described in the previous examples. Peptoid-derivatized solid support particles are first reacted with an amine (having an electrophilic substituent) as the first submonomer and an alkenoic acid chloride as the second submonomer. As in previous examples, the submonomers added after preparation of the peptoid derivatized solid support are the submonomers which make up the ring backbone of the cyclized product. Intramolecular cyclization via the Heck reaction displaces the electrophile of the amine submonomer to form a six-membered ring according to the scheme shown below. In the example, the double bond of the alkenoic acid is retained and the position of the substituent on the double bond can be either cis or trans (Scheme 6).

According to this example, the various substituents on the peptoid-derived ring, on an aromatic ring derived from the acid chloride, and other possible substituents can be any of the substituents described above. As in all of the possible cyclic compounds described herein, the peptoid chain to which the ring structure is attached may be any linear, branched, or cyclic peptoid that can be prepared by the submonomer method of the invention. The cyclic compounds produced by the example are optionally cleaved from the solid support particle at the site of attachment of the peptoid sidechain to the support particle.

Scheme 6

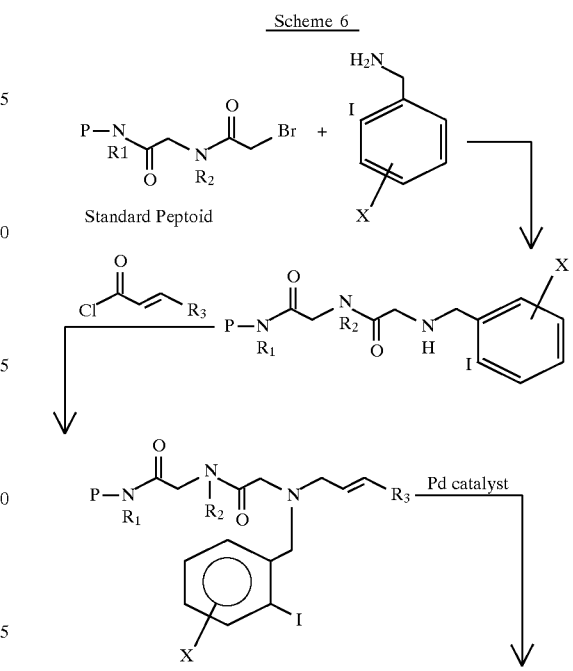

-continued
Scheme 6

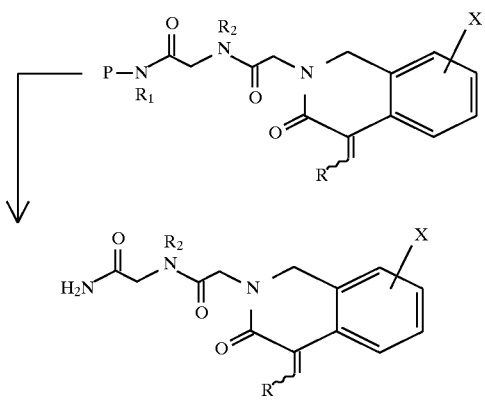

The synthesis of a benzazepinone is accomplished using the submonomer method with, for example, 4-bromopentenoic acid as the first submonomer followed by reaction with a primary amine as the second submonomer (see Scheme 7). An o-iodo- or o-4-bromo-aryl acetic acid halide or o-iodo- or o-bromo-arylacetic acid is the final submonomer added to the peptoid chain. Intermolecular cyclization by the Heck reaction produces a benzazepinone.

Scheme 7

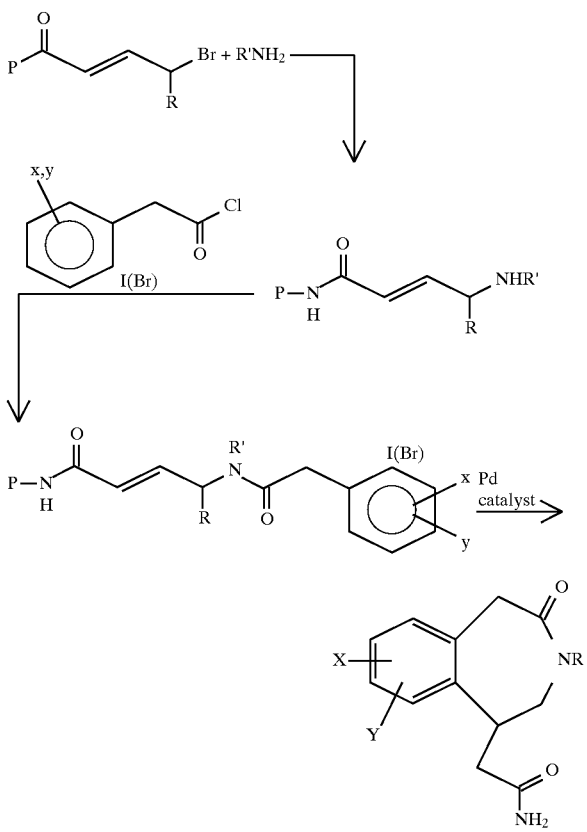

Example 22
Solid-Phase Synthesis of Highly Substituted Dihydroisoquinolinones by the Submonomer Method Dihydroisoquinolin-3-ones were also prepared by the submonomer method as follows. Rink amide solid support resin (150 mg) was deprotected with 20% piperidine in DMF (1×5 min), 1×20 min). The solid support was then acylated with 0.6M bromoacetic acid and 0.6M DIC in DMF (2×30 min). The solid support was then aminated with isobutylamine, 2M in DMSO for 2 hr at room temperature. The solid support was again acylated with bromoacetic acid and then aminated with 2-iodobenzylamine in DMSO for 2 hr at room temperature. The resulting dipeptoid was then acylated by treatment with equal volumes of trans-crotonyl chloride (0.6M) and triethylamine (0.6M) in 1,2-dichloroethane (2×30 min). The solid support was then washed with DMF and dichloromethane and dried in vacuo. The solid support was then placed in a Schlenk tube with N,N-dimethylacetamide (5 mL), tetrakis(triphenylphosphine)palladium (0) (35 mg), anhydrous sodium acetate (75 mg), and triphenylphosphine (35 mg) and briefly degassed. The mixture was then heated at 90°–95° C. for 8 hr under Ar. The solid support was washed with DMF and dichloromethane and then stirred with a solution of sodium diethyldithiocarbamate in DMF for 10 min, then filtered and washed with DMF and dichloromethane and treated with 95/5 TFA/water for 20 min at room temperature. The desired dihydroisoquinolin-3-one was observed as the major product by C18 HPLC having a retention of time of 22.9 min, m/e=344.2 as expected for $C_{19}H_{25}N_3O_3$. Semipreparative HPLC separated two major fractions which were analyzed by proton nmr to show the expected peaks for each of the two double bond isomers of the desired cyclic dihydroisoquinolin-3-one.

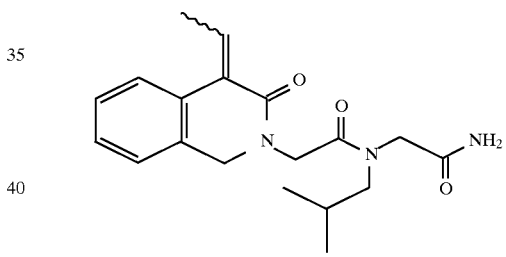

Synthesis of benzazepinone derivatives by the submonomer method was further exemplified by the following. Rink amide solid support resin (150 mg) was deprotected with 20% piperidine in DMF (1×5 min, 1×20 min) and then coupled with 0.6M trans-4-bromo-2-butenoic acid and 0.6M DIC in DMF (2×30 min) at room temperature. The solid support was then treated with 2M phenethylamine in DMSO for 2 hr at room temperature. The solid support was then acylated with 0.6M 4,5-dimethoxy-2-iodophenylacetic acid and 0.6M DIC in DMF (2×30 min, RT). The solid support was washed with DMF and dichloromethane and dried in vacuo. It was then placed in a Schlenk tube with 5 mL of N,N-dimethylacetamide, tetrakis(triphenylphosphine)palladium(0) (35 mg), anhydrous sodium acetate (75 mg) and triphenylphosphine (35 mg). After brief degassing in vacuo, the mixture was heated at 90° C. under Ar for 6.5 hr. The solid support was washed with DMF and dichloromethane and then treated with 95/5 TFA/water for 20 min.

HPLC analysis of the crude reaction mixture showed a major peak containing the endo and exo-double bond isomers as determined by nmr.

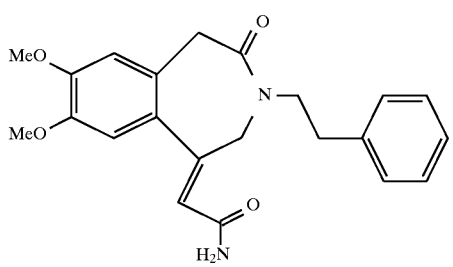

Example 23

Synthesis of Highly Substituted Tetrahydroisoquinolines by the Submonomer Method Synthesis of a tetrahydroisoquinoline product was performed by the submonomer method as follows. Rink amide solid support (150 mg) was deprotected with 20% piperidine in DMF (1×5 min, 1×20 min). The solid support was then washed with DMF and treated with 0.6M bromoacetic acid and 0.6M DIC in DMF (2×30 min). The solid support was again washed with DMF and then coupled with 0.6M trans-4-bromo-2-butenoic acid and 0.6M DIC (2×30 min). The solid support was washed with DMF and then treated with 2M 2-iodobenzylamine in DMSO for 2 hr at room temperature. The resulting dipeptoid was then acylated with 0.6M hippuric acid and 0.6M DIC in DMF (2×30 min, 1×1 hr). This capped intermediate had a C18 HPLC retention time of 27.11 min and gave the expected electrospray protonated parent ion at m/e=591.2 ($C_{26}H_{31}N_4O_4I$). The solid support was then placed in a Schlenk tube with tetrakis(triphenylphosphine)palladium(0) (35 mg), anhydrous sodium acetate (75 mg), and triphenylphosphine (35 mg), and anhydrous N,N-dimethylacetamide (5 mL). After degassing in vacuo, the mixture was heated at 90° C. for 8 hr under Ar. The solid support was washed with DMF and dichloromethane and then cleaved from the solid support with 95/5 TFA/water for 20 min at room temperature. The major component of the crude reaction mixture was the desired tetrahydroisoquinoline having an m/e=463.3 (FAB) as expected for $C_{26}H_{30}N_4O_4$.

tetrahydroisoquinoline

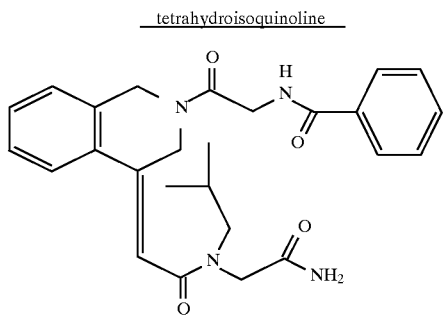

Preparation of another tetrahydroisoquinoline by the submonomer method is exemplified by the following synthesis. Rink amide solid support resin (150 mg) was deprotected with 20% piperidine in DMF (1×5 min, 1×20 min). The solid support was then acylated with 0.6M bromoacetic acid and 0.6M DIC in DMF (2×30 min). The solid support was then aminated with isobutylamine, 2M in DMSO for 2 hr at room temperature. The solid support was acylated with bromoacetic acid and then aminated with 2-iodobenzylamine in DMSO for 2 hr at room temperature. The resulting dipeptoid was then alkylated by treatment with a solution of allyl bromide (0.34 mL) and diisopropylethylamine (0.10 mL) in DMSO (4 mL) overnight at room temperature. The solid support was then placed in a Schlenk tube with N,N-dimethylacetamide (5 mL), tetrakis(triphenylphosphine)palladium (0) (35 mg), anhydrous sodium acetate (75 mg), and triphenylphosphine (35 mg) and briefly degassed. The mixture was then heated at 90°–95° C. for 8 hr under Ar. The solid support was washed with DMF and dichloromethane and then stirred with a solution of sodium diethyldithiocarbamate in DMF for 10 min, then filtered and washed with DMF and dichloromethane and treated with 95/5 TFA/water for 20 min at room temperature. The desired dihydroisoquinoline was observed as the major product by C18 HPLC having a retention of time of 17.8 min, m/e=316.1 as expected for $C_{18}H_{25}N_3O_2$. Proton nmr of the crude product showed a single isomer and the two vinylic protons were observed as two doublets at 5.3 ppm and 5.9 ppm.

tetrahydroisoquinoline

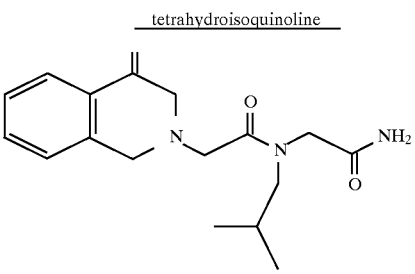

Example 24

Solid-Phase Synthesis of Benzazepines by the Submonomer Method

By a submonomer synthesis procedure similar to that described herein for tetrahydroisoquinolines, the synthesis of 3-benzazepines was performed. Rink amide solid support resin (150 mg) was deprotected with 20% piperidine in DMF (1×5 min, 1×20 min). The solid support was then acylated with 0.6M bromoacetic acid and 0.6M DIC in DMF (2×30 min). The solid support was then aminated with 4,5-dimethoxy-2-iodophenethylamine, 2M in DMSO for 2 hr at RT.

The resulting peptoid was then alkylated by treatment with a solution of 1.0M allyl bromide in DMSO (4 mL) overnight at RT. The solid support was then washed with DMF and dichloromethane and dried in vacuo. The solid support was then placed in a Schlenk tube with N,N-dimethylacetamide (5 mL), tetrakis(triphenylphosphine)palladium(0) (35 mg), anhydrous sodium acetate (75 mg), and triphenylphosphine (35 mg) and briefly degassed. The mixture was then heated at 90°–95° C. for 7.5 hr under Ar. The solid support was washed with DMF and dichloromethane and then treated with 95/5 TFA/water for 20 min at RT. The desired 3-benzazepine was observed as the major product by HPLC with an m/e=277.1 as expected for $C_{15}H_{20}N_2O_3$. The proton nmr indicated that a single cyclic compound was formed and that the double bond was exo to the ring.

3-benzazepine

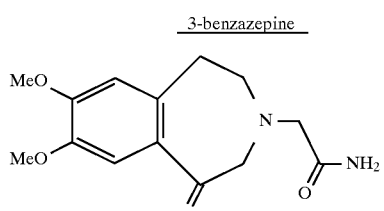

Example 25

Solid-phase Synthesis of Highly Substituted Phenanthridones by the Submonomer Method The ability of the submonomer method to generate compounds having three fused rings is demonstrated by the synthesis of phenanthridones (Scheme 8) where X and Y are any aromatic ring substituents. In a specific example of such a synthesis, monopeptoid-derivatized solid support particles were reacted with a substituted aromatic primary amine. This reaction was followed by reaction with an o-iodobenzoic acid chloride. The aromatic substituents X' and Y' were any substituents which did not interfere or compete with either the acid chloride displacement during peptoid backbone synthesis or with aromatic iodide displacement during subsequent cyclization. Intramolecular cyclization via the Heck reaction produced a phenanthridone having three fused rings, aromatic substituents and a peptoid sidechain. It is readily seen that a wide variety of compounds is synthesized by varying the submonomers of the reactions. Further, according to the method of the invention, libraries of such compounds can be made by portioning and recombining the solid support particles at desired submonomer reaction steps. The product compounds are optionally cleaved from the solid support following the preparation. Cleavage preferably occurs at the site of attachment of the peptoid sidechain to the solid support particle.

Scheme 8

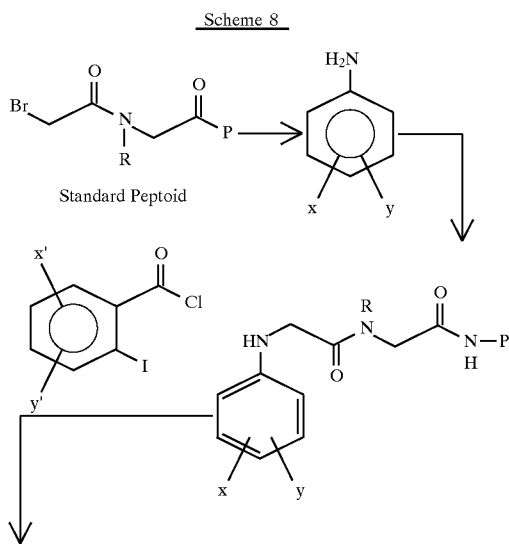

-continued
Scheme 8

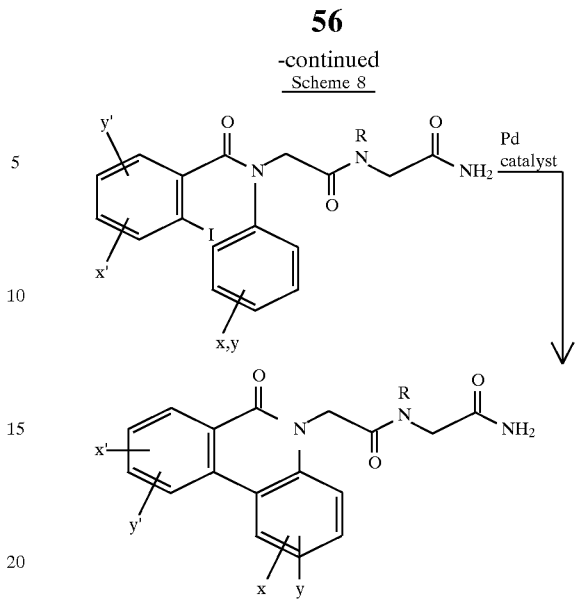

Preparation of phenanthridones by the submonomer method is further exemplified by the following synthesis (see Scheme 9). Compound A (R=isobutyl; Scheme 9) was prepared according to the submonomer method of peptoid synthesis. The solid support resin (155 mg) was treated for 2 hr at room temperature with 3 mL of a solution of 2M 3-aminobenzotrifluoride in DMSO (X=EWG=3-$CF_3$) or with 2M 2-ethylaniline (X=electron donating group=2-Et) in DMSO. Each solid support resin was washed with DMF and 1,2-dichloroethane (1,2-DCE) and then treated twice for 30 min with 2 mL of 1.2M o-iodobenzoyl chloride in 1,2-DCE and 2 mL of 1.2M triethylamine in 1,2-DCE. Acylated solid support resins C were washed with DMF and dichloromethane and dried overnight in vacuo. Aliquots of each solid support were cleaved with 95/5 TFA/water and analyzed by C18 HPLC. Cleaved compound C, X=3$CF_3$ had a retention time of 31.3 min and gave the expected protonated parent ion (m/e=562.3) while for X=2-Et, the retention time was 30.3 min, and m/e=522.3 as expected. Each batch of solid support was then placed in a schlenk tube and treated with anhydrous sodium acetate (80 mg), triphenylphosphine (40 mg), tetrakis(triphenylphosphine)palladium(0) (40 mg) and N,N-dimethylacetamide (8 mL). The mixture was briefly degassed in vacuo and argon gas was introduced, followed by heating at 120° C. for 3.25 hr. The cooled reaction mixtures were filtered and the solid support washed with DMF, water, DMF and dichloromethane. The solid support resins were then stirred for 10 min with 5 mL of a solution of sodium diethyldithiocarbamate (100 mg). The solid supports were then washed with DMF and dichloromethane, followed by treatment with 95/5 TFA/dichloromethane at room temperature for 20 min. For the product compound in which X was an electron withdrawing group (EWG) such as trifluoromethyl, the phenanthridone, compound E of Scheme 9, was obtained having the following expected characteristics: C18 HPLC retention time=29.6 min, m/e=434.2; the structure was confirmed as a mixture of the two possible regioisomers by proton nmr. For the case in which X was an electron-donating group (EDG) such as 2-Et, compound F was the major product. The loss of the N-R side chain was complete with increased acidity of the cleavage medium or with increased cleavage time. Compound F, where X=2-Et, had a C18 HPLC retention time of 27.1 min and showed the expected m/e=282.2. The structure was confirmed by proton nmr. Using the submonomer method as in this example, phenanthridones having general structure, F, were also obtained from 3-ethylaniline, o-anisidine, and m-anisidine.

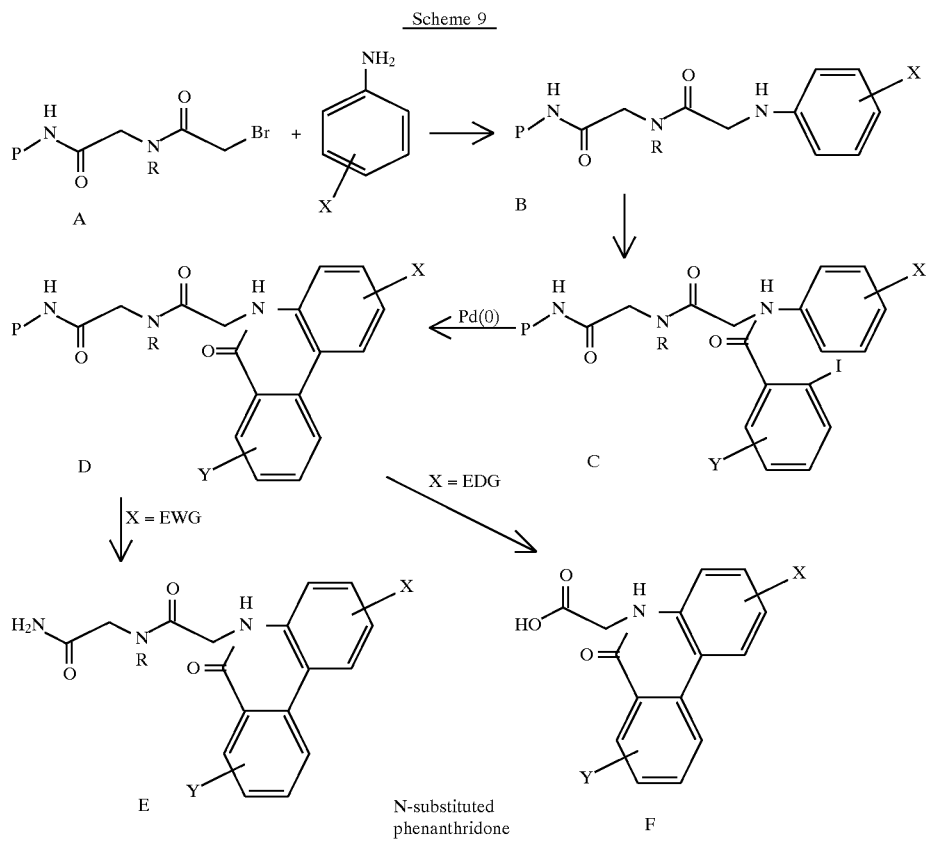

Scheme 9

Example 26

Solid-phase Synthesis of Highly Substituted Monoketopiperazines by the Submonomer Method Synthesis of six-membered ring derivatives is accomplished by obtaining monopeptoid-derivatized solid support particles according to the submonomer method. An alkenoic acid such as 4-bromo-pentenoic acid is reacted with the monopeptoid. The product of this reaction is then reacted with a primary or secondary amine to produce an intermediate product for use in the synthesis of 6-membered peptoid-derived ring products.

For the synthesis of a monoketopiperazine, the above intermediate is reacted with an α-bromo carboxylic acid, for example, followed by reaction with a primary amine (Scheme 10). Subsequent cyclization via an intramolecular Michael addition produces a monoketopiperazine as shown below. The substituents can be any of the substituents described in previous examples herein.

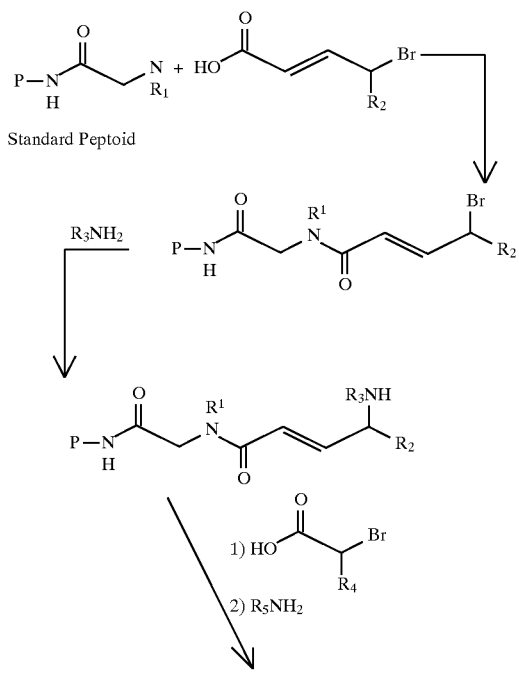

Scheme 10

59
-continued
Scheme 10

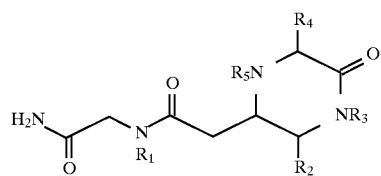

For the synthesis of a monoketopiperazine with a different substituent pattern, the peptoid intermediate is reacted with a carboxylic acid submonomer having a protected amine substituent. In the example below (Scheme 11), the amino group is protected by any appropriate protection group (PG) well known in the art of peptide synthesis such as Fmoc, Boc, and the like. Deprotection of the amine substituent followed by cyclization produces a 6-membered monoketopiperazine analog. If desired, the unsubstituted nitrogen on the ring may be derivatized following cyclization. Alternatively, such a derivative can be introduced as a component of the carboxylic acid submonomer, for example, as an N-acylated α-amino acid.

Scheme 11

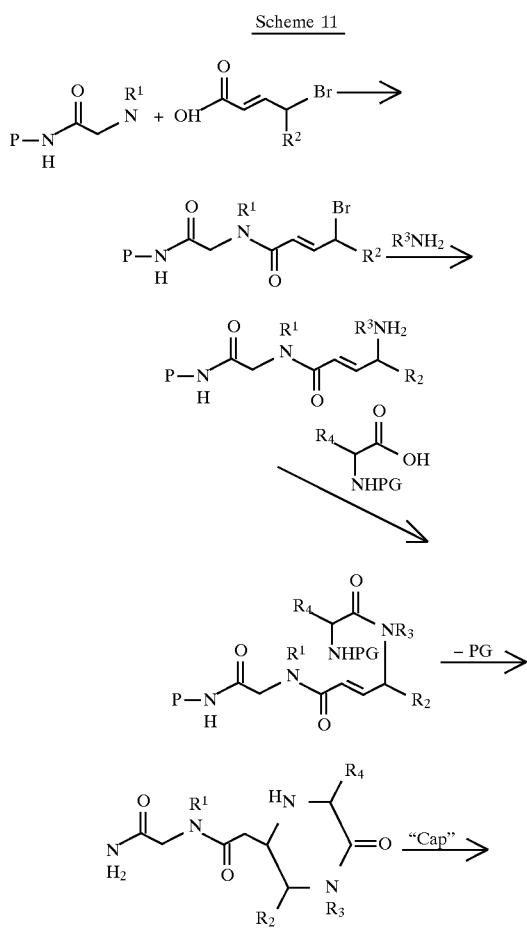

60
-continued
Scheme 11

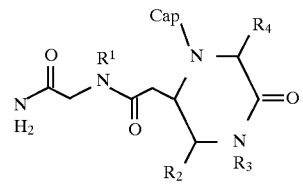

These submonomer reactions can be varied to produce numerous other products by simple variations in the substituents. Any of the R-groups can contain substituents which will undergo subsequent reactions, thereby increasing the variety of compounds that are produced by the submonomer method. The product compounds can be cleaved from solid support particles as for linear peptoids.

Additionally, the monoketopiperazine ring system can undergo further reactions to produce more complex ring structures (Scheme 12). For example, the monoketopiperazine is reacted with an aromatic aldehyde in the presence of an acceptor molecule, such as an alkene having an electron withdrawing group (e.g., an EWG such as —NO$_2$, carbonyl, or the like) on the double bond. Other acceptor molecules include, but are not limited to maleimides, alpha, beta-unsaturated ketones, esters, sulfones, alkynes having an EWG on the triple bond, or any molecule that acts as a Michael acceptor or dipolarophile in a [3+2] cycloaddition. The formation of a highly substituted pyrrolidine is a consequence of the cycloaddition reaction. Synthesis of pyrrolidines by the submonomer method is described below in Example 28.

Scheme 12

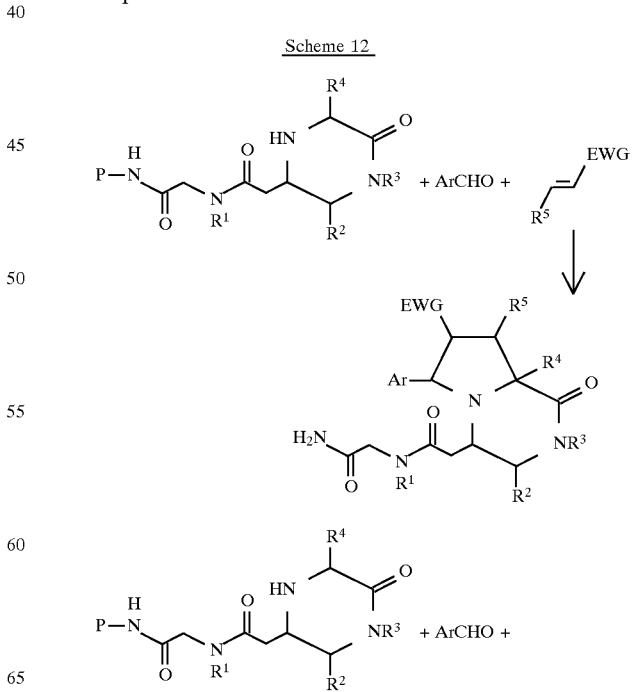

-continued
Scheme 12

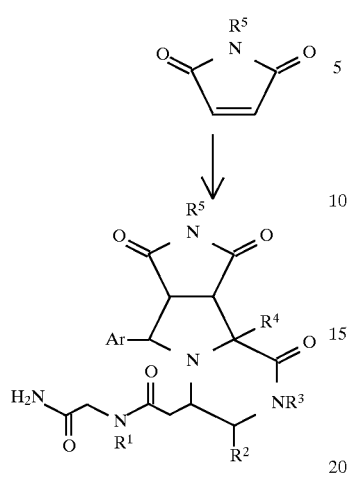

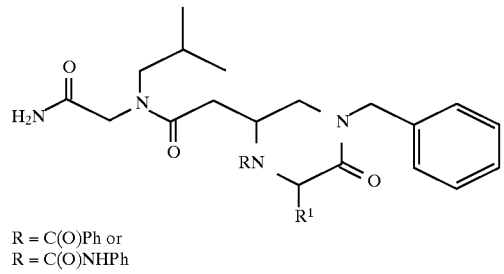

R = C(O)Ph or
R = C(O)NHPh

The preparation of monoketopiperazines by the submonomer method is provided. Rink amide solid support resin (0.51 mmol/gm substitution, 5.7 gm) was swollen in DMF, then treated 1×5 min and 1×20 min with 50 mL of 20% piperidine in DMF. The solid support was washed with DMF, then treated 2×30 min with 0.6M bromoacetic acid and 0.6M DIC in DMF (50 mL). The solid support was washed with DMF, then treated with 50 mL of 2.0M isobutylamine in DMSO for 2 hr at RT. The solid support was washed with DMF and coupled with 0.6M trans-4-bromo-2-butenoic acid and 0.6M DIC in DMF (50 mL) for 2×30 min. The solid support was washed with DMF and dichloromethane and dried in vacuo. The dried solid support (1.5 gm) was swollen in DMF, then treated with a solution of Fmoc-L-alanine (15 mmol), HOBt (15 mmol) and DIC (15 mmol) in DMF (25 mL) at RT for 45 min. The solid support was then washed with DMF and dichloromethane and dried in vacuo.

Two portions of solid support resin (190 mg) were then separately treated with 2.5 mL of 20% piperidine in DMF (1×5 min, 1×20 min) to give the monoketopiperazine, R=H, R1=Me. One portion of solid support was then treated with benzoyl chloride (2.4 mmol) and triethylamine (2.4 mmol) in 1,2-dichloroethane (1,2-DCE) (4 mL, 2×30 min, RT) to give the benzoylated monoketopiperazine (R=C(O)Ph. The m/e=479.3 was as expected for $C_{27}H_{34}N_4O_4$.

The other portion of solid support was treated 2×30 min at RT with a solution of phenylisocyanate (0.6M) and triethylamine (0.6M) in 1,2-DCE (4 mL) to give the urea R=C(O)NHPh. Two major product compounds were observed by HPLC and were identified by nmr to be diastereomers. The mass spectrum m/e=494.3 for both product compounds was as expected for $C_{27}H_{35}N_5O_4$. Other FMOC amino acids successfully used to make monoketopiperazines of this type included proline, phenylalanine, tryptophan, glycine, and valine. The general structure of compounds made in this example is shown below.

Monoketopiperazine libraries have been made from various submonomers. Alpha-halo acids were used as submonomers in the following preparation (Scheme 13). Solid support resin A (140 mg, Scheme 13) was prepared as described in the preceding example and then treated 2×30 min with 0.6M bromoacetic acid and 0.6M DIC in DMF. The solid support was washed with DMF, then treated with 3 mL of 1.0M cinnamylamine in DMSO for 4 hr at RT to give the monoketopiperazine B (R1=H; Scheme 13). A single major product peak was obtained by HPLC and the recovered product had an m/e=477.3 as expected for $C_{28}H_{36}N_4O_3$.

Scheme 13

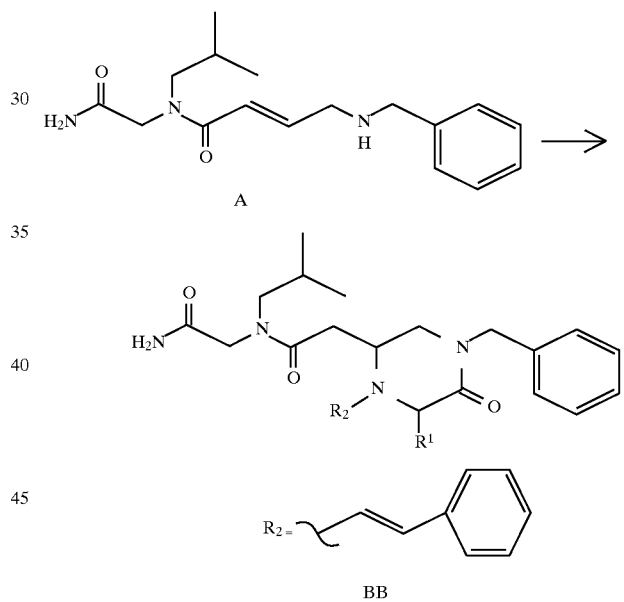

Other primary amines were successfully used in this synthesis in place of cinnamylamine. Bifunctional and heterocyclic primary amines can be used. Diamines were used such that R2=CH$_2$CH$_2$NH$_2$ and R2=CH$_2$Ph(p-CH$_2$NH$_2$). Heterocyclic amines were used such that R2=CH$_2$CH$_2$(2-pyridyl), CH$_2$CH$_2$(3-indolyl), CH$_2$(3-pyridyl), and CH$_2$CH$_2$CH$_2$(N-morpholino). R1 is not limited to H. Compounds were prepared where R1=Me or Ph.

For example, a compound in which R1 and R2 were varied was prepared. Solid support resin A (100 mg, Scheme 13) was treated with S(−) 2-bromopropionic acid (0.6M) and DIC (0.6M) in DMF (2.5 mL, 2×30 min). The solid support was washed with DMF and then treated with 3 mL of 2.0M cyclopentylamine in DMSO for 2 hr at RT to give the monoketopiperazine R=benzyl, R1=Me, R2=cyclopentyl. The product was a mixture of 2 diastereomers as determined by HPLC. The compounds of each peak gave the expected m/e=443.2 for $C_{25}H_{38}N_4O_3$. The structural assignment was confirmed by proton nmr.

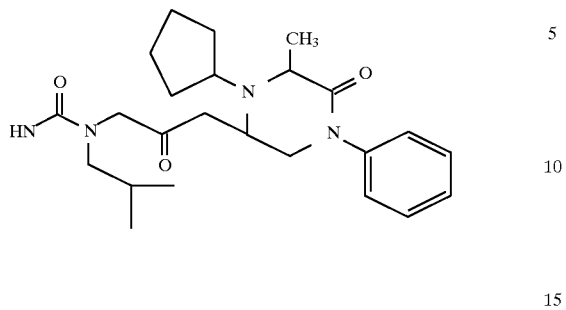

A library of monoketopiperazines was prepared as follows. Solid support resin A (Scheme 14) was prepared by the general procedures described in the previous examples were the R group is derived from one of eight different primary amines. In this example, R is derived from allylamine, cyclopropylmethylamine, aniline, benzylamine, cycloheptylamine, n-hexylamine, 4-aminobiphenyl, and 2,2-diphenylethylamine. The eight different solid supports were mixed together to make a mixed amine solid support. This step is the manual equivalent to a robotic step in an automated submonomer synthesis process. The mixed amine solid support (100 mg) was then acylated with bromoacetic acid (0.6M) and DIC (0.6M) in DMF (4 mL) for 2×30 min. The solid support was washed with DMF and then treated with 2.0M phenethylamine in DMSO (4 mL) for 2 hr at RT, then cleaved by treatment with 95/5 TFA/water to give compound B ($R^1$=H, R=8 various; Scheme 14). Eight product compounds of general structure B ($R^1$=H) were obtained: R=allyl, m/e=415.2; R=cyclopropylmethyl, m/e=429.2; R=Ph, m/e=451.2; R=benzyl, m/e 465.3; R=cycloheptyl, m/e=471.3; R=n-hexyl, m/e 459.3; R=4-biphenyl, m/e=527.3; R=2,2-diphenylethyl, m/e=555.3. Similar libraries were prepared from the same eight amines and 2-bromopropionic acid to give B (Scheme 14) where R1=Me and 2-bromophenylacetic acid to give B (Scheme 14) where R1=Ph.

Scheme 14

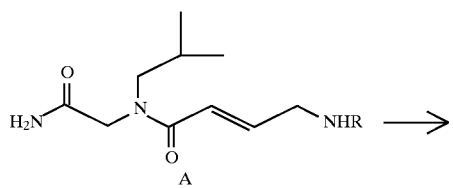

A

-continued
Scheme 14

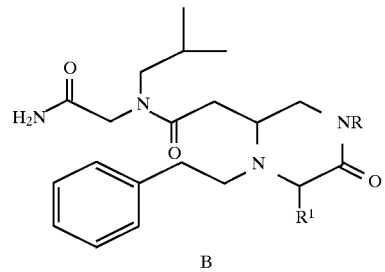

B

Example 27

Solid-Phase Synthesis of Diketopiperazines and Diketomorpholines by the Submonomer method The preparation of a combinatorial library of 2,5-diketo-1,4-piperazine (DKPs) and 3,4,6-trisubstituted-2,5-diketo-1,4-morpholines on solid support from commercially available building blocks using mild conditions is described. The diketopiperazine pharmacophore is found in natural products and has known therapeutic applications such as platelet-activating factor inhibitors (Shimazaki, N. et al. (1987) J. Med. Chem. 30:1706–1711); phytotoxins (Gelin, J. et al. (1993) J. Org. Chem. 58:3473–3475); antagonist of substance P (Barrow, C. J. et al. (1993) J. Org. Chem. 58:6016–6021) and other uses (Chu, M. et al. (1993) Tetrahedron Lett. 34:7537–7540).

A general approach for DKP synthesis on the solid support is illustrated in Scheme 15. Synthesis involves two steps: a) the displacement of a solid support-bound bromide with a primary amine and b) the acylation of a solid support-bound secondary amine with an α-bromocarboxylic acid in the presence of an activating agent. A combination of reaction time (>12 hours), temperature, and an excess of amine is preferred to drive the amine displacement reaction to completion and provide compound 3 in acceptable yield. When reacting sterically hindered, solid support-bound secondary amines, the acylation step (affording compound 5) is preferably performed using THF as the solvent and PyBrop® as the activating agent in the presence of diisopropylethylamine (DIEA). Elevated temperature and increased reaction time can be used to drive the reaction to completion.

Scheme 15
General polymer-supported synthesis of both DKMs and DKPs.
Compound 5 is an intermediate in both syntheses.

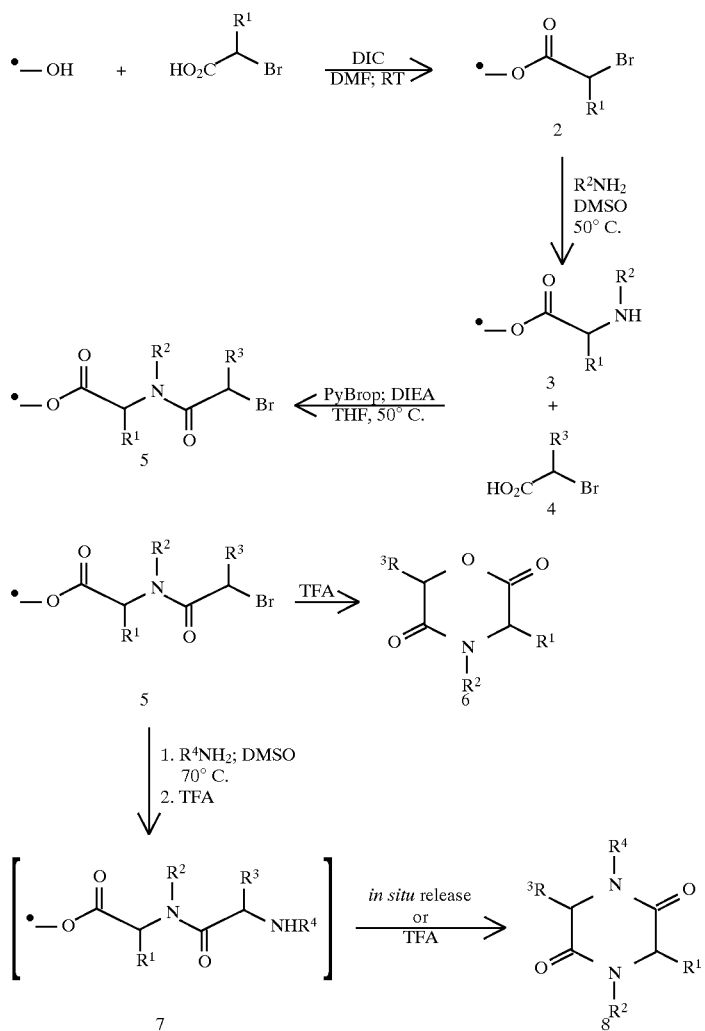

Intermediate compound 5 of Scheme 15 is useful for the synthesis of either diketomorpholines or diketopiperazines. Cyclization of solid support-bound bromides, 5, to form the corresponding DKM (6) is inducible by treatment with TFA (Scheme 15). DKMs prepared in this way were typically found to be a single product or a mixture of diastereomers by HPLC and/or GC/MS. Alternatively, intermediate compound 5 can be treated with a primary amine to displace the bromide and provide DKPs exemplified by compound 8. The resultant solid support-bound compounds 8 are treated with TFA to promote cyclization and release protecting groups (if present) from substituents.

Synthesis of 1-N-Benzyl-4-N-isobutyl-2,5-dioxo-1,4-piperazine. To a slurry of hydroxymethyl solid support resin (0.5 g, 0.25 mmol, loading=0/50 mmol/g) in THF (5 mL) was added bromoacetic acid (104.2 mg, 0.75 mmol) and N,N-dimethylaminopyridine (DMAP) (3 mg, 0.025 mmol). Activating agent, diisopropylcarbodiimide (DIC) (117 μL, 0.75 mmol) was added in one portion to the reaction mixture. The reaction mixture was agitated at room temperature for 30 min., filtered and the acylation repeated. The solid support was filtered and washed with dimethylformamide (DMF) (2×10 mL) and dichloromethane (DCM) (2×10 mL).

Solid support-bound bromide 2 (Scheme 15; $R^1$=H, Scheme 15) was treated with a solution of benzylamine (2M) in dimethylsulfoxide (DMSO) at room temperature for 24 hr. The solid support was filtered and washed with DCM (2×10 mL), methanol (2×10 mL), and DCM (2×10 mL). A standard ninhydrin test confirmed the presence of amine on the solid support.

To a slurry of solid support-bound secondary amine 3 (Scheme 15; $R^1$=H, $R^2$=benzyl; 0.5 g, 0.25 mmol) in DCM (5 mL) was added bromoacetic acid (104.2 mg, 0.75 mmol) and diisopropylethylamine (DIEA) (392 μL, 2.25 mmol). Activating agent, bromotris(dimethylamino) phosphonium hexafluorophosphate (PyBrop) (349 mg, 0.75 mmol) was preferably added to the reaction mixture in one portion. The reaction mixture was agitated at room temperature for 2 hr, filtered, and the acylation repeated with fresh reagents. The resultant solid support 5 was filtered and washed with DMF (2×10 mL) and DCM (2×10 mL). A standard ninhydrin test confirmed that the acylation was complete.

The solid support 5 (Scheme 15; $R^1$=H, $R^2$=benzyl, $R^3$=H, Scheme 15) was treated with isobutyl amine (2M) in DMSO for 21 hr at room temperature. The solid support was drained, washed with DCM (3×10 mL) and the eluents concentrated with a rotary evaporator. The residue was dissolved in ethyl acetate and washed with a solution of 20% acetic acid/water and brine. The organic layers were combined, dried over $Na_2SO_4$ and concentrated with a rotary evaporator to yield the desired diketopiperazine. NMR and GC/MS data were consistent with expected results for the parent compound $C_{15}H_{20}N_2O_2$ (GC/MS, M=260). HPLC: 14 min.

1-N-benzyl-3-ethyl-4-N-(2-methyl)propyl-6-propyl-2,5-dioxo-1,4-piperazine. To a slurry of hydroxymethyl resin (5.0 g, 2.50 mmol, loading=0.50 mmol/g) in DMF (50 mL) was added a-bromovaleric acid (0.984 mL, 7.50 mmol) and DMAP (30 mg, 0.25 wmol). Activating agent, DIC (1.17 μL, 7.50 wmol) was preferably added in one portion to the reaction mixture. The reaction mixture was agitated at room temperature for 30 min., the solid support resin was filtered, and the acylation was repeated to assure complete reaction. The solid support was filtered and washed with DMF (2×10 mL) and DCM (2×10 mL).

Solid support-bound bromide 2 (Scheme 15; $R^1$=propyl) was treated with a solution of benzylamine (2M) in DMSO at 50° C. for 22 hr. The solid support was filtered and washed with DCM (2×10 mL), methanol (2×10 mL), and DCM (2×10 mL) to provide solid support 3 ($R^1$=propyl, $R^2$=benzyl, Scheme 15). A standard ninhydrin test confirmed the presence of amine on the solid support.

To a slurry of solid support 3 ($R^1$=propyl, $R^2$=benzyl; 0.20 g, 0.10 mmol) in THF (2 mL) was added 2-bromobutyric acid (107 μL, 1.0 mmol) and DIEA (348 μL, 2.0 mmol). Activating agent, PyBrop (466 mg, 1.0 mmol) was preferably added in one portion to the reaction mixture. The reaction mixture was agitated at 50° C. until a standard ninhydrin test confirmed that the acylation was complete. The resultant solid support 5 ($R^1$=propyl, $R^2$=benzyl, $R^3$=ethyl, Scheme 15) was filtered and washed with DMF (2×10 mL) and DCM (2×10 mL).

Solid support 5 ($R^1$=propyl, $R^2$=benzyl, $R^3$=ethyl) was treated with isobutyl amine (2M) in DMSO for 24 hr. at 70° C. The solid support was drained, washed with DCM (3×10 mL), and the eluents (containing DKP product cyclized and released from the solid support in situ) were concentrated with a rotary evaporator. The solid support was treated with 95% TFA/5% water for 1 hr. to yield the desired diketopiperazine product cyclized and released from the solid support by TFA treatment (Scheme 15, compound 8, $R^1$=propyl, $R^2$=benzyl, $R^3$=ethyl, $R^4$=isobutyl). The DKP products were combined and analyzed. GC/MS (M) for $C_{20}H_{30}N_2O_2$=330, as expected. HPLC:15.38 min.

3-propyl-4-N-benzyl-6-(1-methyl)ethyl-2,5-dioxo-1,4-morpholine. To a slurry of solid support 3 ($R^1$=propyl, $R^2$=benzyl) from above (1.50 g, 0.75 mmol) in THF (15 mL) was added (±)-2-bromo-3-methylbutyric acid (1.36 g, 7.5 mmol) and DIEA (2.6 mL, 15 mmol). Activating agent, PyBrop (3.5 g, 7.5 mmol) was preferably added in one portion to the reaction mixture. The reaction mixture was agitated at 50° C. until a standard ninhydrin test confirmed that the acylation had gone to completion. The solid support was filtered and washed with DMF (2×10 mL) and DCM (2×10 mL). The resultant solid support 5 (Scheme 15, compound 6, $R^1$=propyl, $R^2$=benzyl, $R^3$=(1-methyl)ethyl) was treated with a solution of 95% TFA/5% water for 1 hr. to provide the desired diketomorpholine. GC/MS (M) for $C_{17}H_{23}N_1O_3$=289, as expected. HPLC: 18.35 min.

Diketopiperazine and diketomorpholine library synthesis. Using the split/mix approach shown in Scheme 16, two libraries were prepared: a) a 3,4,6-trisubstituted-2,5-diketo-1,4-morpholine library consisting of 7 pools of 140 compounds and b) a 1,3,4,6-tetrasubstituted-2,5-diketo-1,4-piperazine library consisting of 23 pools of 980 compounds. Wang solid support resin was divided into 7 equal portions and each portion was treated with an α-bromocarboxylic acid 1 (12 eq; see Table X) in the presence of DIC (13 eq) in DMF. The reaction mixtures were agitated at room temperature for 2 hr., drained, and the reaction was repeated.

Scheme 16
Synthesis of DKM and DKP libraries via the divide-and-combine solid support method.

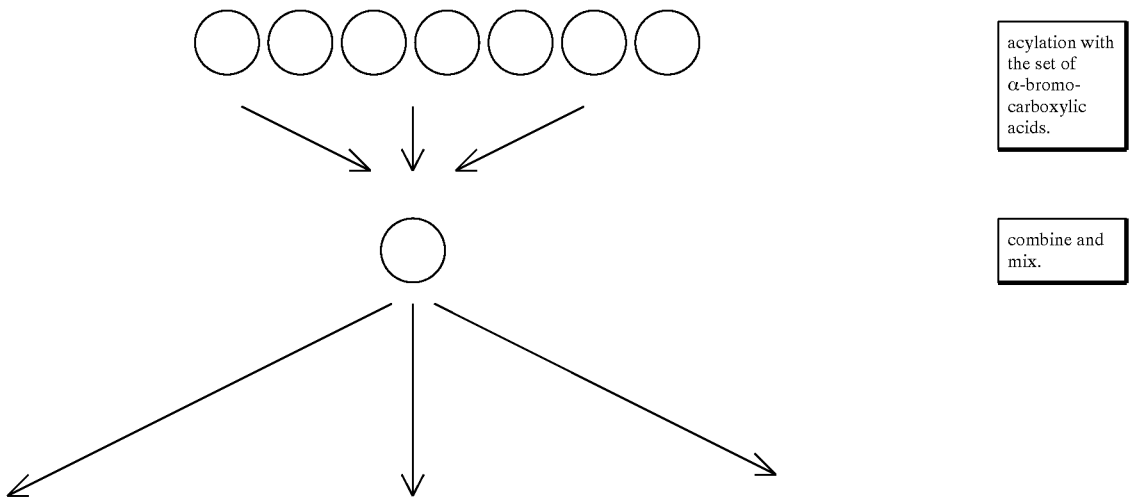

-continued
Scheme 16
Synthesis of DKM and DKP libraries via the divide-and-combine solid support method.
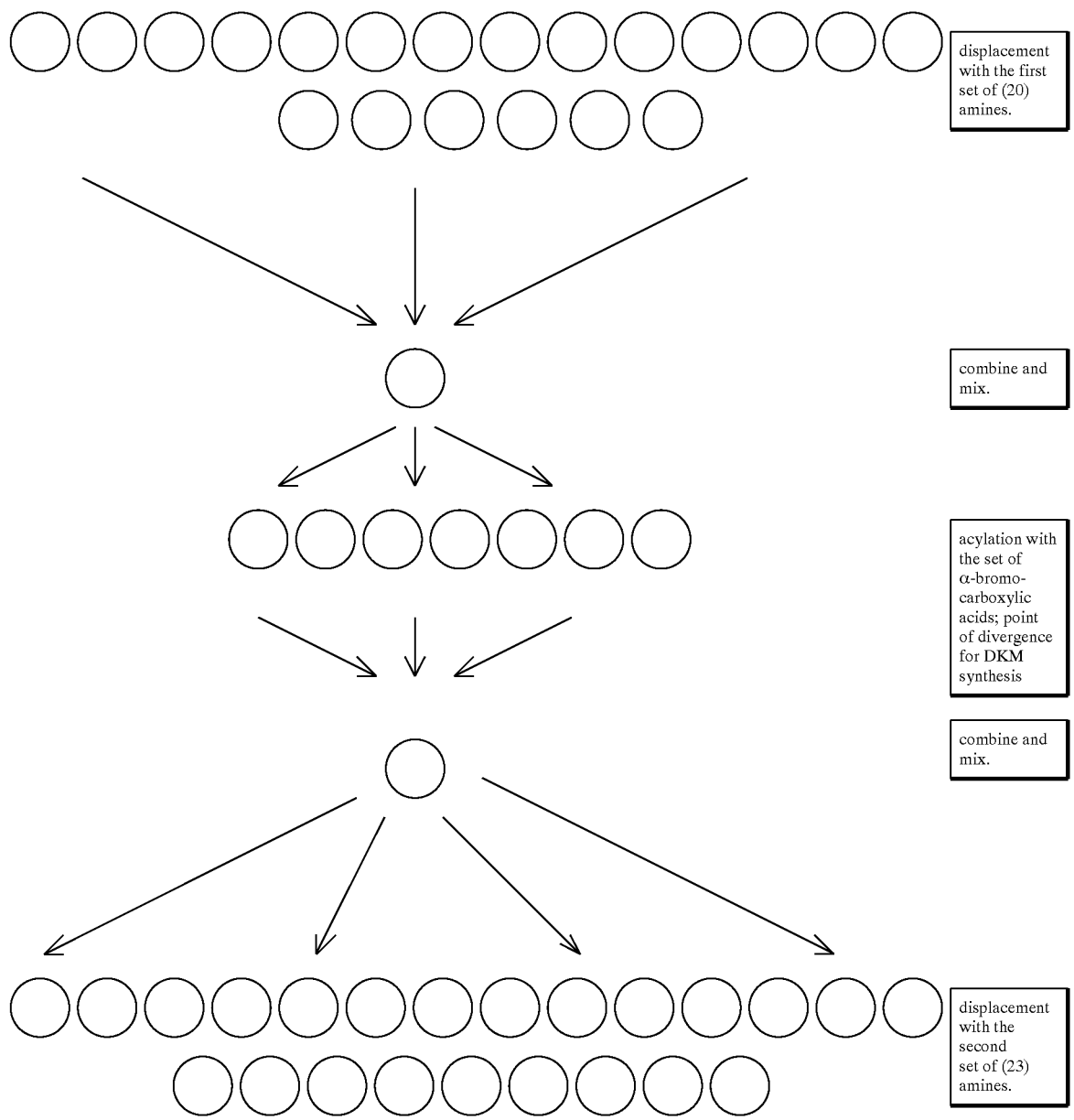
TABLE X
α-Bromocarboxylic acids used in the synthesis of the DKM and DKP libraries.
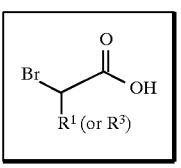

TABLE X-continued
α-Bromocarboxylic acids used in the synthesis of the DKM and DKP libraries.
| α-Bromocarboxylic Acid Substituents |
|---|
| —H |
| —CH$_3$ |
| —CH$_2$CH$_3$ |
| —CH(CH$_3$)$_2$ |
| —CH$_2$—CH$_2$—CH$_3$ |
| =CH$_2$ |
| —Ph |
TABLE XI
Amines used in the synthesis of the DKM and DKP libraries
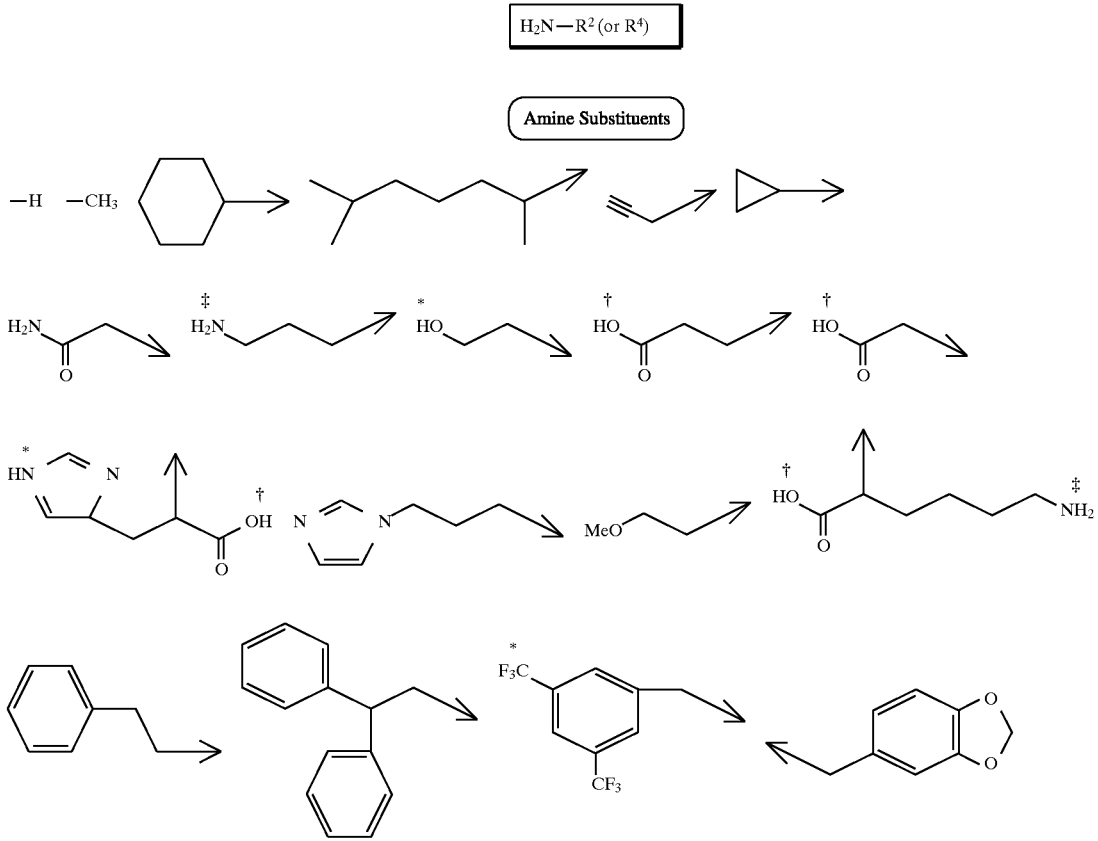

TABLE XI-continued

Amines used in the synthesis of the DKM and DKP libraries

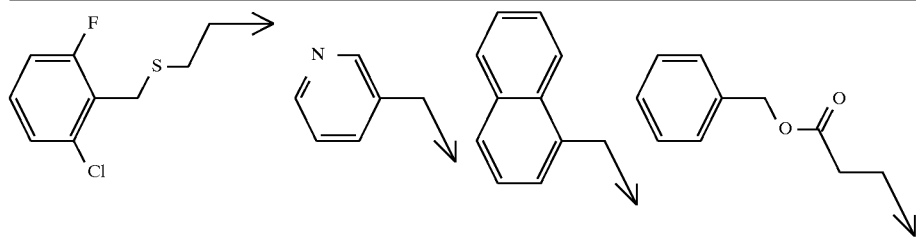

\* - Used Only at R[4]
† - Protected as the t-Bu ester
‡ - Protected as the Boc carbamate The acylated solid supports 2 were combined and mixed well by suspending in DCM. The solid support was distributed into 20 equal portions and each portion was treated with an amine (1–2M in DMSO) from Table XI which lists the amine substituents. Each reaction mixture was agitated at 50° C. for 40 hr. to yield solid support-bound secondary amines 3. The solid supports were recombined, mixed well, and divided into 7 equal portions. Acylation of 3 was accomplished using the same set of α-bromocarboxylic acids (4, 10 eq) in the presence of PyBrop (10 eq) and DIEA (15 eq) in THF at 50° C. In each case the reaction progress was monitored with a solid support-bound ninhydrin test until complete reaction was observed. After washing, portions of the 7 acylated solid supports 5 were separately removed and individually treated with 95% TFA/5% water for one hour at room temperature, washed with DCM (2×10 mL) and the combined filtrates were separately evaporated to afford 7 DKM residues. The residues were lyophilized from glacial acetic acid (3 times). Each of the 7 DKM residues was expected to contain 140 3,4,6-trisubstituted-2,5-diketo-1,4-morpholines (140=7×20).

The remaining acylated solid supports 5 were combined, mixed and divided into 23 equal portions. Each portion was treated with an amine from Table XI (1–2M in DMSO) and the resulting slurries were heated to 70° C. for 96 hr. Each solid support was washed thoroughly with DMSO and DCM and the filtrates were combined and evaporated. Each of the filtrate residues (containing in situ cyclized and released DKP) was added to previously prepared cation exchange resin (AG50W-X8 resin, hydrogen form; washed three times each with DMSO, methanol, DCM) and gently agitated at room temperature for 1 hr. The cation exchange resin was drained and washed with DCM, methanol, DCM, and methanol. The eluents were then concentrated under vacuum to furnish partial DKP filtrates. Each of the 23 solid supports were treated separately with 95% TFA/5% water as described above to cyclize and release the remainder of the DKP. The reaction mixtures were separately filtered into the respective partial DKP filtrates from above. The cleaved solid supports were separately washed with DCM into the respective filtrates from above and evaporated to afford 23 DKP residues. Each DKP residue was lyophilized three times from glacial acetic acid. Nominally, each of the final 23 residues contained 980 1,3,4,6-tetrasubstituted-2,5-diketo-1,4-piperazines (980=7×20×7).

In general, the diketopiperazine and diketomorpholine libraries were prepared using the "split/mix resin" approach in which solid support resin was alternately split into equal portions for reaction with a single acid or amine and then mixed together prior to redistribution for the subsequent reaction (see Scheme 16). The DKM library synthesized in this manner consisted nominally of 980 members in 7 pools of 140 DKMs (7 acids×20 amines×7 acids=980 DKMs). For the DKP library, the additional amine displacement step increased the nominal size of the library (excluding any consideration of diastereomers) to 22,540 DKPs in 23 pools of 980 members (7 acids×20 amines×7 acids×23 amines= 22,540 DKPs). These calculations exclude possible diastereomers that can form for some DKPs which increase the diversity of the library.

An advantage of the above-described DKP/DKM libraries is that the two libraries of structurally and pharmacologically distinct chemotypes were prepared from a common intermediate. Such a strategy of divergent library design is useful in improving the efficiency of library synthesis.

Example 28

Solid-Phase Synthesis of Pyrrolidine Derivatives Bearing a Peptoid Sidechain Monocyclic pyrrolidine derivatives are synthesized by the submonomer method in combination with intermolecular cyclization. For example, a solid support-bound monopeptoid is reacted with 4-bromo-pentenoic acid followed by reaction with a primary amine. The resultant unsaturated peptoid backbone is then reacted via Michael addition with an acceptor molecule having an electron withdrawing group on the olefin. It can be seen from Scheme 17 below, which illustrates this example, that a large number of different and distinct molecules can be synthesized by varying the peptoid sidechain and each of the ring substituents. Each variable substituent is introduced by the various submonomers used in the synthesis of the peptoid backbone as well as by the substituents on the acceptor molecule. The compounds are optionally cleaved from the solid-support by hydrolysis with trifluoroacetic acid as for cleavage of linear peptoids.

75

Scheme 17

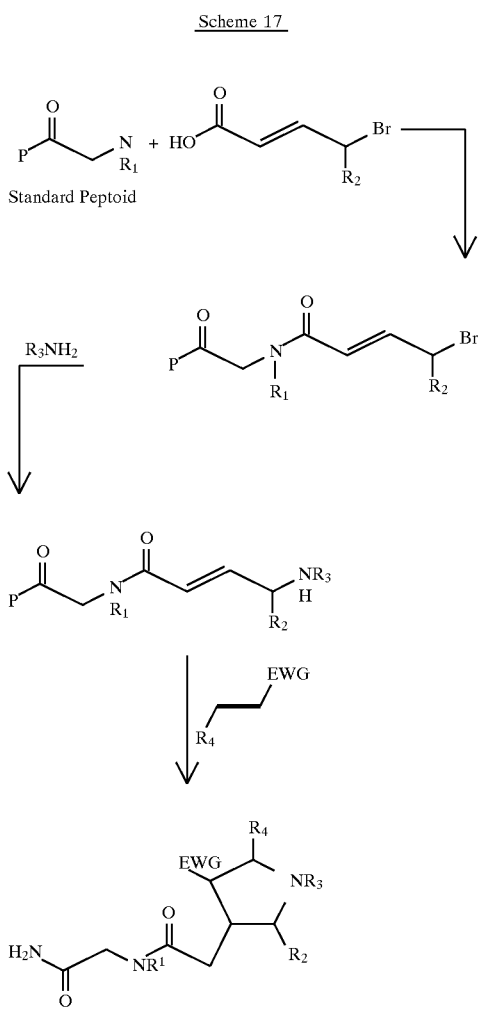

Pyrrolidines having complex ring structures were synthesized by the submonomer method of the invention (see Scheme 10 above and Scheme 18 below). To a heavy walled silanized glass vial was transferred 75 mg of solid support-bound compound A (Scheme 18; $R^1$=isobutyl) prepared as described above for the synthesis of monoketopiperazines from amino acids. N-benzyl maleimide (2.4 mmol), thiophene 2-carboxaldehyde (2.4 mmol), and toluene (3 mL) were added. Argon was bubbled through the solution for 1 min and then the vessel was tightly capped and heated at 105° C. for 16.5 hr. The solid support was filtered off, washed with DMF and dichloromethane and then treated with 95/5 TFA/water for 20 min to cleave the tricyclic compound B from the solid support. HPLC analysis showed four major peaks giving the expected parent ion (MH+) of 495.1. Other aldehydes successfully used in this synthesis included benzaldehyde, terephthalaldehyde, 2-bromobenzaldehyde, 4-dimethylaminobenzaldehyde, 4-hydroxybenzaldehyde, 2,6-dichlorobenzaldehyde, guinoline-2-carboxaldehyde, cinnamaldehyde, and pyridine-2-carboxaldehyde.

76

A further synthesis was performed using multiple maleimides. Solid support A (Scheme 18; 155 mg) was treated with toluene (3 mL), benzaldehyde (3.2 mmol) and a mixture of 3 different maleimides: N-benzyl maleimide, N-ethyl maleimide, and N-cyclohexyl maleimide, all 1.1 mmol. After heating at 110° C. overnight, seven products having the general structure of compound B (Scheme 18) were identified in the product mixture.

Scheme 18 where R1–4=alkyl, aryl; Ar=aryl or heteroaryl; an alkene or alkyne substituted by an EWG such as cinnamates or chalcones can be used in place of the maleimide.

Further synthesis of pyrrolidines by the submonomer method was exemplified by the following procedure. Solid support A (Scheme 19; R=isobutyl) was prepared by the submonomer method of peptoid synthesis. The peptoid solid support (188 mg) was treated at RT with 4 mL of a solution of FMOC-glycine, diisopropylcarbodiimide and 1-hydroxybenzotriazole (all 0.4M) in DMF (2×30 min). The solid support was washed with DMF, then treated 1×5 min and 1×20 min with 3 mL of 20% piperidine in DMF to remove the FMOC group. The intermediate, R=N(iBu)C(O) CH2NH2 (Compound A, Scheme 19), was then refluxed with benzaldehyde (1 mL) and dry toluene (4 mL) for 1 hr. The solid support was rinsed with dichloromethane and then taken up in dry THF (4 mL). Anhydrous LiBr (1.6 mmol) and N-benzylmaleimide (1.6 mmol) were added, followed by triethylamine (1.6 mmol). The reaction was stirred at RT for 17 hr, then washed with DMF and dichloromethane and then treated with 95/5 TFA/water for 20 min to give compound B (Scheme 19) which gave the expected protonated mass spectrometric parent ion of 463.2 where Ar=Ph, R1=benzyl, and R=isobutyl ($C_{26}H_{30}N_4O_4$).

Scheme 19

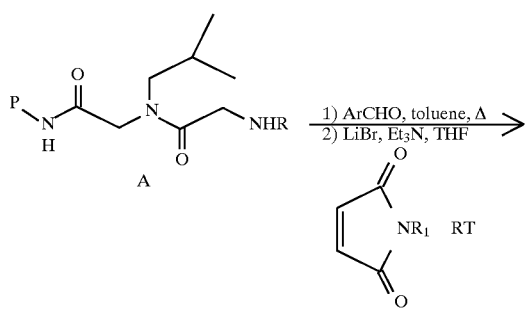

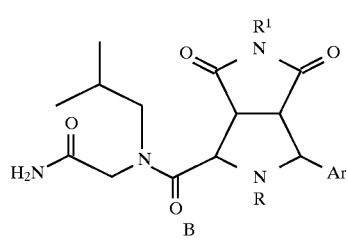

Pyridine carboxylic acids can also be used as submonomer building blocks to make complex organic structures. In the following example, a dihydropyridine having a complex ring structure was prepared by the submonomer method. Rink amide solid support resin (300 mg, 0.55 mmol/gm substitution) was treated 1×10 min and 1×20 min with 4 mL of 20% piperidine in DMF. The solid support was washed 6× DMF. The deprotected solid support was then treated with PyBrop® (1.2 mmol), isonicotinic acid (1.2 mmol), 1,2-dichloroethane (4 mL) and diisopropylethylamine (0.7 mL) overnight at room temperature to give compound A (Scheme 20). Solid support A (200 mg) in DMF (4 mL) with 2'-bromoacetophenone (4 mmol) was heated at 45° C. for 1 hr. The solid support was washed with DMF to give compound B (Scheme 20), which was then stirred with N-benzylmaleimide (0.50 gm) and triethylamine (0.25 mL) in DMF (4 mL) at RT for 1 hr. The solid support was washed with DMF and dichloromethane and dried at RT in vacuo to give compound C (Scheme 20). Half of the solid support was treated with 95/5 TFA/water for 20 min at RT to cleave compound C from the solid support. The expected protonated parent ion (m/e=428) was obtained. The remainder of the solid support was treated with N-methylmaleimide (0.44 gm) in DMF (4 mL) at 80° C. for 16 hr to give solid support D (Scheme 20) which was washed and cleaved from the solid support with 95/5 TFA/water at RT for 20 min. The expected protonated parent ion (m/e=539) was obtained for compound D.

Scheme 20

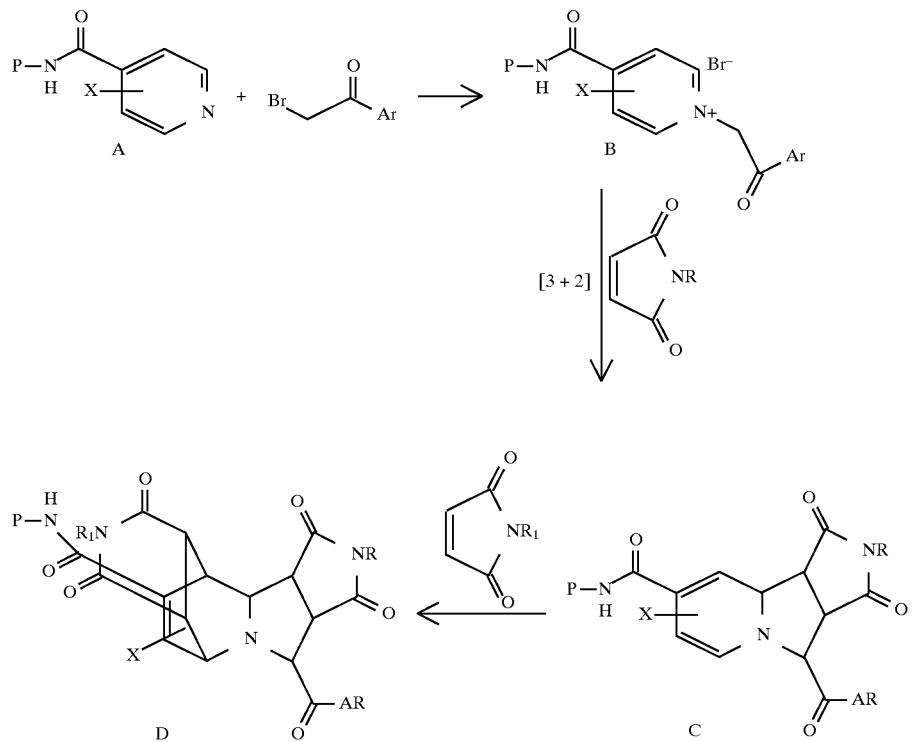

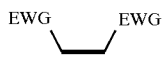

A submonomer procedure similar to that in Scheme 20 was used to synthesize dihydropyridines shown in Scheme 21. Solid support A (R=isobutyl; Scheme 21) was prepared according to the submonomer method on Rink amide solid support resin. The solid support (200 mg) was warmed at 45° C. for 1 hr with a solution of 4,4'-bypyridyl (4 mmol) in DMF (4 mL) (X=4-(4'-pyridyl)) to give solid support-bound pyridinium salt B. To the cooled reaction mixture was added N-benzylmaleimide (0.50 gm) and triethylamine (0.25 mL). After 1 hr mixing at RT, the solid support was washed with DMF and dichloromethane to give compound C (Scheme 21). Half of the derivatized solid support was treated with 95/5 TFA/water for 20 min at RT. The resulting cleaved product gave the expected parent ion (m/e=514, $C_{29}H_{31}N_5O_4$). The remainder of the solid support was treated with a solution of N-methylmaleimide (0.44 gm) in DMF (4 mL) at 80° C. overnight. The crude product was liberated from solid support D as above. The desired product was obtained having the expected parent ion (m/e=625) for $C_{34}H_{36}N_6O_6$ (R=isobutyl, R1=benzyl, R2=methyl, X=4(4'-pyridyl)).

The synthesis as in Scheme 21 was carried out using a variety of 3- or 4- substituted pyridines giving different X groups. Compounds having the following X groups have been synthesized: 4-cyano, 4-formyl, 4-carboxamido, 4-phenyl, 4-(5'-oxazolyl), 4-carbomethoxy, 4-acetyl, 4-p-chlorobenzoyl, 3-fluoro, 3-bromo, 3-methyl, 3-cyano, and 3-carboxamido.

Example 29

Solid-phase Synthesis of Five-membered Cyclic Ureas or Thioureas Bearing a Peptoid Sidechain Cyclic ureas are synthesized by the submonomer method by first reacting peptoids covalently attached to solid-support particles with a halo-alkenoic acid (such as 4-bromo-pentenoic acid) followed by reaction with a primary amine. The resultant unsaturated peptoid is then reacted with an isocyanate R—N=C=O, or an isothiocyanate, R—N=C=S. Intramolecular cyclization under basic conditions yields a 5-membered cyclic urea (or thiourea) having a peptoid sidechain. The variety of such product molecules is controlled by the substituents on the submonomers used to build up the peptoid backbone. Cleavage of the cyclized products from the solid support yields a mixture of compounds which can be tested for biological activity.

The preparation of a library of cyclic ureas by the submonomer method was exemplified in the following procedure. Eight 100 mg portions of solid support A (R1=isobutyl; Scheme 22), prepared according to the submonomer method of peptoid synthesis, were treated with DMF (4 mL), trans-4-bromo-2-butenoic acid (2.4 mmol) and diisopropylcarbodiimide (2.4 mmol) for 0.5 hr at RT. The solid supports were washed with DMF and then each portion was treated with 3 mL of a 2M DMSO solution of a different primary amine for

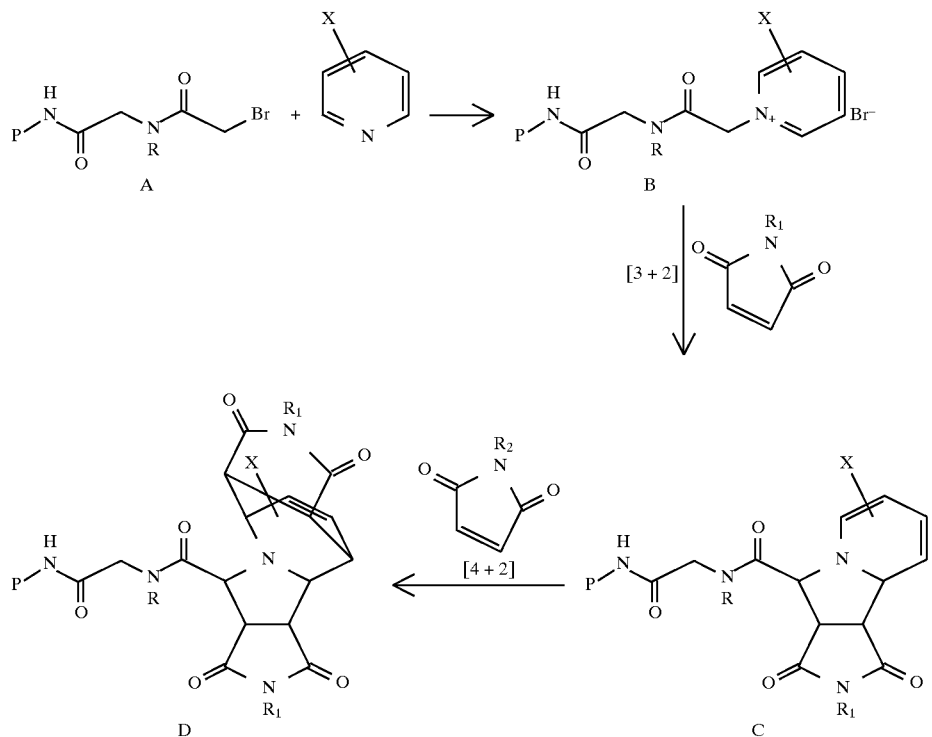

Scheme 21

2 hr at RT. The amines used were allyl amine, cyclopropylmethylamine, benzylamine, aniline, cycloheptylamine, n-hexylamine, 4-aminobiphenyl, and 2,2-diphenylethylamine. The resulting solid supports B (Scheme 22) were washed with DMF, then dichloromethane. The solid supports were combined to make a mixed amine solid support resin which was dried in vacuo. The mixed solid support (75 mg) was then treated with DMF (4 mL), triethylamine (4 mmol) and phenylisocyanate (4 mmol). After 1 hr at RT, the temperature was increased to 55° C. and maintained at that temperature overnight (15 hr). The solid support was washed with DMF, then dichloromethane and treated with 95/5 TFA/water for 20 min at RT. Electrospray mass spectrometry of the product mixture of compounds C (Scheme 22) where R1=isobutyl, R2=8 various, R3=phenyl showed protonated parent ions for all eight of the expected cyclic urea trimers. The m/e of the parent ions containing a particular R2 group are given: allyl (373.2); cyclopropylmethyl (387.2); benzyl (423.2); phenyl (409.2); cycloheptyl (429.2); n-hexyl (417.2); diphenylethyl (513.3); 4-biphenyl (485.3).

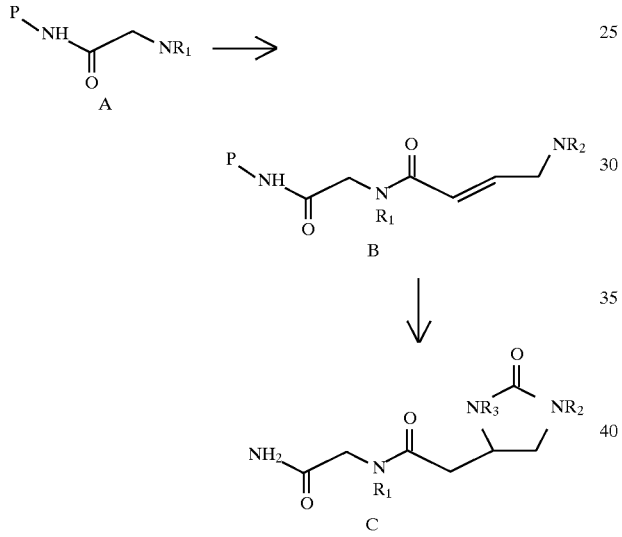

Using mixed amine solid support resin B (Scheme 22), similar libraries were prepared from the following non-inclusive list of isocyanates: allyl isocyanate, cyclohexyl isocyanate, o-bromophenyl isocyanate, p-chlorobenzenesulfonyl isocyanate, 2,4-dimethoxyphenyl isocyanate, 3-acetylphenyl isocyanate, 2,6-dibromo-4-ethylphenyl isocyanate, 2-n-butoxycarbonylphenylisocyanate. Cyclohexyl isothiocyanate has also been used to make cyclic thiourea. In addition, a wide variety of amines and isocyanates have been used to make individual urea dimers as well as trimers.

An example of the preparation of cyclic urea dimers is provided as follows. Rink amide solid support resin (150 mg) was swollen with DMF, then treated 1×5 min and 1×20 min with 3 mL of 20% piperidine in DMF. The solid support was washed with DMF and then treated 2×30 min with a solution of 0.6M trans-4-bromo-2-butenoic acid and 0.6M diisopropylcarbodiimide in DMF (3 mL) to give solid support A (Scheme 23). This solid support was then treated with 3 mL of a 2M solution of isobutylamine in DMSO for 2 hr at RT to give solid support B (R1=isobutyl; Scheme 23). This solid support was treated with a solution of 2,6-dibromo-4-ethylphenyl isocyanate (3 mmol) and triethylamine (3 mmol) in DMF (3 mL) at RT for 1 hr and then at 55° C. for 13 hr. The solid support was washed with DMF and dichloromethane and then treated with 95/5 TFA/water for 20 min at RT. The resulting cyclic urea dimer C (Scheme 23) was then lyophilized twice from acetic acid to give the crude product C. The m/e was as expected for $C_{17}H_{23}Br_2N_3O_2$.

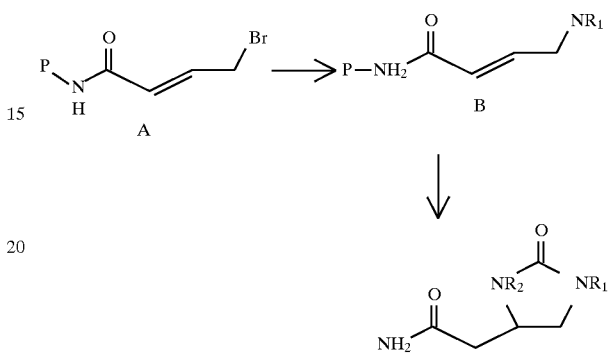

Example 30

Solid-Phase Synthesis of Mixtures of 1,4-Benzodiazepine-2,5-diones

The split-resin method of solid phase synthesis applied to the submonomer method of preparing a peptoid chain was further combined with the Aza-Wittig (Staudinger) reaction to prepare a mixture of 1,4-benzodiazepine-2,5-diones. The diversity of such a mixture derives from the submonomers used in the synthesis. The submonomers include the large number of commercially available primary amines, α-amino acid ester hydrochlorides, easily prepared from α-amino acids, and from aromatic substituents on anthranilic acids.

Synthesis of the 1,4-benzodiazepine-2,5-diones by the submonomer method began with the preparation of a monopeptoid (compound 1; Scheme 24) by acylation of Rink amide solid support resin (Advanced Chemtech, Louisville, Ky.) with bromoacetic acid followed by amination with isobutyl amine (Zuckermann, R. N. et al. (1992) J. A. C. S. 114:10646). Bromoacetylation and displacement with an amino acid methyl or ethyl ester free base in DMSO gave Compound 2 as an intermediate. Compound 2 was acylated directly with a freshly prepared o-azidobenzoyl chloride to produce compound 3. Treatment of solid support-bound compound 3 with $Bu_3P$ in toluene at room temperature gave the iminophosphorane. The solid support was washed and heated at greater than 125° C. for more than 2 hours, preferably at 130° C. for 5–7 hr, as appropriate for the particular amino acid ester used, to give the benzodiazepinedione. Treatment of the solid support with 95/5 TFA/$H_2O$ cleaved the benzodiazepinedione from the solid support to yield compound 4. It can be seen that compound 4 can be a mixture of many compounds when the substituents on the submonomers are varied. Following cleavage from the solid support, the benzodiazepine products can be purified by standard techniques known to those of ordinary skill in the art. For example, compound 4 was lyophilized twice from glacial acetic acid to give a powder. All of the products listed in Table XII showed the expected parent ions by FAB or electrospray mass spectrometry.

Scheme 24

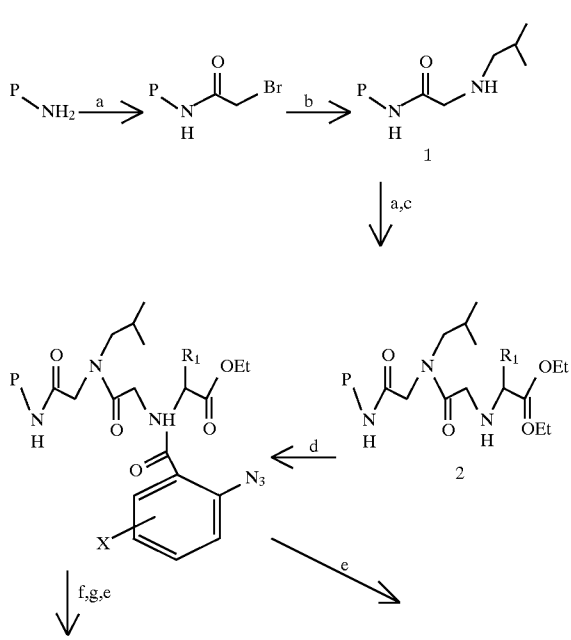

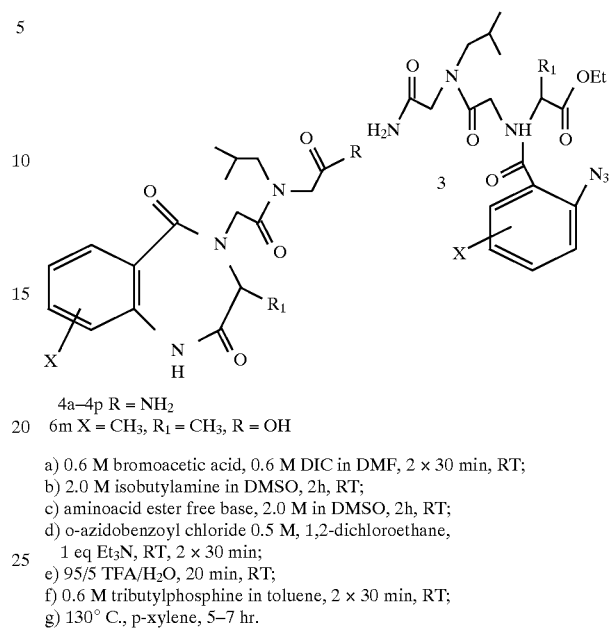

4a–4p R = NH₂
6m X = CH₃, R₁ = CH₃, R = OH a) 0.6 M bromoacetic acid, 0.6 M DIC in DMF, 2 × 30 min, RT;
b) 2.0 M isobutylamine in DMSO, 2h, RT;
c) aminoacid ester free base, 2.0 M in DMSO, 2h, RT;
d) o-azidobenzoyl chloride 0.5 M, 1,2-dichloroethane, 1 eq Et₃N, RT, 2 × 30 min;
e) 95/5 TFA/H₂O, 20 min, RT;
f) 0.6 M tributylphosphine in toluene, 2 × 30 min, RT;
g) 130° C., p-xylene, 5–7 hr.

TABLE XII

Characterization of hybrid peptoid-1,4-benzodiazepine-2,5-diones.

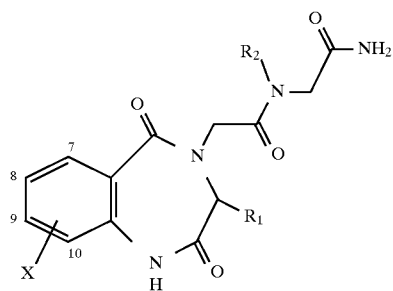

| Entry | X | R₁ | R₂ | Yield[a] | Purity[b] |
|---|---|---|---|---|---|
| 4a | H | H | i-Bu | 55 | >65 |
| 4b | H | Me | i-Bu | 55 | 80 |
| 4c | 9-Cl | Me | i-Bu | >90 | 79 |
| 4d | H | CH₂Ph | i-Bu | 41 | 92 |
| 4e | H | Ph | i-Bu | 53 | >95 |
| 4f | H | CH₂OH | i-Bu | 34 | 80 |
| 4g | H | CH₂(pOH)Ph | i-Bu | 68 | 61 |
| 4h | H | i-Pr | i-Bu | 41[c] | 72 |
| 4i | H | CH₂CO₂H | i-Bu | 52 | 69 |
| 4j | H | (CH₂)₂CO₂H | i-Bu | 60 | 70 |
| 4k | H | (CH₂)₄NH₂ | i-Bu | 50 | 97 |
| 4l | H | (CH₂)₃NH₂ | i-Bu | 90 | 63 |
| 4m | 10-Me | Me | i-Bu | 37 | 61[d] |
| 4n | 8-OTf | Me | i-Bu | n.d. | 88 |
| 4o | 8-NO₂ | Me | i-Bu | n.d. | 93 |
| 4p | H | CH(OH)CH₃ | i-Bu | 50 | 59 |
| 4q | H | Me | 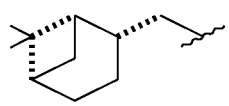 | 75 | 93 |

TABLE XII-continued

Characterization of hybrid peptoid-1,4-benzodiazepine-2,5-diones.

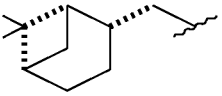

| Entry | X | R₁ | R₂ | Yield[a] | Purity[b] |
|-------|---|------|------|-------|--------|
| 4r | H | CH₂Ph | 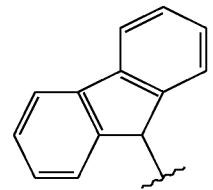 | 55 | 84 |
| 4s | H | Me | 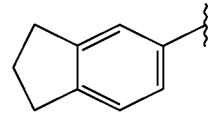 | 41 | 85 |
| 4t | H | Me | 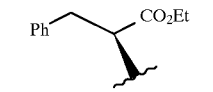 | 58 | 83 |
| 4u | H | CH₂Ph | Ph–CH(–)–CO₂Et | 49 | 64 |

[a]Crude yield from 0.085–0.5 mmol of starting resin;
[b]Purity determined by C-18 RP hplc, monitoring at 214 nm, gradient 0–80% acetonitrile with H₂O containing 0.1% TFA over 40 min;
[c]Plus 24% uncyclized 2h;
[d]Plus 26% acid 6 m.

The amino acid ester submonomers used in preparing the compounds in Table XII included L-amino acid esters of alanine, phenylalanine, phenylglycine; tyrosine, serine, and threonine (protected as O-t-butyl ethers); aspartic and glutamic acids (protected as γ- or δ-t-butyl esters); and ornithine and lysine (δ- or ε-Boc protected). Steric hinderance of some side chains may affect the yield of a product as can be readily determined by one of ordinary skill in the art.

The preparation of a library of 1,4-benzodiazepine-2,5-diones began with the independent syntheses of seven monopeptoid-solid supports having the following side chains: 3-aminopropyl, tetrahydrofurfurylmethyl, cyclopropylmethyl, piperonyl, benzyl, cycloheptyl, 4-biphenylyl. These were mixed in equimolar amounts, then reacted with bromoacetic acid/DIC followed by treatment with L-phenylalanine ethyl ester to give a diverse mixture of seven dipeptoids on solid support. Acylation with o-azidobenzoyl chloride, treatment with Bu₃P and cyclization in p-xylene for 5 hr at 130° C. followed by TFA/H₂O cleavage resulted in a mixture showing seven major peaks by reverse phase (C-18) HPLC. Electrospray mass spectrometry of the crude product showed all of the seven expected parent ions. The amine, amino acid, and azide submonomers can be varied to expand the diversity of the library.

Modification of the aromatic substituents on the solid support can be performed to further increase the diversity of the library. For example, the reaction of solid support-bound compound 4o with phenylboronic acid under Suzuki conditions (Oh-e, T. et al. Synlett. 1990:221; Deshpande, M. S. (1994) Tet. Lett. 31:5613) gave the corresponding 8-phenyl benzodiazepinedione. Reduction of the 3-nitro groups of compound 4p with SnCl2-H2O (MeOH, reflux 3 hr) gave the 8-amino derivative which was subsequently acylated with benzoylchloride while still attached to the solid support. Thus, for this or other libraries prepared by the submonomer method, the diversity of the library is controlled by the substituents on the submonomers as well as the modifications that can be made to those substituents after their incorporation into the peptoid backbone.

Example 31
Preparation of a Library of Cyclized Peptoid Compounds of Different Cyclic Structures Each Bearing a Peptoid Sidechain The versatility of the submonomer method for preparing a mixture of compounds having different cyclic structures is further demonstrated in the following example. It clear from the above examples that acid halides, carboxylic acids, and amines are submonomers common to the synthetic steps of the invention. Where a synthetic step for one cyclic compound can utilize the same submonomer as a synthetic step for a different cyclic compound, the solid support-bound peptoid reactants can be combined and reacted in the same vessel. The products of the common reaction can be apportioned and recombined with other solid-support bound peptoids for different common reactions. The result of portioning and recombining, as well as common and separate reactions yields a complex library of compounds. These compounds vary not only in the substituents introduced by the submonomers but in the cyclic structure to which the substituents are attached. By this procedure, a library of compounds having different cyclic structures by the submonomer method.

It can be seen from the examples described herein that a vast number of compounds of different cyclic structure and a wide variety of substituents can be synthesized by the solid-phase submonomer method in combination with reactions promoting intra- or intermolecular cyclization. Libraries containing large numbers of different and distinct members can be prepared by applying to the above combination of synthetic methods the additional method of portioning and recombining portions of the solid support particles such that the peptoid backbone is built up of a variety of submonomers prior to cyclization.

The cyclic compounds of the invention are useful as candidate therapeutic agents. Libraries of cyclic compounds of the invention are useful in that many candidate compounds are synthesized simultaneously and with controlled variations in substituent composition. Such libraries containing many candidate compounds are rapidly and conveniently screened for biological activity such a binding to a receptor of interest, binding to an antibody, binding to poly nucleic acids, and the like.

This application is related to an application entitled "Combinatorial Libraries of Substrate-Bound Cyclic organic Compounds", Attorney Docket No. 06515/023001 filed on the same day herewith, which is assigned to the same assignee as the present application.

The instant invention is shown and described herein in what is considered to be the most practical, and preferred embodiments. It is recognized, however, that departures can be made therefrom which are within the scope of the invention, and that obvious modifications will occur to one skilled in the art upon reading this disclosure.

What is claimed is:

1. A method of synthesizing a library of cyclic organic compounds comprising N-substituted polyamides by the method comprising:
   (a) preparing a library of N-subsituted polyamide compounds on solid support surfaces by:
      (1) dividing a plurality of solid support surfaces having derivatized thereon an amine into a plurality of subamounts;
      (2) acylating the amine on the surface of each subamount of step (1) with a first submonomer acylating agent comprising a leaving group that is susceptible to nucleophilic displacement by an amine of a second submonomer to obtain an acyl group bonded to the amine on the surface of each subamount, wherein the acylated amine thereby obtained has positioned thereon said leaving group;
      (3) pooling the support surfaces of each subamount of step (2) and mixing;
      (4) dividing the pool of step (3) into a plurality of subamounts; and
      (5) reacting the acylated solid support on each subamount of step (4) with a sufficient amount of a second submonomer displacing agent comprising an amino group so as to effect nucleophilic displacement of the leaving group and drive the reaction to completion, wherein said second submonomer agent is different from said first submonomer acylating agent;
      (6) pooling the reacted subamounts of step (5); and
      (7) optionally repeating steps 1 to 6 with third and fourth submonomers, wherein said third submonomer is an acylating agent comprising a leaving group and said fourth submonomer is a displacing agent comprising an amino group whereby a library of N-substituted polyamide compounds on solid support surfaces is produced; and (b) contacting the N-substited polyamides with an agent which cyclizes the N-substituted polyamides;

whereby said library of cyclic organic compounds comprising N-substituted polyamides is obtained.

2. The method of claim 1, wherein each first submonomer is indepedently a substituted acylating agent of the formula:

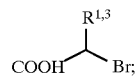

each second and fourth submonomer is independently a primary amine of the formula $R^2$—$NH_2$ or $R^4$—$NH_2$, respectively;

each leaving group is independently a halogen; and each cyclic organic compound obtained by the process of claim 1 is independently a tetrasubstituted-2,5-diketo-1,4-piperazine compound of the formula

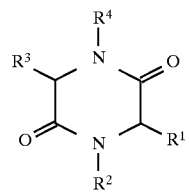

wherein $R^1$, $R^2$, $R^3$ and $R^4$ are independently any side chain attachable to the nitrogen or carbon atom.

3. The method according to claim 1, wherein each first submonomer is independently a halo-substituted alkenoic acid of the formula:

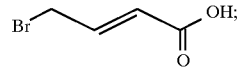

each second submonomer is independently a primary amine of the formula R—$NH_2$;

each third submonomer is independently an acid halide having a leasing group attached to the substituent, wherein the third submonomer has the formula:

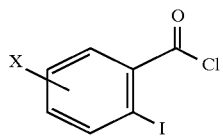

each cyclic organic compound obtained by the process of claim 1 is independently a 1-(2H)-isoquinolone compound of the formula

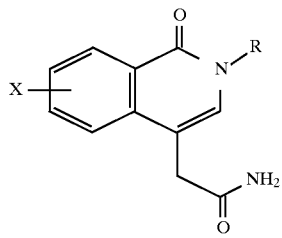

wherein each occurrence of X within the library of isoquinolones is independently any moiety attachable to the aromatic ring and R is independently any side chain attachable to the nitrogen or carbon atom.

4. The method of claim 1, wherein each amine attached to the solid support is independently a peptoid;

each first submonomer is independently a halo-substituted aryl primary amine of the formula

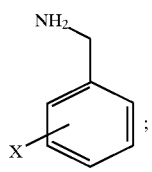

each second submonomer is independently a substituted alkenoic acid of the formula

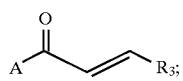

said cyclic organic compound obtained by the process of claim 1 is a tetrahydroisoquinolinone of the formula

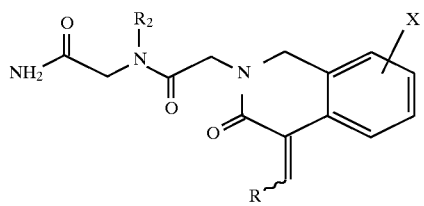

where R, $R_3$, $R_2$ are independently any side chain attachable to the nitrogen or carbon atom, and where X and A are independently a halogen.

5. The method of claim 1, wherein each first submonomer is independently a halo substituted alkenoic acid of the formula

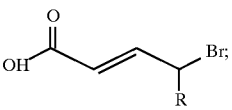

each second submonomer is independently a primary amine of the formula

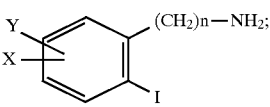

each cyclic organic compound obtained by the process of claim 1 of the formula

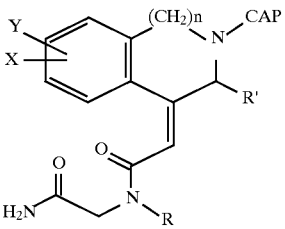

where n is 1,2, or 3; and X,Y are independently any moiety attachable to the aromatic ring; R, R' are independently any side chain attachable to the nitrogen or carbon atom; and where "CAP" is —H, R, or is selected from the group consisting of moieties of the formula

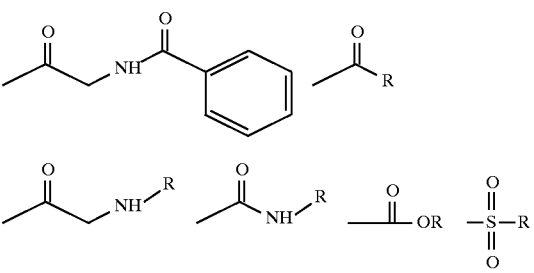

6. A method of synthesizing a library of cyclic organic compounds comprising N-substituted polyamides by the method comprising:

(1) dividing a plurality of solid support surfaces having derivatized thereon a peptoid comprising a leaving group;

(2) reacting each subamount of step (1) with a first submonomer of the formula:

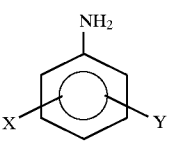

(3) pooling the support surfaces of each subamount of step (2) and mixing;

(4) dividing the pool of step (3) into a plurality of subamounts;

(5) reacting each of the subamounts produced in step (4) with a submonomer of the formula:

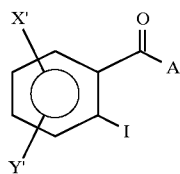

(6) pooling the reacted subamounts of step (5); and
(7) cyclizing the products of step (6) to produce a phenanthridone compound of the formula:

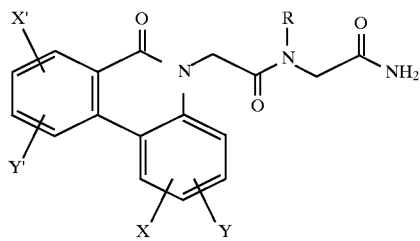

where X, Y, X', and Y' are independently any moiety attachable to the aromatic ring; R is any side chain attachable to the nitrogen or carbon atom; and where A is a halogen.

7. A method of synthesizing a library of cyclic organic compounds comprising N-substituted polyamides by the method comprising:
(1) dividing a plurality of solid support surfaces having derivatized thereon an amine into a plurality of subamounts;
(2) reacting said subamounts of step (1) with a first submonomer of the formula:

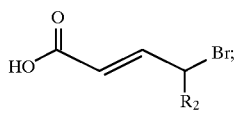

(3) pooling the support surfaces of each subamount of step (2) and mixing;
(4) dividing the pool of step (3) into a plurality of subamounts; and
(5) reacting the subamounts of step (3) with a second submonomer of the formula $R_3NH_2$;
(6) pooling the reacted subamounts of step (5); and
(7) reacting the subamounts of step (6) with a third submonomer of the formula

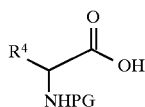

where PG is an amine protecting group;
(8) pooling the reacted subamounts of step (7);
(9) deprotecting the subamounts of step (8); and
(10) cyclizing the subamounts of step (9) to produce a compound of the formula:

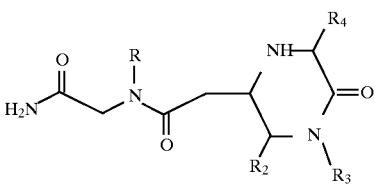

where R, $R_2$, $R_3$, $R_4$ are independently any side chain attachable to the nitrogen or carbon atom.

8. A method of synthesizing a library of cyclic organic compounds comprising N-substituted polyamides by the method comprising:
(a) preparing a library of N-subsituted polyamide compounds on solid support surfaces by:
(1) dividing a plurality of solid support surfaces into a plurality of subamounts;
(2) acylating each subamount of step (1) with a first submonomer acylating agent of the formula

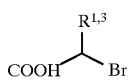

(3) pooling the support surfaces of each subamount of step (2) and mixing;
(4) dividing the pool of step (3) into a plurality of subamounts;
(5) reacting the acylated solid support on each subamount of step (4) with a sufficient amount of a second submonomer displacing agent of the formula $R^2—NH_2$;
(6) pooling the reacted subamounts of step (5);
(7) dividing the pool of step (6) into a plurality of subamounts;
(8) reacting the solid support of each subamount of step (7) with a third submonomer acylating agent of the formula:

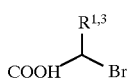

; and
(9) pooling the reacting subamounts of step (8);
whereby a library of N-substituted polyamide compounds on solid support surfaces is produced; and
(b) contacting the N-substituted polyamides with an agent which cyclizes the N-substituted polyamides;
thereby producing said library contains cyclic organic compounds of the formula:

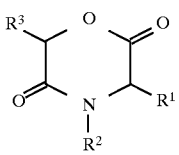

wherein R1, R2 and R3 are independently any side chain attachable to the nitrogen or carbon atom.

* * * * *